US006974665B2

(12) United States Patent
Berkowitz et al.

(10) Patent No.: US 6,974,665 B2
(45) Date of Patent: Dec. 13, 2005

(54) IN SITU SCREENING TO OPTIMIZE VARIABLES IN ORGANIC REACTIONS

(75) Inventors: David B. Berkowitz, Lincoln, NE (US); Mohua Bose, La Jolla, CA (US); Sungjo Choi, Chonan (KR)

(73) Assignee: University of Nebraska, Lincoln, NE (US)

( * ) Notice: Subject to any disclaimer, the term of this patent is extended or adjusted under 35 U.S.C. 154(b) by 342 days.

(21) Appl. No.: 10/235,950

(22) Filed: Sep. 6, 2002

(65) Prior Publication Data

US 2003/0148257 A1 Aug. 7, 2003

Related U.S. Application Data

(60) Provisional application No. 60/317,810, filed on Sep. 6, 2001, provisional application No. 60/371,159, filed on Apr. 10, 2002, and provisional application No. 60/386,438, filed on Jun. 7, 2002.

(51) Int. Cl.$^7$ ............................ C12Q 1/00; C12Q 1/28; C12Q 1/32; C12Q 1/34; C12Q 1/42

(52) U.S. Cl. ............................ 435/4; 435/15; 435/18; 435/21; 435/26; 435/28

(58) Field of Search ............................ 435/14, 15, 18, 435/21, 26, 28

(56) References Cited

U.S. PATENT DOCUMENTS 6,599,754 B2 * 7/2003 Miller et al. ................ 436/178

FOREIGN PATENT DOCUMENTS

| WO | WO 94/08051 | 4/1994 |
| WO | WO 99/19724 | 4/1999 |
| WO | WO 99/21957 | 5/1999 |
| WO | WO 99/36375 | 6/1999 |
| WO | WO 99/54337 | 10/1999 |
| WO | WO 99/56699 | 11/1999 |
| WO | WO 00/14034 | 3/2000 |
| WO | WO 00/20428 | 4/2000 |
| WO | WO 00/43771 | 7/2000 |
| WO | WO 00/58003 | 10/2000 |
| WO | WO 00/72968 | 12/2000 |
| WO | WO 01/18528 | 3/2001 |

OTHER PUBLICATIONS

Kutnz et al., "Combinatorial catalyst discovery", Current Opinion in Chemical Biology 3 (3): 313–319 (1999).*
"In Situ Enzymatic Screening (ISES): A Tool for Catalyst Discovery and Reaction Development"; David Berkowitz, Mohau Bose, and Sungjo Choi; *Angew. Chem. Int. Ed. 2002*, 41, No. 9; pp. 1603–1607.
Burnell, J.N. et al., "A New, Rapid, and Sensitive Assay for Adenosine 5'-Phosphosulphate (APS) Kinase", *Analytical Biochemistry* 68, 281–288 (1975).

Alexander B. Roy, "Arylsulfatases: Colorimetric and Fluorometric Assays", *Methods in Enzymology*, vol. 143, pp. 207–217 (1987).
J.H. Van Boom et al., *Tetrahedron Letters* No. 43, pp 3785–3788, 1974.
H. Gerit et al., "Purification of Properties of a Phophyohydrolase from *Enterobacter aerogenes*", *The Journal of Biological Chemistry*, vol. 250, No. 18, pp. 5053–5058.
Dibbelt, et al., *Biological Chemistry Hoppe–Seyler*, vol. 372, pp. 173–185, Mar. 1991.
B. Jandeleit et al., "Combinatorial Methods in Catalysis", vol. 2, No. 2, (1998), pp. 101–123.
P.J. Matts et al., Purification and Characterization of the Short Chain Alkylsulphatase of Coryneform B1a, vol. Biochem. J. (1994) 304, pp. 937–943.
P.M. Clarke et al., "An Enzymatic Assay for Acetate in Spent Bacterial Culture Supernatants", *Analytical Biochemistry* 130, pp. 402–405 (1983).
J. Torreilles et al., "Influence of Coenzyme Structure of the Transient Chemical Intermediate Formed During Horse–Liver Alcohol–Dehydrogenase–Catalyzed Reduction of Aromatic Aldehydes", *Biochimica et Biophysica Acta* 869 (1986) pp 265–274.
T. Bateman et al., "Primary Alkylsulphatase Activities of the Detergent–Degrading Bacterium Pseudomonas C128", *Biochemical J*, (1986), vol. 236, pp. 401–408.
Lavastre et al., Discovery of Novel Catalysts for Allylic Alkylation with a Visual Colorimetric Assay, *Angew Chem. Int. Ed.* 1999, 38, No. 21, pp. 3163–3165.
S.J. Taylor et al., "Thermographic Selection of Effective Catalysts from an Encoded Polymer–Bound Library", *Science*, vol. 280, pp 267–270, (1998).
K. Shaughnessy et al., "A Fluorescence–Based Assay for High–Throughput Screening of Coupling Reactions. Application to Heck Chemistry", *J. Am Chem. Soc.*, vol. 121, No. 10, 2123–2132 (1999).
S. Senkan, "High–Throughput Screening of Solid–State Catalyst Libraries", *Nature*, vol. 394, Jul. 23, 1998, pp 350–352.

(Continued)

Primary Examiner—Sandra Saucier
(74) Attorney, Agent, or Firm—Banner & Witcoff Ltd.

(57) ABSTRACT

A biphasic process for rapid screening of organic reactions comprising monitoring relative rates of parallel organic reactions. The screening process is suitable to determine the efficacy of different reactants, process conditions, and process enhancers such as catalysts or promoters. The biphasic process also allows multiple samples to be analyzed/monitored simultaneously. In addition because enzymes are used to monitor the reaction product in this invention, when that product is chiral and an enantio-discriminating enzyme is used to monitor the product, in addition to the relative rates, enantioselectivities of a set of parallel organic reactions can also be determined. The monitoring is done in situ and thus removal of aliquots for separate testing is unnecessary

35 Claims, 11 Drawing Sheets

OTHER PUBLICATIONS

T. Berg et al., "High–Throughput Synthesis and Direct Screening for the Discovery of Novel Hydrolytic Metal Complexes", *Bioorganic & Medicinal Chemistry Letters 8,* (1998), pp1221–1224.

S. Taylor et al., "Catalytic Diastereoselective Reductive Aldol Reaction: Optimization of Interdependent Reaction Variables by Arrayed Catalyst Evaluation", *J. Am. Chem. Soc.* 1999, 121, pp. 12202–12203.

H. Su et al., "High–Throughput Screening of Heterogeneous Catalysts by Laser–Induced Fluorescence Imaging", *J. Am. Chem. Soc.,* vol. 122, No. 30, 2000, pp. 7422–7423.

J. Porter et al., "Ti–Catalyzed Regio– and Enantioselective Synthesis of Unsaturated α–Amino Nitriles, Amides, and Acids. Catalyst Identification through Screening of Parallel Libraries", *J. Am. Chem. Soc.,* 2000, vol. 122, No. 11, pp. 2657–2658.

A. Cooper, "Reactive Dyes as a Method for Rapid Screening of Homogeneous Catalysts", *J. Am. Chem.Soc.,* 1998, 120, pp. 9971–9972.

A. Porte et al., "Design and Optimization of New Phosphino Oxazoline Ligands via High–Throughput Catalyst Screening", *J. Am. Chem. Soc.* 1998, 120, pp. 9180–9187.

C. Gennari et al., "Investigation of a New Family of Chiral Ligands for Enantioselective Catalysis via Parallel Synthesis and High–Throughput Screening", *J. Org. Chem.* 1998, 63, pp. 5312–5312.

K. Shimizu et al., "Search for Chiral Catalysts Through Ligan Diversity: Substrate–Specific Catalysts and Ligand Screening on Solid Phase", *Angew. Chem. Int. Ed. Engel,* vol. 136, No. 16, pp. 1704–1707 (1997).

R. Harris et al., "A Polymeric and Fluorescent Gel for Combinatorial Screening of Catalysts", *J. Am. Chem. Soc.,* 2000, 121, pp. 11270–11271.

G. Copeland et al., "A Chemosensor–Based Approach to Catalyst Discovery in Solution and on Solid Support", *J. Am. Chem. Soc.,* 1999, 121, pp. 4306–4307.

T. Onokuchi., "Lewis Acid Catalyzed Procedure for Selective Conversion of the Carboyclic Dials–Alder Adducts of Danishefsky's Diene to 2–Cyclohexanones and its Extension to Their One–Pot Syntheses", *Synlett,* 2000, No. 11, pp. 1549–1552.

A. Ghosh et al., "Synthetic of Antitumor Macrolide Laulimalide: Enantioselective Synthesis of the $C_3$–$C_{14}$ Segment By a Catalytic Hetero Diels–Alder Strategy", *Tetrahedron Letters,* vol. 38, No. 14, pp. 2427–2430, 1997.

S. Schaus et al., "Asymmetric Hero–Diels–Alder Reactions Catalyzed by Chiral (Salen) Chromium (III) Complexes", *J. Org. Chem.,* 1996, 63, 403–405.

K. Maruoka et al., "Asymmetric Hetero–Diels–Alder Reaction Catalyzed by Chiral Organoaluminum Reagent", *J. Am. Chem. Soc.,* 1988, 110, 310–312.

H. Furuno et al., "Remarkably High Asymmetric Amplification In the Chiral Lanthanide Complex–Catalyzed Hetero–Diels Alder Reaction: First Example of the Nonlinear Effect In $ML_3$ System", *Org. Lett.,* vol. 2, No. 1, 2000, pp. 49–52.

S. Yao et al., "Catalytic Asymmetric Hetero–Diels–Alder Reactions of Ketones: Chemzymatic Reactions", *J. Am Chem. Soc.,* 1998, 120, 8599–8605.

\* cited by examiner (a) CAN, MeCN/H2O (2:1) (78%); (b) Boc2O, NEt3, CH2Cl2 (88%); (c) Cs2CO3, MeOH (88%); (d) CrO3, H2SO4 (aq), acetone (82%); (e) TFA, CH2Cl2 (84%, isolated as the TFA salt).

(a) MeP(O)(OEt)2, n-BuLi, THF, -40°C, 30 min; EtO2CCl, 30 min; then 0.3N HCl, warm to rt (68%); (b) p-MeO-C6H4NCO, pyr, (96%); (c) CAN, MeCN/H2O (2:1) (89%); (d) Boc2O, LiHMDS, THF (85%); (e) Cs2CO3, EtOH (95%); (f) CrO3, H2SO4 (aq), acetone (76%); (g) TMSBr, CH2Cl2 (80%; isolated as the ammonium salt).

IN SITU SCREENING TO OPTIMIZE VARIABLES IN ORGANIC REACTIONS

This application claims priority to U.S. provisional applications: 60/317,810 filed Sep. 6, 2001; 60/371,159 filed Apr. 10, 2002; and 60/386,438 filed Jun. 7, 2002, each of which is herein incorporated by reference in its entirety.

FIELD OF THE INVENTION

This invention relates to methods for screening catalysts and for optimizing variables in organic reactions.

BACKGROUND OF THE INVENTION

The discovery of new and improved catalysts is a fundamental goal in chemistry, and in particular in the field of combinatorial catalysis. There is also a need to improve chemical reactions generally, including those without catalysts. Chemists in academia and industry have responded to constant pressures to make reactions more efficient and more practical by developing techniques to screen organic reactions to determine the efficacy of various catalysts of interest and optimize various reaction parameters. These screening techniques are designed to identify the effectiveness of a catalyst or other variable in a reaction by monitoring a certain parameter or aspect of a reaction. Of particular convenience are screening systems that allow for the continuous monitoring of a series of reactions, without the need to withdraw aliquots and work these up prior to analysis.

Gas and liquid chromatography have frequently been employed in conjunction with time-point detection systems. Although chromatography-based methods (i.e. GC or HPLC) are among the most common catalyst screening tools used they do not conveniently give kinetic profiles of the reaction being screened. This is because these are time-point assays so each [product] vs. time data point requires taking an aliquot out of the reaction working it up, then quantitating the product. Steven J. Taylor and James P. Morken in *Catalytic Diastereoselective Reductive Aldol Reaction: Optimization of Interdependent Reaction. Variables By Arrayed Catalyst Evaluation*, J. Am. Chem. Soc. (1999) 121: 12202, investigated the efficacy of transition metal catalysts in catalyzing the stereoselective reductive coupling of α,β-unsaturated esters and aldehydes. The reactions were allowed to proceed for 16 hours and analyzed by GC and compared to an internal standard to determine relative conversion and stereoisomer ratios. Although relative conversion and stereoisomer ratios could be determined and compared for all of the reactions at the completion of the reaction, the relative rates at which the reactions proceeded during the 16 hours were not determined, because to do so would have required physically taking multiple time point quenches of each reaction and analyzing each one by GC or HPLC. In *Ti-Catalyzed Region-and Enantioselective Synthesis of Unsaturated a-Amino Nitriles, Amides, and Acids. Catalyst Identification through Screening of Parallel Libraries*, J. Am. Chem. Soc. (2000) 122: 2567, Porter, James R. et al. investigated the titanium catalyzed enantioselective addition of cyanide to α,β-unsaturated aryl imines. The enantioselectivity and conversion were determined by chiral HPLC. However, this determination was made only at the completion of the reaction. The procedure as described by the authors does not provide a means for comparison of the kinetics of the reactions. Thus, while the yield and enantioselectivity of reactions can be determined using gas or liquid chromatography with a chiral stationary phase, relative rate kinetic information for the reactions is not readily available.

Another such screening method is IR thermography. In *Thermographic Selection of Effective Catalysts from an Encoded Polymer-Bound Library* (Science (1998) 280:267–70), Steven J. Taylor and James P. Morken, developed a method for the evaluation of multifunctional catalysts bound to polymers for the catalysis of a simple esterification reaction. Parallel to this work, the group of Manfred Reetz developed a similar technique for examining kinetic resolutions of alcohols by lipase-mediated acylation and resolution of epoxides by ring-opening using Jacobsen-like catalysts (M. T. Reetz, M. H. Becker, K. M. Kühlung, A. Holzwarth *Angew. Chem. Int. Ed.* 1998, 37, 2647–2650). Utilizing the phenomenon that most chemical reactions have a measurable heat of reaction $\Delta H_r^\circ$, the effectiveness of catalysts in a library of catalysts was evaluated using a parallel library assay. The most active catalyst was identified by the greatest temperature change, utilizing IR thermography. This method, however, suffers from the limitation that there is no direct evidence of product formation and there is certainly no readily available means of identifying the nature of the product formed. Thus, undesired reactions often are exothermic and would lead to "false positives" in this screen. The Reetz group later showed that endothermic reactions might also lend themselves to IR thermographic screening (M. T. Reetz, M. H. Becker, M. Leibl, A. Fürstner, *Angew. Chem. Int. Ed.* 2000, 39, 1236–1239). Here the most active catalyst is to produce the greatest heat uptake. In the reaction studied, ring-closing metathesis, evaporation of a volatile byproduct, ethylene, was also endothermic. While this turned out to enhance the signal in this case, it points to another potential source of "false positives" in such a screen.

More elaborate methods of screening have used fluorescence or color changes of substrates to screen for catalysts and optimize variables in chemical reactions. In *High-Throughput Screening of Heterogeneous Catalysts by Laser-Induced Fluorescence Imaging*, J. Am. Chem. Soc. (2000) 122: 7422, Hui Su and Edward S. Yeung use laser-induced resonance-enhanced fluorescence imaging (LIFI) as a screening method for heterogeneous catalysts for a reaction. This is a high throughput in situ screening method providing micrometer scale spatial resolution and millisecond temporal resolution. LIFI is only applicable to fluorescent species and appears to be most useful for reactions producing volatile products. This method cannot be directly employed for most reactions of interest to the organic chemist, as most reactants do not contain a fluorophore or lead to a fluorescence change.

In *A Fluorescence-Based Assay for High-Throughput Screening of Coupling Reactions. Application to Heck Chemistry*, J. Am. Chem. Soc.(1999) 121:2123, a screening procedure was followed whereby a substrate possessing an attached fluorophore was reacted with a second molecule that is attached to a solid support. Authors K. H. Shaughnessy et al. employed the fluorescence based screening method to discover new phosphines for Heck chemistry. An acrylate containing an attached coumarin was reacted with an aryl halide supported on a cross-linked polystyrene resin in the presence of a transition metal catalyst. The calorimetric assay was able to be conducted in a high throughput fashion and took significantly less time to conduct than the gas chromatography used by the authors to confirm that their fluorescence based technique was accurate in identifying the most active ligands for the Heck coupling of aryl bromides and chlorides. Thus, in most instances, the substrate for a reaction of interest will have to be modified by the installation of a chromophore in order to employ this method. Screening results obtained for this significantly modified substrate, often containing a highly conjugated appendage, will not necessarily be valid for more typical, non-fluorescent substrates. Of course, additional synthetic chemistry is also often required to synthesize requisite "chromophore-tagged" substrates.

In *Reactive Dyes as a Method for Rapid Screening of Homogeneous Catalysts*, (1998) J. Am. Chem. Soc. 120: 9971, Alan C. Cooper et al. describe the use of reactive dyes to assess the activity of various catalysts. Potential catalysts for alkene and imine hydrosilation were screened by modifying the substrates of the reactions by incorporation of reactive dyes, which are "bleached" or change color upon undergoing a catalytic reaction. There is, in fact, a significant change or alteration of the dye color due to the saturation of a reactive functionality which disrupts conjugation between an electron donating and an electron accepting functional group. The authors identify an inherent limitation in the procedure described in their article on page 9972 "The bleaching process indicates a change has taken place, such as loss of conjugation between A and D groups, but does not prove that hydrosilation is the cause." The authors confirmed that the color change was due to the hydrosilation of the dye by analyzing the dye through the use of a conventional reaction in which the hydrosilation of the dye was known to occur and analyzing the dye by NMR spectroscopy. However, in at least one case, a false positive was detected, wherein the presumed hydrosilylation product was, in fact, a hydrogenation product (*Pure Applied Chemistry* 2001, 73, 119–128). In *Discovery of Novel Catalysts for Allylic Alkylation with a Visual Colorimetric Assay*, Angew. Chem. Int. Ed., (1999) 38, 3163, Olivier Lavastre and James P. Morken describe a calorimetric technique for parallel analysis of catalysts for allylic alkylation. The technique utilizes the phenomenon that colorless 1-naphthol will undergo electrophilic aromatic substitution with a diazonium salt to give a bright red orange azo dye product. Thus, the release of 1-naphthol as an allylic leaving group can be followed by monitoring azo dye formation. Although active catalysts could be identified by simple visual inspection, parallel UV analysis was employed to assess catalysts possessing similar activity. These methods, too, though of utility, require substantial substrate alteration and assume that the results obtained for "chromophore-tagged" substrates will be valid for more typical substrates. The latter experiment has a further complication in that the diazonium salt itself is quite reactive toward nucleophiles and so, in this case, was actually added only after the allylic substitution reaction had taken place. For this technique to provide for a continuous assay of product formation versus time, reactions will have to be found that are compatible with the presence of diazonium salts.

The move from the more deliberate, traditional approach to catalyst discovery to combinatorial approaches, has spurred great interest in the development of parallel screening methods. As Crabtree recently put it, ideally one seeks "an appropriate chemical sensor in a rapid parallel assay to detect rate and perhaps selectivity." There is currently great interest in "combinatorial catalysis," especially that involving transition metal (TM) catalyzed reactions, for which reaction discovery and optimization often involve varying (i) the metal; (ii) the ligand (type, structure and stoichiometry) and (iii) the substrate structure.

The present invention overcomes some of the limitations possessed by the prior art processes. The process of the present invention provides for direct evidence of product or expected stoichiometric byproduct formation that is not available with some prior art techniques such as the IR thermography method. The present invention also provides for relative rate profiles that are not readily provided by time-point detection systems employing gas or liquid chromatography for product separation. Furthermore, the monitoring process of the present invention does not require altering the substrate by installing a chromophore or a fluorophore as fluorescence assays and calorimetric assays involve. Such alterations may be cumbersome and time-consuming and may lead to screening results that are not applicable to the actual (e.g., non-fluorescent) substrate of interest.

BRIEF SUMMARY OF THE INVENTION

The present invention is directed to a biphasic process for rapid screening of organic reactions by monitoring relative rates of parallel organic reactions and, in some cases, determining the enantiomeric ratio of the product, as well. The screening process is suitable to determine the efficacy of different reactants, process conditions, and process enhancers such as catalysts or promoters. The biphasic process also allows multiple samples to be analyzed/monitored simultaneously. Parallel reactions involving either enantiomeric catalysts or reporting enzymes with opposite enantiop references and simultaneous analysis allow the enantioselectivity of appropriate organic reactions to be easily determined. The monitoring is done in situ and thus removal of aliquots for separate testing is unnecessary.

The biphasic process begins with a reaction in an organic solvent layer to produce a product, and possibly a byproduct. The product and/or byproduct diffuse from the organic solvent layer into an adjacent aqueous solvent layer. Once in the aqueous solvent layer, the product or byproduct serves as an enzymatic substrate for a reaction or sequence of reactions to produce a spectroscopic change.

This spectroscopic change typically corresponds to the product/byproduct-dependent formation or consumption of an enzymatic co-substrate or cofactor, itself having a significant extinction coefficient in the UV/visible range. The UV-observable enzymatic co-substrate or cofactor may be formed in the same enzymatic reaction in which the organic product/byproduct is consumed. However, it may also be formed in a subsequent enzymatic reaction that is chemically linked to the enzymatic reaction involving the organic product/byproduct. Further, it may be formed in a non-enzymatic chemical reaction that is linked to the enzymatic reaction involving the initial (by)product (e.g. carbonic anhydrase/aminomethyl anthracene couple for $CO_2$ or alcohol oxidase/chemical luminescence couple for alcohols. Spectroscopic changes are monitored for organic reactions run in parallel to determine relative rates at which the product is formed in the organic solvent layer. The spectroscopic change is usually the production or consumption of a spectroscopically observable compound. A spectrophotometer may be used to monitor the spectroscopic change. UV or visible light is transmitted through the aqueous solvent layer.

The process of the present invention can be used to optimize conditions for any organic reaction provided that the organic reaction produces a product and/or byproduct that can diffuse to the aqueous solvent layer and serve as an enzymatic substrate to ultimately produce a spectroscopically observable effect. Such products and/or byproducts include, but are not limited to, alcohols, acetate, butyrate, amines, 1,2-diols, beta-amino alcohols, carbon dioxide, sulfate esters and phosphate esters.

Suitable reactions which can be evaluated using the process of the present invention include, but are not limited to: allylic substitution reactions; acetyl substitution reactions; glycoside activation reactions; Hetero-Diels Alder reactions; retrocheleotropic elimination of $CO_2$; decarboxylation reactions; dihydroxylation reactions; diamination reactions; aminohydroxylation reactions; epoxide hydrolysis; C—X bond formation via epoxide opening; nuclephilic addition to carbonyls; additions of nucleophiles to iminium ions; acylation reactions; phosphorylation reactions; and ester deprotection reactions.

It is therefore an object of the present invention to provide a sensitive process for monitoring relative rates for an organic reaction to be optimized by the systemic alteration of one or more variables in parallel. This process monitors a series of organic reactions in parallel to provide relative rate profiles. Further, the process does not require altering the reactants of the organic reaction, as the actual organic product and/or byproduct is chemically linked to the formation/consumption of a spectroscopically observable enzymatic co-substrate or cofactor, or is linked, through an enzymatic reaction, to pH-dependent fluorescence change (for $CO_2$ for example) or to a chemiluminescent signal (for alcohol oxidase or amine oxidase couples, for example).

Other objects and advantages of the present invention will be in part apparent to one of ordinary skill in the art and in part pointed out hereinafter.

DETAILED DESCRIPTION OF THE INVENTION

Figure 1:
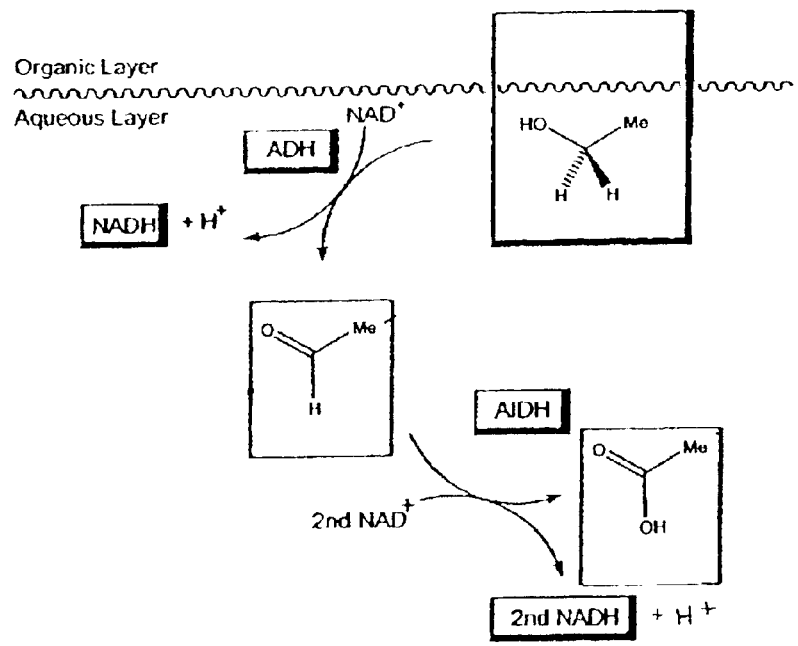
FIG. 1 depicts ethanol diffusion from the organic solvent layer to the aqueous solvent layer and then the conversion of the ethanol into acetaldehyde by alcohol dehydrogenase using an enzyme/coenzyme couple.

In accordance with the invention, the organic reaction under study is coupled, in situ, to an enzymatic reaction that permits continuous UV-monitoring of the reaction. This approach, termed in situ enzymatic screening (ISES), provides for (i) evidence of product formation (not directly available using the IR thermography method) and (ii) relative rate profiles (not easily available with time-point detection systems employing gas or liquid chromatography or mass spectrometry), (iii) without the need to alter the substrate, by installing a chromophore, a fluorophore, or an azo-dye precursor.

The biphasic process is used to monitor the rate or product yield of an organic reaction. Biphasic means that two phases are present. The two phases are an organic solvent layer, and adjacent thereto, an aqueous solvent layer. The organic solvent layer can be less dense than (i.e., above) the aqueous solvent layer or more dense than (i.e., below) the aqueous solvent layer. The organic solvent layer is used as the media in which the organic reaction is performed. The product or byproduct formed diffuses into the aqueous solvent layer. The aqueous solvent layer is then used as the media in which the product or by-product formed in the organic solvent layer is ultimately measured.

Organic Solvent Layer

The organic solvent layer is composed of an organic solvent or mixture of organic solvents. The organic solvent layer is preferably substantially immiscible with the aqueous solvent layer. The organic solvent or solvents preferably substantially solubilize the selected organic substrates and catalysts. The organic solvent or solvents also preferably permit the diffusion of the product or byproduct into the aqueous solvent layer. Finally, the organic solvent or solvents may be inert to, or promote, the organic reaction under study. For example, in the case of an allylic displacement reaction, the organic solvent may promote the allylic displacement reaction, possibly even by ligating to the metal if a transition metal catalyst were utilized in the reaction.

The selection of the appropriate solvent or mixture of solvents according to these criteria will vary depending on the type of organic reaction being monitored.

Examples of suitable solvents include, but are not limited to, hexane, benzene, cyclohexane, pentane, heptane, 1,2-dimethylmethoxyethane, dioxane, 1,2-dichloroethane, 1,2,3,4-tetrachloroethane, tetrahydrofuran, toluene, carbon tetrachloride, chloroform, ethyl acetate, methyl t-butyl ether, methylene chloride, and diethyl ether. Examples of suitable mixtures include, but are not limited to, a mixture of tetrahydrofuran and toluene and a mixture of tetrahydrofuran, hexane, and toluene.

Organic Reaction and Starting Materials

Depending on the type of organic reaction involved, the starting material can be introduced into the organic solvent layer before the other reagents involved in the organic reaction, after the other reagents involved in the reaction, or even at the same time as the other reagents involved in the organic reaction. The appropriate order of addition will depend upon the nature of the organic reaction being utilized with the process.

Any type of organic reaction can be used with the process of this invention, provided that the organic reaction produces a product or byproduct that can diffuse to the aqueous solvent layer to react with an enzyme or enzyme couple contained therein. The starting material is reacted such that a product and often, a stoichiometric byproduct are produced. The product of the organic reaction under study generally involves formation or cleavage of at least one O—C, N—C, S—C, C—C, O—P, N—P or X—C bond, where X is a halogen.

Catalysts and Promotors

The organic reaction can be facilitated by a catalyst or promotor and the efficacy of the catalyst or promotor can be determined using the biphasic process. As used herein, catalyst describes a reagent that accelerates the reaction under study, is present at a substoichiometric amount, and is regenerated by the reaction rather than being consumed by it. As used herein, promotor describes a reagent that accelerates the reaction under study, whether it be present at substoichiometric amounts, stoichiometric amounts, or superstoichiometric amounts. The promotor does not need to be regenerated. Thus, a promotor, in contrast to a catalyst, can be present in any amount and can be consumed by the reaction.

Any type of promotor or catalyst for use with the organic reaction under study can be evaluated in the process of the invention. Examples of catalysts or promotors include metal-ligand complexes. These metal catalysts exist as a metal with one or more ligands complexed to the metal. The metal may be any of the main group metals, alkali metals, alkaline earths, transition metals, lanthamides or actinides. One such type of metal-ligand complex is a transition metal catalyst, which also typically exists as a complex of a transition metal with one or more ligands complexed to the transition metal. The transition metal in the transition metal catalyst may be an early or late transition metal in high, low or zero oxidation states, for example, Ni, Mo, Pt, Co, Ru, Os, Rh, Ir, Mn, Re, V, Nb, Ta, Cr, W, Ag, Fe, Cu, Au, and Pd. The ligand complexed to the metal may be composed of or derived from chiral or achiral forms of cyclopentadienyl anions, amino esters, oxazolidinones, hydroxy acids, hydroxy esters, hydroxy amides, pyridines, fused pyridines, nitrogen heterocycles, oxazolines, oxazoles, imidazoles, pyrroles, crown ethers, cryptands, carcerands, phosphines, diphosphines, polyphosphines, quinuclidines, quinines, alkaloids, dextrins, cyclodextrins, salens, porphrins, biaryls, sulfonamides, Schiff bases, alcohols, diols, polyols, amines, diamines, polyamines, peptides, proteins, nucleic acids, etc. The ligands contain a coordinating atom, which coordinates to the metal or transition metal of the catalyst. The coordinating atom is typically P, N, O, C or As, but may also be S, Se, Te, or Sb.

Catalysts or promoters can also be Lewis acids or electron pair acceptors. Both metallic and non-metallic Lewis acids are known. Typical Lewis acids include zinc chloride, scandium triflate, boron trifluoride etherate, trialkyl silyl sulfonates, aluminum trichloride, magnesium bromide, lithium perchlorate, copper chloride and mercury cyanide.

There are some reactions, such as acylation and phosphorylation, in which the reactions may be accelerated by both Lewis acidic and nucleophilic promoters. It may be desirable to use the process of the invention to investigate the effects of two promotor classes simultaneously upon a reaction under study.

Catalysts and promoters may also be in the form of metals and ligands, which are not necessarily in a complex. In such catalysts or promoters the organic ligand speeds up the reaction catalyzed by the metal, which may be in the reaction solution. Examples of the organic ligands include, but are not limited to, chiral or achiral forms of cyclopentadienes, amino esters, oxazolidines, hydroxy acids, hydroxy esters, hydroxy amides, pyridines, fused pyridines, nitrogen heterocycles, oxazoles, imidazoles, pyrroles, crown ethers, cryptands, carcerands, phosphines, diphosphines, polyphosphines, quinnuclidines, quinines, alkaloids, dextrins, cyclodextrins, salens, porphyrins, biaryls, sulfonamides, Schiff bases, metallocenes, monools, diols, polyols, amines, diamines, polyamines, ammonium salts, peptides, proteins, nucleic acids, etc.
Product or Byproduct Regardless of the type of organic reaction under study, a product and often a byproduct are produced or capable of being produced. The product and/or byproduct should be capable of diffusing from the organic solvent layer to the aqueous solvent layer so that it may serve as an enzymatic substrate for an enzyme/coenzyme couple solubilized therein.

Examples of byproducts include, but are not limited to, alcohols, amines, carboxylates (e.g., acetate or butyrate), sulfates, phosphates, and carbon dioxide. The alcohol can be ethanol, methanol, propanol, butanol or another alcohol. For instance, the alcohol byproduct may be ethanol if a dehydrogenase couple is desired or methanol if an alcohol oxidase/peroxidase couple is desired. Preferably, the alcohol byproduct is ethanol. The sulfate byproduct can be sulfate itself or a suitable monoester. The phosphate byproduct can be a phosphate itself or a phosphate mono-, or di-ester.
Diffusion from Organic Solvent Layer to Aqueous Solvent Layer Preferably, the product and/or byproduct and composition of the organic solvent layer and aqueous solvent layer are selected such that the product and/or byproduct diffuses from the organic solvent layer to the aqueous solvent layer sufficiently to obtain meaningful relative kinetic data to be obtained within 10 minutes. This allows an accurate correlation to be made between the rates of production (or consumption) of a spectroscopically observable compound in the aqueous layers being monitored and the relative rates of product formation in the organic layers.
The Aqueous Solvent Layer The aqueous solvent layer is the medium in which an observable compound is formed/consumed. This is achieved by enzymatic reaction of the product or byproduct, which has diffused from the organic solvent layer.

Criteria used in selecting the appropriate composition of the aqueous solvent layer may be similar to that for selecting the organic solvent layer. For instance, preferably the aqueous solvent layer is substantially immiscible in the organic solvent layer, and permits the diffusion of the byproduct from the organic solvent layer into the aqueous solvent layer. Preferably the aqueous solvent layer substantially solubilizes the enzyme and enzyme couple utilized in the process of the present invention. Finally, preferably the aqueous solvent layer promotes the reaction of the enzyme or enzyme couple utilized in the process of the present invention to produce the observable signal.

The aqueous solvent layer may include a buffer, for example to obtain a pH level of the buffered aqueous layer to promote the diffusion of the organic product/byproduct (e.g., if ionizable) and/or to promote the enzymatic reaction(s) to provide a spectroscopic observable. Examples of suitable buffers include, but are not limited to, pyrophosphate, phosphate, TRIS, imidazole, MOPS, MES, acetate, borate, triethanolamine, HEPES, glycine, BICINE, and TRICENE. It is preferred that a phosphate, a pyrophosphate, or acetate buffer not be utilized when these compounds are actual chemical intermediates in the reactions being employed. Thus, for example, in the later described process of the present invention in which the ADH/NAD$^+$ and AlDH/NAD$^+$ enzyme/coenzyme couple is employed, a pyrophosphate buffer can be used in the aqueous solvent layer. The pyrophosphate buffer is compatible with the enzymes and cofactors in this couple. Furthermore, in this case, a basic pH drives both oxidative equilibria toward products. This is because three acidic protons are produced in the overall four-electron oxidation of EtOH to acetic acid by NAD(P)$^+$.
Observable Compounds and Measurement of the Results The relative amounts of the observable compound produced in the aqueous solvent layer through the enzymatic reaction of the product or byproduct may be used to determine the relative amounts of product formed in the organic solvent layers. The amount of the observable compound may be also be monitored at time intervals to determine the rate of product formation in the organic solvent layer. For several organic reactions run in parallel, the relative rates of formation may be determined to compare, for example, different catalysts. For each of the catalysts or promoters being screened, by running parallel screens with enzyme couples of opposite enantioselectivity, or by running parallel screens with enantiomeric catalysts or promoters and a single, enantioselective enzyme couple, the enantioselectivities of the reactions under study may be determined.

The observable compound is capable of absorbing radiation of a certain wavelength. It may also emit radiation via fluorescence. The compound can be monitored visually or spectrophotometrically. Spectrophotometric monitoring is done by the method of absorption detection, typically using a UV/visible spectrophotometer.

The spectroscopically observable compound can be any compound capable of absorbing electromagnetic radiation that can be incorporated into or coupled with an enzyme/coenzyme couple such that a spectroscopically observable event occurs which can be correlated with the behavior of the organic reaction in the organic solvent layer. Typically, the spectroscopically observable compound is a direct participant in the enzyme/coenzyme couple; however, the present invention is not limited to enzyme/coenzyme couples in which the spectroscopically observable compound is a direct participant in the enzyme/coenzyme couple.

The spectroscopically observable event is correlated to the behavior of an organic reaction; thus, the spectroscopically observable event reflects the progress (or lack thereof) of the organic reaction under study. In assessing the efficacy of various reaction conditions, including catalysts and protecting groups for the reagents of a particular organic reaction, parallel reactions are screened and the spectroscopically observable event is able to accurately reflect relative rates of the particular reaction under study. The spectroscopically observable compound is capable of absorbing electromagnetic radiation of a certain wavelength or range of wavelengths. Typically, the spectroscopically observable compound will be a compound that is capable of absorbing electromagnetic radiation in the UV range of wavelengths, such as the cofactors NADH and NAD(P)H. However, the method of the present invention also includes other compounds capable of absorbing electromagnetic radiation in other regions of the electromagnetic spectrum, especially electromagnetic radiation having wavelengths in the visible light region, wavelengths of 400 nm to 700 nm, and wavelengths in the infrared range, wavelengths of 700 nm to 20,000 nm.

Preferably, the spectroscopically observable compound is a coenzyme or cofactor.

Examples include NAD(P)H and NAD(P)H analogues, including the reduced forms of: (i) 3-acetylpyridine adenine dinucleotide (APAD; $\lambda_{max}$=363 nm); (ii) 3-formylpyridine adenine dinucleotide ($\lambda_{max}$=358 nm); (iii) thiononicotinamide adenine dinucleotide ("thio-NADH") ($\lambda_{max}$=395 nm); and (iv) 3-aminopyridine adenine dinucleotide ($\lambda_{max}$=330 nm). For other enzyme couples, the spectroscopically observable molecule might be a member of a different cofactor family, such as the riboflavin family, or it might be a dye that serves as a cofactor for an enzyme in the couple (such as in the alcohol oxidase/peroxidase couple).

An example of the generation of a spectroscopically observable compound is what occurs with the NAD(P)$^+$/alcohol dehydrogenase and NAD(P)$^+$/aldehyde dehydrogenase enzyme/coenzyme couple for an ethanol byproduct, as is shown in FIG. 1. The spectroscopically observable event can also be the consumption of a spectroscopically observable compound, for example, the consumption of NAD(P)H in the acetate kinase/ATP and pyruvate kinase/PEP and lactate dehydrogenase/NAD(P)H enzyme couple for an acetate byproduct. Such an event may be monitored by the concomitant change in absorbance at a fixed wavelength in the vicinity of 340 nm, a $\lambda_{max}$ value for NAD(P)H.

Concentration of Observable Compounds

The concentration of the spectroscopically observable compound in the aqueous layer can be any concentration that enables the detection of the spectroscopically observable compound. The concentration will depend to a degree upon the rate of diffusion of the product or byproduct from the organic solvent layer to the aqueous solvent layer. The upper and lower limits are set by the sensitivity and capabilities of the spectrometer that is being used to detect the spectroscopically observable compound. For example, diffusion of only a small fraction of the product or byproduct mau suffice such as 1 part in 100, 1000, or 10000, for enzymatic detection.

For enzymatic couples in which NAD(P)H is ultimately oxidized to NAD(P)+, and in which UV absorbance is the spectroscopic observable being monitored, initial NAD(P)H concentrations $\leq$400 micromolar are used to insure that the initial absorbance reading is <2.5 at 340 nm, in a cell of 1 cm path length. Concentrations of the byproduct in the aqueous layer of $\geq$10 micromolar, leading to an absorbance change of $\geq$0.06 at 340 nm in a cuvet with a 1 cm path length, where $\in_{340}$ (NADH)=6220 M$^{-1}$cm$^{-1}$] are ideal. An absorbance change of this magnitude is easily detected in 10 min. However, lower concentrations, down to 1 micromolar (absorbance decrease of $\geq$0.006), are detectable provided that the spectrophotometer has a reasonably good baseline.

Electromagnetic Radiation Wavelength and Sources

The electromagnetic radiation source comprises or consists essentially of a wavelength in the range from about 180 to about 1500 nm. The electromagnetic radiation used in the invention typically has wavelengths ranging from about 260 nm to about 420 nm. Preferably, the electromagnetic radiation in the invention has wavelengths ranging from about 280 nm to about 410 nm.

The electromagnetic radiation source is typically any type of light source that is used in spectrophotometers. Examples of suitable electromagnetic radiation sources include, but are not limited to, mercury (for ultraviolet light absorption), tungsten (for visible light absorption), iodine (for UV light absorption), zinc (for UV light absorption), cadmium (for UV light absorption), xenon (for UV light absorption), deuterium (for UV light absorption), and the like. Preferably, the electromagnetic radiation source comprises or consists essentially of a wavelength of radiation that will be absorbed by the spectroscopically observable compound, the absorption of which is to be detected. Generally, the electromagnetic radiation source provides electromagnetic radiation impinging on the container orthogonal to the plane of the containers if the embodiment of the invention involves a series of organic reactions run in parallel or if the embodiment of the invention involves the monitoring of a single organic reaction.

Detection Means

The detection means can comprise any suitable means for detecting absorption. Preferably, the detector is positioned in line with the container and the light source. Preferably, the detector is positioned and shielded appropriately such that stray light does not impinge upon it. Therefore, the light reaching the detection means is substantially only that which is transmitted through the reaction vessels being monitored. This positioning of the detector maximizes intensity in the light output from the container and therefore maximizes sensitivity. The detector means is also desirably fixed in position to eliminate detection inaccuracies. A preferred radiation source and the detector are those found in a UV/visible spectrophotometer. A preferred type of spectrophotometer is a Shimadzu UV-2101PC spectrophotometer equipped with a CPS-260 six-cell positioner with thermoelectric temperature control that enable the temperature to be controlled during the process.

Apparatus for Evaluation of the Reaction Rates and Products using Absorption of Radiation In general, the containers used to contain the biphasic system should have smooth surfaces and uniformly thick walls and be made of a material that is penetrable over the range of wavelengths of radiation absorbed by the absorbable compound, the absorbance of which is to be detected or measured. Preferred materials for containers include, but are not limited to, quartz, fused silica and glass. The wall of the container should be of sufficient thickness so as to maintain the structural integrity of the container, yet not so thick as to adversely impede the passage of the radiation through the container. The shape of the container also is not critical to the present inventive process. The container can have any suitable shape. Furthermore, the appropriate size of the container will depend on the scale at which the particular reaction is run. A quartz cuvet is a preferred container for use in the process of the present invention. The path length of the container is important as this is directly proportional to the magnitude of absorbance detected. Ideally, the minimum path length will be chosen consonant with the sensitivity required in the assays and the capabilities of the spectrophotometer.

Preferably, the interface of the aqueous solvent layer and the organic solvent layer is well-spaced from the beam. For example, for a quartz cuvet the following procedure can be followed to establish an appropriate position for the interface of the aqueous solvent layer and the organic solvent layer. The cuvet can be entirely filled with the standard aqueous solution of NAD(P)H and the $Abs_{340}$ can be measured to establish a baseline value for the absorbance. This value can then be compared to values for the same aqueous solvent layer solution at various partially filled cuvet volumes. The remaining volume can be filled either with air or with an immiscible organic solvent. When a lower than expected absorbance value is detected at a particular cuvet volume, or a noisy signal is obtained, it can be reasoned that the spectrophotometer beam is passing through the cuvet near or above the air-buffer interface. When the expected absorbance value is observed for a particular cuvet volume it can be presumed that the spectrophotometer beam is passing squarely through the aqueous solvent layer solution. Preferably, to ensure that the interface of the aqueous solvent layer and the organic solvent layer is sufficiently well-spaced from the spectrophotometer beam, a larger volume than that at which the expected baseline value was observed should be used. Thus, for a quartz cuvet with a 1 cm light path and a nominal one mL volume (Actual filled volume=1.6 mL) a 900 $\mu$L aqueous layer can be used to ensure adequate spacing from the interface. For both conservation of reactants and reagents, and for higher throughput application of the present invention, smaller volumes may be desirable. Thus, incorporation of a large number of reaction vessels will likely be associated with miniaturization of the vessels and with automation of the vessel loading operations.

Fluorescence Plate Reader

A fluorescence plate reader or gel reader may also be used to determine the amount of observable compound. Typically, "gel readers" (or "gel-illuminators" or "gel documentation systems") illuminate at both long and short wavelengths. One commercial instrument has a long wavelength illumination at 365 nm. This is acceptable for NADH. These "readers" then record fluorescence emission across a broad range of wavelengths. NADH fluoresces at 470 nm and this emission is nicely captured as a snapshot by the gel reader.

The plate contains a multitude of wells, typically 96. Similarly, a vial holder may be used, with any convenient number of rows in each dimension (e.g. 10×10 allows for the simultaneous screening of all ten combinations of ten potential nucleophilic catalysts and 10 potential Lewis acid catalysts, as would be desirable in the example given below). The reader may read from the top or the bottom of the wells. If it reads from the bottom, the aqueous solvent layer should be more dense than the organic solvent layer. If it reads from the top, the aqueous solvent layer should be less dense than the organic solvent layer.

For example, a top reader may be used to screen combinatorially catalysts for the acylation of 1-phenylethanol with diethylpyrocarbonate $\{EtO_2C(O)CO_2Et\}$ in methylene chloride (or other "lower" organic layers such as $CHCl_3$, $CCl_4$, etc.) The acylation reaction produces an ethyl carbonate ester of the alcohol, along with a molecule of $CO_2$ and one of EtOH. The EtOH very easily diffuses up into an upper aqueous layer where it is oxidized to acetic acid with an ADH/AlDH couple. This produces NADH whose fluorescence is effectively visualized with a fluorescence plate reader with an upper "long wave" emission lamp (emits at about 365 nm) and an overhead CCD recorder.

Large arrays of reaction wells can be screened in parallel, in this manner. By using chiral catalysts, and dedicating half of the wells in a 100 well array to one enantiomer of the alcohol and half to the other, one could also screen, for example, for enantioselective acylation catalysts that would permit for the kinetic resolution of the alcohol.

Process Conditions

The process of the invention can be carried out at ambient temperature, such as from around 20 degrees Celsius to about 35 degrees Celsius, or as low as 0 degrees Celsius or as high as 50 degrees Celsius. However, if the method employs a spectrophotometer as the detection means, spectrophotometer preferably has its own cooler for operation at sub-zero temperatures, such as from about 0 degrees Celsius to about –10 degrees Celsius. Typically, the method of the present invention is carried out at a temperature between about 20 degrees Celsius and about 37 degrees Celsius.

Reactions in the Aqueous Solvent Layer

Various types of enzyme/coenzyme couples can be employed in the aqueous solvent layer of the biphasic system. The product and/or byproduct of the organic reaction will determine what type of enzyme/coenzyme couples can be used in the aqueous solvent layer. The selection of appropriate enzymes and coenzymes as well as the corresponding type and amount of buffer for the aqueous solvent layer is well within the skill of one of ordinary skill in the art.

1) Ethanol Byproduct

When the byproduct is ethanol, an enzyme/coenzyme couple can be alcohol dehydrogenase/$NAD^+$ and aldehyde dehydrogenase/$NAD^+$. FIG. 1 shows the enzyme/coenzyme couple using ethanol. Ethanol diffuses from the organic solvent layer to the aqueous solvent layer. Once in the aqueous solvent layer, ethanol is converted to acetaldehyde by alcohol dehydrogenase. In the process, one molecule of NAD(P)+ cofactor is reduced to NAD(P)H. In the second step of this enzyme/coenzyme couple the acetaldehyde is converted to acetic acid by aldehyde dehydrogenase. In this process, a second molecule of NAD(P)+ is reduced to NAD(P)H.

2) Acetate Byproduct

When the byproduct of the organic reaction is acetate, one type of enzyme/coenzyme couple that can be employed involves (i) ATP-dependent acetate kinase with ATP as cosubstrate, (ii) pyruvate kinase with PEP as cosubstrate, and (iii) lactate dehydrogenase with NADH or NADPH as cofactor. Scheme 1A shows the first enzyme/coenzyme couple for monitoring acetate.

Scheme 1A

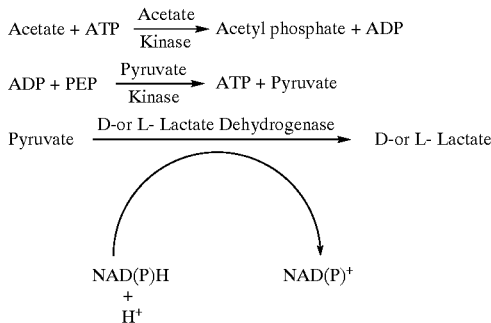

The acetate diffuses from the organic solvent layer to the aqueous solvent layer. Once in the aqueous solvent layer, the acetate is processed to acetyl phosphate through acetate kinase. Concomitantly, ATP is converted to ADP. ADP then serves as a substrate for the second enzyme in the couple. Namely, pyruvate kinase catalyzes the transfer of phosphoryl group from phosphoenol pyruvate to ADP to generate pyruvate and regenerate ATP for the first step of the couple. In step (iii) of the enzyme/coenzyme couple, pyruvate is reduced with NAD(P)H via lactate dehydrogenase to yield NAD(P)+ and lactate. An example of a suitable acetate kinase is that enzyme having Enzyme Commission Number 2.7.2.1.

The spectroscopically observable event with this enzyme/coenzyme couple is the decrease of either the NADH or the NADPH signal. Specifically, the decrease of either the NADH or the NADPH signal over time is measured.

There are two types of lactate dehydrogenase that can be employed in step (iii) of this enzyme/coenzyme couple, L-lactate dehydrogenase, D-lactate dehydrogenase, each of which employs NADH as a reducing agent. The two enzymes differ in producing opposite enantiomers of lactate from pyruvate. Any suitable buffer can be employed with this type of enzyme/coenzyme couple. The pH of the aqueous solvent layer in which the enzyme/coenzyme couple is operating can range from 6.5 to 8.5. Preferably, the pH of the aqueous solvent layer ranges from 7 to 8.5. Furthermore, the presence of magnesium chloride greatly facilitates the functioning of this acetate enzyme/coenzyme couple, as the enzyme acetate kinase is believed to use the $Mg^{2+}$ complex of ATP as its substrate.

Other stoichiometric carboxylate leaving groups (i.e., byproducts) can be monitored by similar enzyme couples. For example, for a butyrate leaving group, simple substitution of butyrate kinase for acetate kinase in the aforementioned couple yields a viable three enzyme assay (see Scheme 1B)

Scheme 1B

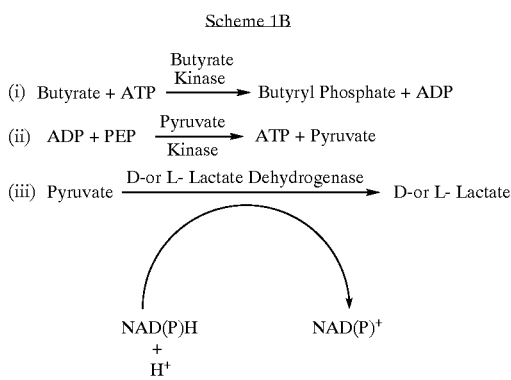

An example of a suitable butyrate kinase is the enzyme having Enzyme Commission Number 2.7.2.7. Step (ii) of Scheme 1B is the same as that of Scheme 1A; pyruvate kinase acts upon ADP and PEP to form ATP and pyruvate. Step (iii) is also the same as in Scheme 1A; lactate dehydrogenase facilitates the formation of lactate from pyruvate.

Either of the two types of lactate dehydrogenase, L-lactate dehydrogenase and D-lactate dehydrogenase, can also be employed in step 3 of the enzyme/coenzyme couple employing butyrate kinase. Any suitable buffer can be employed with this type of enzyme/coenzyme couple. The pH of the aqueous solvent layer in which the enzyme/coenzyme couple is operating can range from 6.5 to 8.5. Preferably, the pH of the aqueous solvent layer ranges from 7 to 8.5; this pH range allows optimal functioning of the enzymes and coenzymes of this enzyme/coenzyme couple. The enzyme/coenzyme couples shown in Schemes 1A and 1B for acetate and butyrate could also be employed for other carboxylate byproducts, with appropriate modifications in the kinase enzyme employed and conditions of the aqueous solvent layer.

A second kind of enzyme/coenzyme couple for the acetate byproduct can be employed in the present invention. This enzyme/coenzyme couple operates as shown below in Scheme 2.

Scheme 2

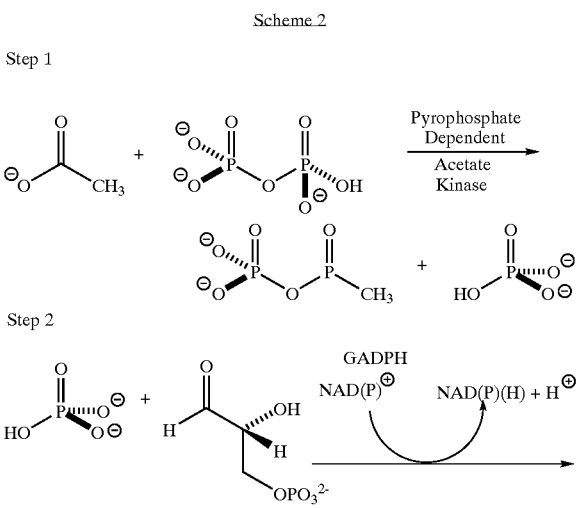

-continued

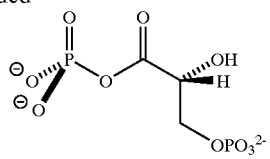

In step 1, pyrophosphate dependent acetate kinase acts to convert acetate to acetyl-phosphate, thereby releasing a molecule of inorganic phosphate from the pyrophosphate co-substrate. Step 2 is an oxidative phosphorylation in which glyceraldehyde 3-phosphate and inorganic phosphate are converted to 1,3-diphosphoglycerate through the action of glyceraldehyde 3-phosphate dehydrogenase and a nicotinamide co enzyme. This coenzyme can be NAD$^+$ or NADP$^+$.

A suitable pyrophosphate-dependent acetate kinase enzyme for this couple carries Enzyme Commission Number 2.7.2.12. Suitable glyceraldehyde 3-phosphate dehydrogenase enzymes include those with Enzyme Commission Number 1.2.1.11 (NAD$^+$-dependent) and Enzyme Commission Number 1.2.1.12 (NADP$^+$-dependent). Furthermore, it is expected that dehydrogenase enzymes can be found for the enzyme/coenzyme couple that will work with both NAD$^+$ and NADP$^+$ cofactors. The selection of appropriate enzymes and coenzymes is readily made by one of ordinary skill in the art. Any suitable buffer can be employed with this type of enzyme/coenzyme couple. However, a phosphate buffer is not suitable for this couple, as it is a product of the first enzymatic step. The pH of the aqueous solvent layer in which the enzyme/coenzyme couple is operating can generally range from about 6.5 to about 8.5. The preferred pH of the aqueous solvent layer for this particular acetate kinase enzyme/coenzyme couple will depend on the pH at which the particular enzymes and coenzymes selected for the enzyme/coenzyme couple optimally function. The selection of the appropriate amount and type of buffer is readily made by one of ordinary skill in the art.

3) Sulfate Byproduct

Another kind of enzyme/coenzyme couple is an enzyme/coenzyme couple employing sulfatase. The first sulfate enzyme/coenzyme couple is shown in Scheme 3A. A sulfatase enzyme will facilitate the hydrolysis of a sulfate monoester to form an alcohol and sulfate. Suitable sulfatase enzymes include, but are not limited to, Enzyme Commission Number 3.1.6.2 and Enzyme Commission Number 3.1.6.1. The sulfate then serves as the substrate for step 2 wherein ATP and ATP sulfurylase facilitate the formation of adenylyl sulfate and pyrophosphate. Pyrophosphate then serves as the substrate for step 3 in which a molecule of water and a molecule of pyrophosphate form two molecules of inorganic phosphate, with the assistance of pyrophosphatase. An example of a suitable pyrophosphatase enzyme includes Enzyme Commission Number 3.6.1.1. In step 4 of the first sulfate enzyme/coenzyme couple, two molecules of glyceraldehyde 3-phosphate are converted to 2 molecules of 1,3-diphosphoglycerate by glyceraldehyde 3-phosphate dehydrogenase. In conjunction with this phosphorylation, 2 molecules of NADP$^+$ are converted to two molecules of NADPH or 2 molecules of NAD$^+$ are converted to 2 molecules of NADH. The particular type of glyceraldehyde 3-phosphate dehydrogenase that is chosen will depend on whether NAD$^+$ is being converted to NADH or NADP$^+$ is being converted to NADPH. Thus, an example of a suitable glyceraldehyde 3-phosphate dehydrogenase for the use of NAD$^+$ would be Enzyme Commission Number 1.2.1.11. Similarly, an example of a suitable glyceraldehyde 3-phosphate dehydrogenase for the use of NADP$^+$ would be Enzyme Commission Number 1.2.1.12. The selection of appropriate enzymes and coenzymes as well as the corresponding conditions for their optimal functioning in the aqueous solvent layer is well within the skill of one of ordinary skill in the art. Any suitable buffer can be employed with this type of enzyme/coenzyme couple; however, neither a pyrophosphate nor a phosphate buffer is suitable for the sulfate enzyme/coenzyme couple shown in Scheme 3A. The pH of the aqueous solvent layer in which the enzyme/coenzyme couple is operating can generally range from about 6.5 to about 8.5. The preferred pH of the aqueous solvent layer for this particular sulfate enzyme/coenzyme couple will depend on the pH at which the particular enzymes and coenzymes selected for the enzyme/coenzyme couple optimally function. The selection of the appropriate amount and type of buffer is readily made by one of ordinary skill in the art.

Scheme 3A

Step 1

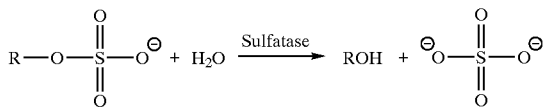

Step 2

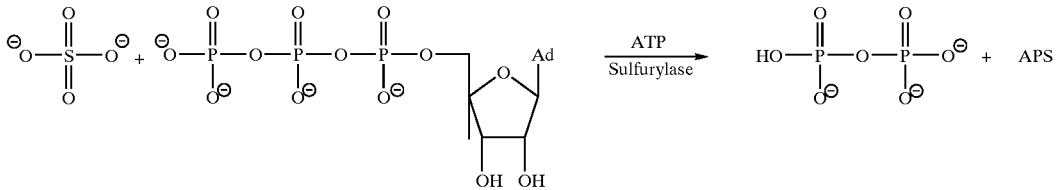

Step 3

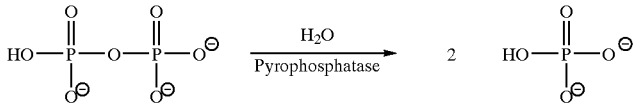

Step 4

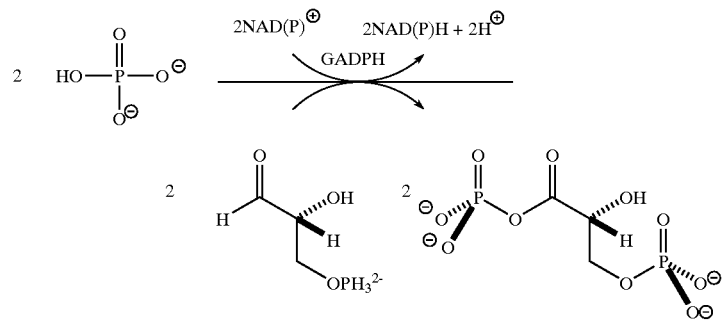

wherein R is $C_{6-12}$, more preferably $C_{6-9}$. R can be alkyl, alkenyl, alkynyl, acyl, aryl, heteroaryl, substituted alkyl, substituted alkenyl, substituted alkynyl, substituted acyl, substituted aryl and substituted heteroaryl.

Scheme 3B below shows the overall reaction equation for the first sulfate enzyme/coenzyme couple. The formation of NADH is monitored spectroscopically in the aqueous solvent layer. The number of steps in this sulfate enzyme/coenzyme couple may depend on the nature of the sulfate byproduct produced by the organic reaction in the organic solvent layer. Scheme 3A above shows the steps involved where the byproduct is a sulfate monoester. The first step of Scheme 3A involves the hydrolysis of a sulfate monoester to produce sulfate. If the byproduct of the organic reaction in the organic solvent layer were simply a sulfate ion, then the first step employing sulfatase would not be necessary and only three enzymes would be utilized in the enzyme/coenzyme couple. Thus, if the byproduct of the organic reaction in the organic solvent layer were simply a sulfate ion, the enzyme/coenzyme couple would consist of (i) ATP sulfurylase and ATP; (ii) pyrophosphatase; and, (iii) GAPDH with NAD(P)$^+$, and glyceraldehyde 3-phosphate.

Scheme 3B

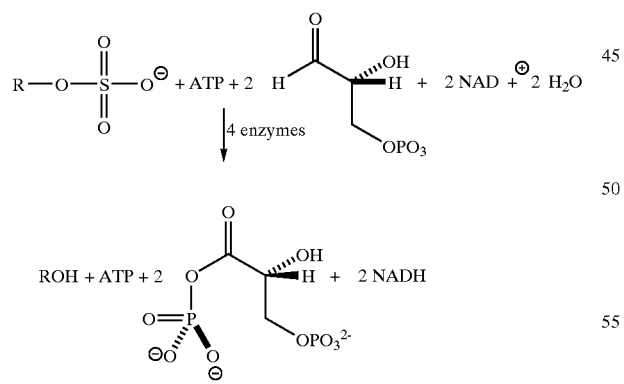

wherein R is $C_{6-12}$, more preferably $C_{6-9}$. R can be alkyl, alkenyl, alkynyl, acyl, aryl, heteroaryl, substituted alkyl, substituted alkenyl, substituted alkynyl, substituted acyl, substituted aryl and substituted heteroaryl.

A second kind of enzyme/coenzyme couple for a sulfate byproduct may be employed in the present invention. This enzyme/coenzyme couple operates as shown below in Scheme 4.

Scheme 4

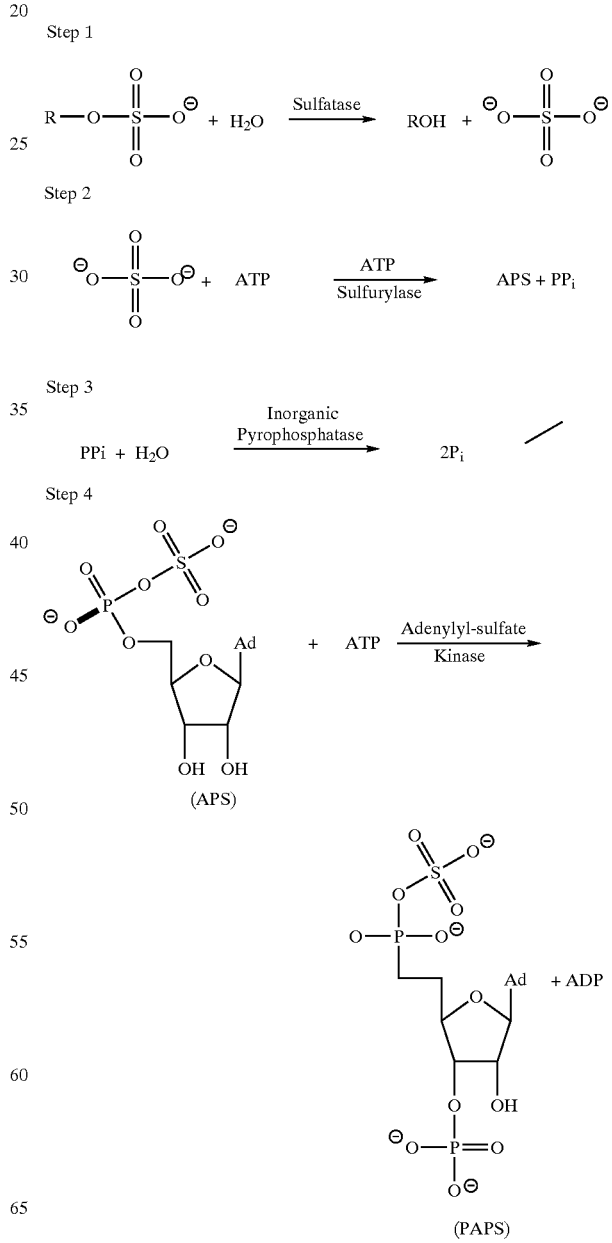

Step 5

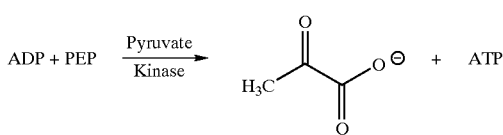

Step 6

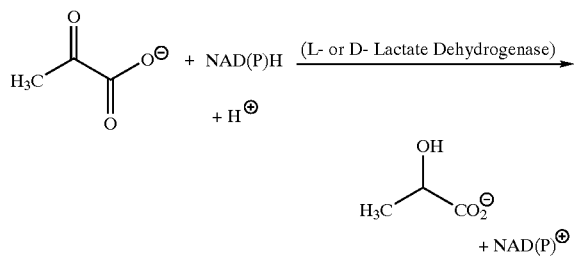

Scheme 4 illustrates a second enzyme/coenzyme couple wherein the sulfate byproduct in the organic reaction in the organic solvent layer is a sulfate monoester. In step 1, a sulfatase facilitates the hydrolysis of sulfate monoester to form an alcohol and a sulfate. Suitable sulfatase enzymes include, but are not limited to, Enzyme Commission Number 3.1.6.1 and Enzyme Commission Number 3.1.6.2. The sulfate then serves as the substrate for step 2 wherein ATP and ATP sulfurylase facilitate the formation of adenylyl sulfate and pyrophosphate. An example of a suitable sulfurylase enzyme includes Enzyme Commission Number 2.7.7.4. Pyrophosphate then serves as the substrate for step 3 in which a molecule of water and a molecule of inorganic pyrophosphate form two molecules of inorganic phosphate with the assistance of inorganic pyrophosphatase. A suitable inorganic pyrophosphatase is the enzyme possessing Enzyme Commission Number 3.6.1.1. In step 4, adenylyl sulfate and ATP are converted to 3' phosphoadenylyl sulfate (PAPS) and ADP through the action of adenylyl-sulfate kinase. An example of a suitable adenylyl-sulfate kinase would be the adenylyl-sulfate kinase having Enzyme Commission Number 2.7.1.25. Another enzyme that could catalyze step 4 is the dual function human enzyme phosphoadenosine-phosphosulfate synthase. The human enzyme phosphoadenosine-phosphosulfate synthase can catalyze step 4 as well as Step 2. In step 5 one molecule of ADP and one molecule of phosphoenolpyruvate are converted to one molecule of pyruvate and one molecule of ATP by the enzyme pyruvate kinase. A suitable pyruvate kinase is the enzyme having Enzyme Commission Number 2.7.1.40. The pyruvate produced in step 5 then serves as the substrate for step 6 of the enzyme/coenzyme couple. In step 6, one pyruvate and one molecule of NAD(P)H are converted to lactate and NAD(P)+ through the action of lactate dehydrogenase. Lactate dehydrogenases that can be used in this conversion include L- or D-lactate dehydrogenase. An example of a suitable L-lactate dehydrogenase includes, but is not limited to, the enzyme having Enzyme Commission Number of 1.1.1.27. An example of a suitable D-lactate dehydrogenase is the enzyme having Enzyme Commission Number of 1.1.1.28. The selection of appropriate enzymes and coenzymes as well as the corresponding conditions for their optimal functioning in the aqueous solvent layer is well within the skill of one of ordinary skill in the art. The pH of the aqueous solvent layer in which the enzyme/coenzyme couple is operating can generally range from about 6.5 to about 8.5. The preferred pH of the aqueous solvent layer for this particular enzyme/coenzyme couple for a sulfate byproduct will depend on the pH at which the particular enzymes and coenzymes selected for the enzyme/coenzyme couple optimally function. Any suitable buffer can be employed with this enzyme/coenzyme couple, the selection of which is readily made by one of ordinary skill in the art.

This enzyme/coenzyme couple for a sulfate byproduct consists of (i) sulfatase; (ii) ATP sulfurylase and ATP; (iii) inorganic pyrophosphatase; (iv) adenylyl-sulfate kinase and ATP; (v) pyruvate kinase and PEP; and (vi) LDH and NAD(P)H. The first step of Scheme 4 involves the hydrolysis of a sulfate monoester to produce sulfate. If the byproduct of the organic reaction in the organic solvent layer were to be simply a sulfate ion, the first step employing sulfatase would not be necessary and only 5 enzymes would be utilized in the enzyme/coenzyme couple. Thus, if the byproduct of the organic reaction in the organic solvent layer were to be simply a sulfate ion, the enzyme/coenzyme couple would consist of sulfurylase and ATP; inorganic pyrophosphatase; adenylyl-sulfate kinase with ATP; pyruvate kinase with PEP; and LDH with NADH if the coenzyme used were NADH. If the coenzyme used were NADPH, the enzyme/coenzyme couple would consist of sulfurylase and ATP; inorganic pyrophosphatase; adenylyl-sulfate kinase with ATP; pyruvate kinase with PEP; and LDH with NADPH.

4) Phosphate Byproduct

An enzyme/coenzyme couple is shown in Scheme 5 below for a dialkyl phosphate byproduct or leaving group. The same couple could be used for a monoalkyl phosphate leaving group. The same couple without the initial phosphatase enzyme could be used for a simple, inorganic phosphate leaving group.

Scheme 5

Step 1A:

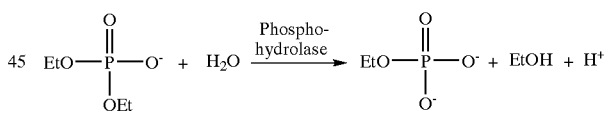

Step 1B:

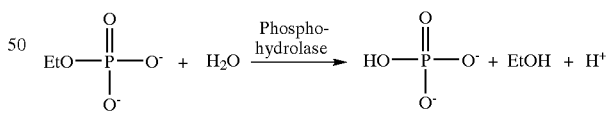

Step 2:

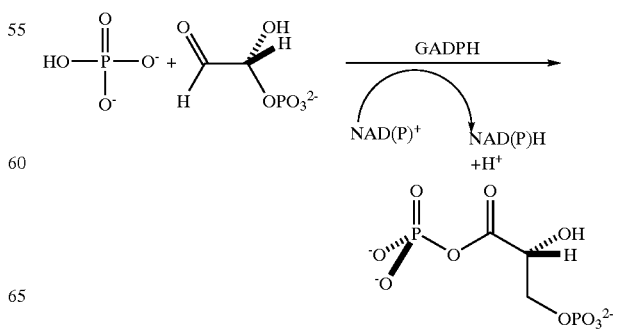

Step 3:

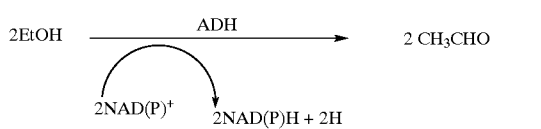

Step 4:

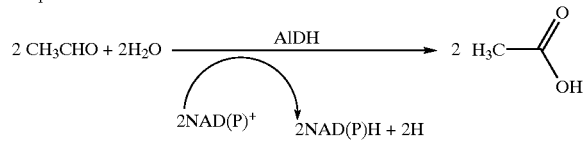

In part A of step 1 a phosphohydrolase enzyme will catalyze the hydrolysis of a phosphate diester to form a phosphate monoester and an alcohol. In part B of step 1 the monoalkyl phosphate or phosphate monoester is hydrolyzed by a phosphohydrolase enzyme to produce a phosphate and a second ethanol.

In this regard it is to be noted that while this couple has been illustrated specifically for diethyl phosphate leaving groups in Scheme 5, a related couple involving (i) a phosphate monoester hydrolase, (ii) a phosphate diester hydrolase, and (iii) GAPDH, GAP, and NAD(P)$^+$ could be used for any other dialkyl phospate leaving group.

At least two phosphohydrolases are known to catalyze the cleavage of both phosphate diesters and phosphate monoesters. These phosphohydrolases include *E. coli* alkaline phosphatase and *E. aerogenes* phosphohydrolase. The reactions of the enzyme/coenzyme couple shown in Scheme 1 are for a phosphate diester byproduct. Phosphate monoester byproducts may be monitored using the same enzyme/coenzyme couple except omitting part A of the first step. However, if a phosphate monoester is the byproduct, then the enzyme couple begins with part B of the first step. The monoalkyl phosphate is hydrolyzed to produce phosphate and one molecule of ethanol. Thus, the monoester phosphate enzyme/coenzyme couple consists of (i) a phosphohydrolase; (ii) GAPDH with NAD(P)$^+$ and glyceraldehyde 3-phosphate; (iii) alcohol dehydrogenase with NAD(P)$^+$; and (iv) aldehyde dehydrogenase with NAD(P)$^+$.

The phosphodiester couple is the same with the proviso that a phosphohydrolase enzyme(s) capable of hydrolyzing both phosphate di- and mono-esters are to be included. In this couple, two molecules of ethanol are produced for each phosphate diester byproduct ultimately leading to the formation of five molecules of NAD(P)H. (See scheme 5). Alternatively, one may use only a phosphodiesterase enzyme, alcohol dehydrogenase, aldehyde dehydrogenase and NAD(P)$^+$. In such a case, only two NAD(P)H molecules would be formed per phosphate diester byproduct in the aqueous layer. Yet a third possibility for the phosphate diester couple would involve phosphohydrolase enzyme(s) capable of phosphate mono- and di-ester cleavage, alcohol dehydrogenase, aldehyde dehyrogenase and NAD(P)$^+$. In this case, four molecules of NAD(P)H would be formed per molecule of phosphate diester diffusing into the aqueous layer.

In step (ii) of the enzyme/coenzyme couple, glyceraldehyde phosphate dehydrogenase catalyzes the formation of 1,3-diphosphoglycerate from phosphate and glyceraldehyde 3-phosphate with NAD(P)$^+$ serving as oxidant, leading to NAD(P)H formation. Suitable glyceraldehyde phosphate dehydrogenase enzymes include, but are not limited to, those having Enzyme Commission Number 1.2.1.11 for NAD$^+$ and Enzyme Commission Number 1.2.1.12 for NADP$^+$. In step (iii) the two ethanol molecules that are produced in parts A and B of step 1 are converted by alcohol dehydrogenase to two acetaldehyde molecules, with concomitant conversion of two NAD(P)$^+$ equivalents to two NAD(P)H equivalents. Suitable alcohol dehydrogenase enzymes include, but are not limited to, those having Enzyme Commission Number 1.1.1.1 for NAD$^+$ and Enzyme Commission Number 1.1.1.2 for NADP$^+$. The two acetaldehyde molecules are then substrates for aldehyde dehydrogenase in the fourth step. Two molecules of water and two molecules of NAD(P)$^+$ serve as co-substrates producing two molecules each of acetate and NAD(P)H. Suitable aldehyde dehydrogenase enzymes include, but are not limited to, those having Enzyme Commission Number 1.2.1.3 for NAD$^+$, Enzyme Commission Number 1.2.1.4 for NADP$^+$, and Enzyme Commission Number 1.2.1.5 for either NAD$^+$ or NADP$^+$. The appearance of NAD(P)H is the spectroscopically observable event that is monitored in the aqueous solvent layer.

5) Alcoholic Byproducts

The present invention also contemplates the use of oxidase-based couples for alcoholic leaving groups such as EtOH and MeOH and for alcoholic reaction products. Such products include those formed in lewis acid-catalyzed epoxide opening or epoxide hydrolysis, in TM-catalyzed dihydroxylation or aminohydroxylation reactions, in TM catalyzed allylic substitution with hydroxide or water as the nucleophile, in aldol condensations, carbonyl reductions, or nucleophilic additions to carbonyls, and conjugate additions of water or hydroxide.

For example, RCHOH and $O_2$ react in the presence of an alcohol oxidase to form RCHO and hydrogen peroxide. Alternatively, RCHO and $O_2$ react in the presence of an aldehyde oxidase to form RCOOH and hydrogen peroxide. The aldehyde may be a pig liver enzyme which displays broad substrate specificity. Suitable aldehydes are butyraldehyde, 2-methylbutyraldehyde and 2-ethylbutylaldehydes optionally substituted with methyl or ethyl.

The hydrogen peroxide is then reacted with a suitable dye of which quite a number are known. For example, ABTS$^{red}$ in the presence of peroxidase (e.g. from horseradish) and $H_2O_2$ forms ABTS$^{oxid}$ which absorbs at 405–410 nm. ABTS stands for 2,2'-azinobis(3-ethylbenzothiazoline-6-sulfonic acid) and is a soluble dye substrate for peroxidase and is thus appropriate for use with cuvet assays and 96-well plate assays.

6) Amine Byproducts

The present invention also contemplates the use of amine oxidase/peroxidase/dye-based couples for amine byproducts.

In situ Measurement of Enantioselectivity and Relative Rates

The biphasic process is suitable for determining, in situ, the stereoselectivity of organic reactions, as well as relative reaction rates. One can envision at least four distinct types of stereoselectivity that could be screened by ISES: (1) Kinetic resolution of enantiomers (the process by which enantiomers are separated through the more rapid reaction of one with a chiral catalyst or reagent. Note: A special case of this method is one in which the reaction conditions also permit the interconversion of the two enantiomers of starting material. In such a case, a greater than 50% yield of a single enantiomer can be obtained from racemic starting compound); (2) Desymmetrization of meso compounds (the process by which an achiral, meso compound is desymmetrized through the more rapid reaction of one "pro-chiral arm" of the compound with a chiral catalyst or reagent); (3)

Enantioselective synthesis (the process by which an achiral reactant is converted to a chiral product, and in which one enantiomer predominates,) through the use of a chiral catalyst or reagent and (4) Diastereoselective synthesis (the process by which a chiral reactant is treated with a reagent, whether achiral or chiral, to produce a product with at least one new stereocenter. In the case of a single new stereocenter, two diastereomers are produced, and a diastereoselective transformation yields one diastereomer in excess over the other).

There are at least two complementary methods by which ISES can be used to determine the enantioselectivity (that is, the ratio of one enantiomer to the other in the product) of a given reagent or catalyst (Note that for case (4), ISES could be utilized in an analogous way to determine diastereoselectivity)

In the first method, two identical reactions are performed in parallel in two identical layers. However, the two parallel reactions differ in the reporting enzymes present in their aqueous layers. One aqueous solvent layer contains an enzyme that reacts preferentially with one enantiomer [e.g. (S) {Note: For simplicity, reference is made to two enantiomers as simply (S) or (R) here though each enantiomer may, of course, contain more than one stereogenic center}] while the other aqueous solvent layer contains different enzyme that reacts preferentially with the other enantiomer [e.g. (R)]. The (S):(R) ratio in the product for the chiral catalyst or reagent being screening is then given by the ratio of the rates seen by ISES for these two cuvets, respectively. (Note: If either reporting enzyme is not "absolutely" enantiospecific within the experimental uncertainty, then the rate shown for that reporting enzyme needs to be corrected for the inherent enantioselectivity of that enzyme).

In the second method for determining enantioselectivity, again, two cuvets are used, but in this case, identical reporting enzyme(s) are used in each cuvets. The two cuvets differ only in the handedness of the chiral catalysts or reagents employed. So, for example, if an (S)-product specific enzyme is used in both cuvets, then the ratio of the rate seen in the "(R)-catalyst" cuvet to the rate seen in the "(S)-catalyst" cuvet will give will give the (S):(R) product ratio of the reaction catalyzed by the "(R)-catalyst." (This is because the rate of (S)-product formation from the "(S)-catalyst" is necessarily equal to the rate of (R)-product formed by the "(R)-catalyst" as the transition states for these two transformations are mirror images and, hence, equal in energy).

It is worthy of note that a comparison of relative [(R)+(S)] rates for a series of catalysts will also give the overall relative rates of reaction for the catalysts being compared. In this way, both relative rates and enantioselectivity can be measured by ISES for a series of chiral catalysts or reagents.

An example of the first type of enantioselective process described above (kinetic resolution) can be found in the opening of a racemic epoxide with a nucleophile in the presence of a chiral catalyst. Perhaps the simplest nucleophile is water, in which case this reaction is typically denoted as HKR (hydrolytic kinetic resolution). One successful such reaction is reported Eric N. Jacobsen's research group in Schaus et al. *Highly Selective Hydrolytic Kinetic Resolution of Terminal Epoxides Catalyzed by Chiral (salen)Co$^{III}$ Complexes. Practical Synthesis of Enantioenriched Terminal Epoxides and 1,2-Diols, J. Am. Chem. Soc.*, 2002, 124, No. 7, 1307–1315.

An exemplary procedure for screening HKR with ISES involves an organic layer containing the racemic epoxide and the catalyst to be screened in the presence or absence of an added organic solvent. A small amount of water may also be added to the organic layer, as well, prior to layering. The aqueous layer consists of an appropriate buffer and a reporting enzyme and cofactor, such as an alcohol dehydrogenase that is selective for either the (S) or (R)-1,2-diol that is formed and a nicotinamide cofactor (e.g. NAD$^+$ or APAD$^+$). To enhance this signal, an aldehyde dehydrogenase may also be added, provided that enzymatic oxidation of the 1,2-diol gives an aldehyde and that the aldehyde dehydrogenase chosen accepts the predominant enantiomer oxidized in the previous enzymatic step. A buffer pH is chosen so as to minimize the background, uncatalyzed epoxide hydrolysis rate, yet permit a reasonable rate of alcohol/aldehyde oxidation in the enzymatic reporter reaction.

Alternatively, an alcohol oxidase/peroxidase/ABTS two enzyme couple/cofactor combination may be used to report on diol formation with time. Here too, an aldehyde oxidase enzyme may be added to enhance the signal, provided that the previously defined conditions are met.

It is expected that a large number of epoxide reactants will be found that are themselves organic-soluble, but whose diol hydrolysis products are water soluble, and are, indeed, capable of diffusing into the organic layer and being oxidized there enzymatically, leading to a spectroscopically observable redox change of a cofactor or dye molecule. Note that the epoxide may itself be less dense than water (e.g. propylene oxide) or more dense than water (e.g. epichlorohydrin). In the former case, the diol will diffuse down into a lower aqueous layer. In the latter case, the diol will diffuse upward into the aqueous layer. In either case, the layers may be inverted through the use of a cosolvent of the appropriate density, if desired.

Other examples of processes of the first type are given below.

Trost et al. *Dynamic Kinetic Asymmetric Transformation of Diene Monoepoxides: A practical Asymmetric Synthesis of Vinylglycinol, Vigabatrin, and Ethambutol, J. Am. Chem. Soc.*, 2000, 122, 5968–5976 describes a suitable process for such enantioselectivity reactions. This process is known as DYKAT or dynamic kinetic asymmetric transformation. Scheme 1 in this article demonstrates the asymmetric induction with monosubstituted allyl systems.

Trost et al. *Deracemization of Baylis-Hillman Adducts, J. Am. Chem. Soc.*, 2000, 122, 3534–3535 describes using oxygen nucleophiles with allylic esters to form an observable compound.

A good example of a stereoselective process of the third type that is screenable by ISES is the asymmetric dihydroxylation of alkenes. This is a reaction of tremendous importance to organic chemists. So much so that the 2001 Nobel Prize in Chemistry was shared by K. Barry Sharpless largely for the development of this type of reaction. For references to this type of transformation, see: Wai et al. *A Mechanistic Insight Leads to a Greatly Improved Osmium-Catalyzed Asymmetric Dihydroxylation Process, J. Am. Chem. Soc.*, 1989, 111, 1123–1125; Andersson and Sharpless *A Dramatic Ligand Effect on the Relative Reactivities of Substituted Alkenes with Osmium Tetroxide. J. Am. Chem. Soc.*, 1993, 115, 7047–7048; Döbler et al. *Osmium-Catalyzed Dihydroxylation of Olefins Using Dioxygen or Air as the Terminal Oxidant. J. Am. Chem. Soc.*, 2000, 122, 10289–10297.

Such a reaction often involves for example the oxidation of an achiral alkene (organic soluble) into a 1,2-diol (with appreciable water solubility in many cases). The relative rates and enantioselectivities of this dihydroxylation reaction would be screened as described for the HKR example above (detailed procedure below).

Experimental Procedure for Screening the HKR Reaction with ISES:

In each cuvet, the lower aqueous layer is composed of 520 μL 50 mM sodium pyrophosphate buffer, pH 7.5; 180 μL of 40 mM NAD+ dissolved in 25 mM sodium phosphate buffer (pH 7); 100 μL 100 mM KCl; 100 μL of horse liver alcohol dehydrogenase (HLADH, 0.015 U) in 25 mM sodium phosphate buffer (pH 7); 25 and 100 μL of yeast aldehyde dehydrogenase (YAlDH, 0.03 U) in 25 mM sodium phosphate buffer (pH 7). The final pH of this aqueous layer is 7.1. The organic layer was prepared separately and layered onto the aq. layer to initiate the reaction. In a typical example, the organic layer is prepared by adding 300 μL of (±)-propylene oxide (4.3 mmol) to 13 mg (0.02 mmol, 0.5 mole %) of (R,R)-(−)-N,N-bis(3,5-di-tertbutylsalicylidene)-1,2-cyclohexanediaminocobalt(III) acetate (prepared as described in the above reference (Schaus et al. 2002) in a 1.5 mL Eppendorf™ tube.) In some experiments, water (42 μL, 2.3 mmol, 0.55 equiv.) was added to the tube, as well. The tube is then vortexed hard, but briefly, and the contents of the tube are layered over the aqueous layer in the cuvet. One sees an increase in absorbance at 340 nm due to the reduction of NAD+. This Jacobsen catalyst is known to be quite specific for the hydrolysis of the (S)-enantiomer of propylene oxide. This leads to the formation of (S)-1,2-propanediol in the organic layer. This diol diffuses into the aqueous layer where it is oxidized to (S)-lactaldehyde (HLADH) and (S)-lactic acid through the sequential action of HLADH (horse linear alcohol dehydrogenase) and yeast aldehyde dehydrogenase, with the concomitant production of two molecules of NADH. The NADH may be monitored by UV absorbance (at 340 nm, say) or by fluorescence emission (at 470 nm, for instant after illumination in the 340–365 nm wavelength range).

Reactions in the Organic Solvent Layer

The process of the present invention can be used to monitor the rate of any organic reaction provided that the organic reaction produces a product or byproduct that can diffuse into the aqueous solvent layer and serve as an enzymatic substrate to produce a spectroscopically observable change in absorbance at a fixed wavelength. Suitable reactions are described in paragraph 15.

Allylic Substitution

The allylic substitution reaction can be represented generally as shown below:

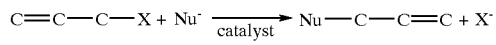

C=C—C—X is the structural element of an allylic substrate, X is to be the byproduct, and Nu is a nucleophile. C=C—C-Nu is the structural element of the product, wherein allylic transposition can occur for unsymmetrical substrates. The catalyst typically comprises a transition metal and one or more ligands, though a ligand other than a solvent is not necessarily required.

The leaving group (i.e., byproduct) is X⁻, which is typically a carbonate (⁻O₂COR) or a carboxylate (⁻O₂CR). However, the leaving group is not restricted to these compound classes and may also be a phosphate (ester), a sulfate (ester) or a carbamate, for example. In the case of a carbamate leaving group, an ethyl carbamate (⁻O₂COEt) is generally preferred. This leaving group is expected to fragment either before or after protonation to ultimately give CO₂ and ethanol. As has been described, the ethanol can diffuse into the organic layer where it may serve as a substrate for nicotinamide cofactor-dependent enzymatic oxidation, thereby producing a spectroscopically observable signal.

The catalyst is typically a transition metal catalyst which together with one or more ligands form a catalyst complex. The transition metal of the catalyst complex is typically selected from nickel (Ni), molybdenum (Mo), platinum (Pt), cobalt (Co), ruthenium (Ru), rhodium (Rh), rhenium (Re), tungsten (W), osmium (Os), iridium (Ir), manganese (Mn), vanadium (V), chromium (Cr), silver (Ag), iron (Fe), copper (Cu) and palladium (Pd). What transition metal catalysts are useful or preferred for the allylic substitution reaction will depend upon the objectives of the experiment using the process of the invention. Some examples of transition metals that are commonly preferred for allylic substitution reactions, however, include Ni, Mo, Pt, Pd, Rh, Co, Ir, Os, Ru, Rh, or W. More preferred transition metals are frequently Mo, Pd, or Ni. Pd is typically the most common transition metal used to promote allylic substitution reactions.

The transition metal may form a complex with one or more ligands. The ligands coordinate to the transition metal through one or more coordinating atoms. The ligands can be either achiral or chiral. The ligands of the catalyst complex typically have coordinating atoms selected from the elements arsenic (As), carbon (C), nitrogen (N), oxygen (O), phosphorus (P), selenium (Se), sulphur (S) or tellurium (Te). Which particular coordinating atoms are useful or preferred for the reaction will depend upon the particular metal substrate and reaction under study.

Examples of such chiral ligands include

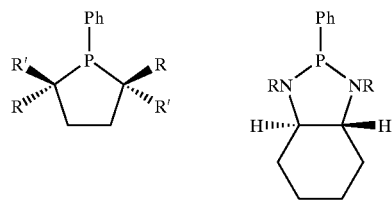

wherein Ph designates phenyl, R and R' each independently is selected from hydrogen, C₁₋₁₀-alkyl and phenyl, and R" is selected from C₁₋₁₀-alkyl and phenyl.

Examples of chiral bidentate ligands with nitrogen are

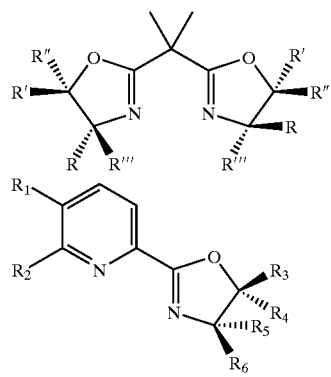

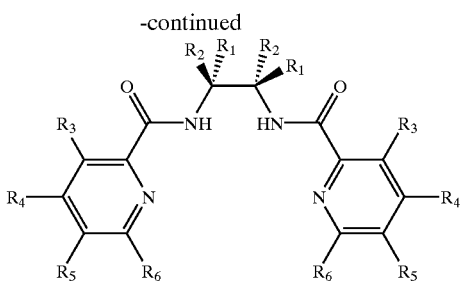

wherein $R_1$, $R_2$, $R_3$, $R_4$, $R_5$, and $R_6$ each independently is selected from hydrogen, $C_{1-10}$-alkyl, aryl, heteroaryl, hydroxy, alkoxy, di($C_{1-10}$-alkyl)amino, ($C_{1-10}$-alkyl)thio, and tri($C_{1-10}$-alkyl and/or phenyl)silyl, where different R substituents may interconnect to form a single moiety, for example, an oxetane or benzene ring. A particular example includes

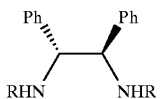

Many of the above mentioned ligands are thought to occupy two coordination sites on the metal. However, it is recognized that many will coordinate as monodentate or even multidentate ligands (e.g. tri- or even tetradentate ligands (particularly for the lanthamides and actinides which have, in general, higher coordination numbers from the transition metals)) depending on choice of reaction parameters, for example metal or solvent.

Examples of chiral bidentate ligands with phosphorus are

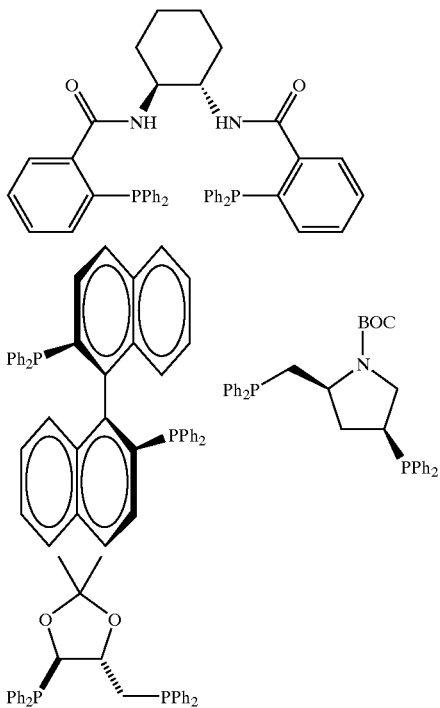

wherein Ph designates phenyl, and R and R' are each independently selected from hydrogen, $C_{1-10}$-alkyl, and phenyl, where R and R' together with the interconnecting atoms may form a carbocyclic ring such as a benzene or cyclohexane ring.

An example of a chiral bidentate ligands with phosphorus/nitrogen is

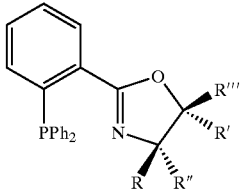

wherein Ph designates phenyl, and R, R', R" and R'" are each independently selected from hydrogen, $C_{1-10}$-alkyl and phenyl.

The catalyst complex may be prepared (or otherwise acquired) prior to the reaction, or the catalyst complex may be formed in situ. The appropriate place to prepare the catalyst complex will depend on the particular catalyst complex employed in the allylic substitution. In initial broad small scale screens, it may be convenient to prepare the catalyst in situ. On more extensive use, a pre-formed catalyst is often preferred. If it is desired to screen an array of potential reaction catalysts in parallel, a pre-formed catalyst may also be preferred. For example, where the catalyst comprises molybdenum, the molybdenum precursor, such as for example, $Mo(CO)_6$ is simply mixed with the ligand and the mixture is heated for a few minutes, for example from between about 1–5 min. The active catalyst can then be used directly with any further manipulation or purification.

As illustrated above, the allylic substrate to be used in the allylic substitution contains the structural element C=C—C—X. More specifically, the allylic substrate can be represented by the following formula:

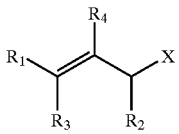

wherein $R_1$, $R_2$, $R_3$, and $R_4$ independently are selected from hydrogen, halogen, amine, amide, optionally substituted alkyl, alkoxy, alkenoxy, alkynoxy, aryloxy, heteroaryloxy, optionally substituted aryl, acyl, or optionally substituted heteroaryl or two of the substituents $R_1$, $R_2$, $R_3$, and $R_4$ together form a carbocyclic ring where X is a byproduct. X together with $R_1$ and the interconnecting atom may form an epoxide or an aziridine. In the situation where X together with $R_1$ and the interconnection atom form an epoxide or an aziridine, $R_1$ designates $C_{1-12}$ alkylene, e.g. methylene or ethylene, and X designates O or N, where the α-carbon of the $C_{1-12}$ alkylene is linked to the O or N and the interconnecting atom, respectively.

It is understood that the above formula is in no way restrictive for the present invention, as the present invention provides a method where almost any substrate of the allylic type can be used, i.e. the substitutions $R_1$–$R_4$ should simply be selected with due regard to the functional groups involved. It is well within the skill of a person of ordinary skill in the art to select the substrate so that any functional groups or entities of the substrate (with the exception of the allylic system) should be substantially unaffected by the reaction conditions. Suitable protecting groups for the allylic substitution reaction are well known to those skilled in the art; a listing of protecting groups can be found in Greene, T. W. and Wuts, P. G. M. (Protecting Groups in Organic Synthesis), the entirety of which is hereby incorporated by reference.

Some illustrative examples of substrates that can be used in the allylic substitution reaction are:

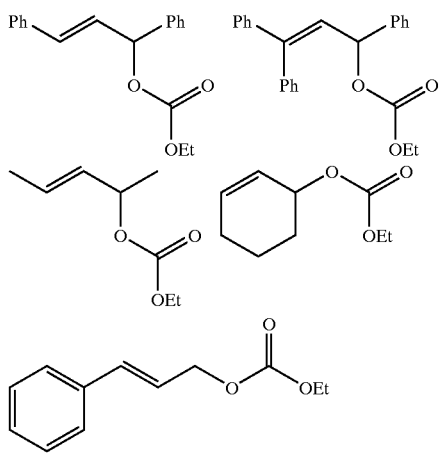

The nucleophile used in the allylic substitution reaction can be almost any nucleophile used in organic chemistry, for example C, S, N and O nucleophiles. Examples of general types of nucleophiles that can be employed in the allylic substitution reaction of the present invention include, but are not limited to

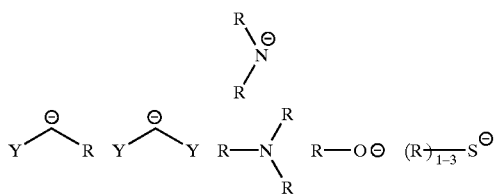

wherein Y is an electron withdrawing group and each R independently is selected from hydrogen, $C_{1-12}$ alkyl, aryl, aryl$C_{1-10}$ alkyl (e.g. benzyl), alkylheteroaryl, tri($C_{1-12}$ alkyl and/or phenyl)silyl, di($C_{1-12}$alkyl)amino, $C_{1-12}$ alkoxy, aryloxy, $C_{1-12}$ alkylsulfonyl, and $C_{1-12}$-alkyloxycarbonyl.

The nucleophile precursor can be deprotonated with a mild base. By mild base is meant a base whose conjugate acid has a pKa above 7. Nucleophiles may also be generated in situ by reacting a nucleophile precursor with a strong base. By strong base is meant a base having a pKa in the range of 10–50. Alternatively, the nucleophile may be pre-prepared.

If X is a carbonate, the preferred enzyme/coenzyme couple in the aqueous phase is ADH/NAD(P)$^+$ and AlDH/NAD$^+$. Ethyl carbonates are preferred because ethanol diffuses into the aqueous layer and functions well as a substrate for the ADH/NAD$^+$ and AlDH/NAD$^+$ enzyme/coenzyme couple. Thus, if a carbonate is the leaving group (i.e., byproduct) produced in the reaction in the organic solvent layer, then NAD(P)H is the spectroscopically observable compound that is monitored in the aqueous solvent layer. The production of NAD(P)H will be monitored spectroscopically by transmitting radiation through the aqueous solvent layer. Alternatively, an alcohol oxidase/peroxidase/ABTS couple can be used for either ethyl carbonate or methyl carbonate allylic leaving groups. If X is acetate, the preferred enzyme/coenzyme couples in the aqueous phase are: (i) ATP dependent Acetate Kinase/ATP, Pyruvate Kinase/PEP, and Lactate dehydrogenase/Lactate/NAD(P)H; or (ii) Pyrophosphate-dependent Acetate Kinase/pyrophosphate, GAPDH/NAD(P)$^+$ and GAP. If the former couple is used, then release of acetate in the organic layer ultimately leads to the consumption of NAD(P)H in the aqueous layer. With the latter couple, acetate release produces NAD(P)H formation in the aqueous layer.

For most enzyme/coenzyme couples, it is preferable to use a buffer in the aqueous phase. Suitable buffers for use in the aqueous solvent layer include, but are not limited to, pyrophosphate, phosphate, TRIS, imidazole MOPS, MES, acetate, borate, triethanolamine, HEPES, glycine, BICINE, and TRICINE. For the use of ATP-dependent Acetate Kinase/ATP, Pyruvate Kinase/PEP, and LDH/NAD(P)H enzyme/coenzyme couple, a phosphate buffer is preferred. However, if the Acetate Kinase/pyrophosphate, GAPDH/NAD$^+$ and GAP, Acetate Kinase/pyrophosphate, GAPDH/NADP$^+$ and GAP enzyme/coenzyme couple is used, a phosphate buffer should not be used in the aqueous solvent layer, as phosphate is a product of the first enzymatic reaction in the couple.

Suitable organic solvents for use in the organic solvent layer with the allylic substitution reaction include, but are not limited to, hexane, benzene, cyclohexane, pentane, heptane, 1,2-dimethoxyethane, dioxane, 1,2-dichloroethane, 1,2,3,4-tetrachloroethane, tetrahydrofuran, toluene, carbon tetrachloride, chloroform, ethyl acetate, methyl t-butyl ether, butyl acetate, methylene chloride, diethyl ether, or mixtures thereof. Which organic solvents are preferred for use with the allylic substitution reaction may depend on the type of allylic substitution reaction under study.

The allylic substitution reaction is a quite useful organic reaction that is of interest to researchers for many reasons. The allylic substitution reaction can be used to prepare (either directly or via intermediates) a number of interesting biologically active compounds. Such biologically active compounds include carbonucleosides such as aristeomycin and carbovir, alkaloids such as (+) gamma-lycorane and pancratistatin, and antifungal agents such as polyoxins and nikkomycins.

One specific type of allylic substitution reaction is an allylic amination. The following reaction is an example of an intramolecular allylic amination. Reacting a compound having the formula

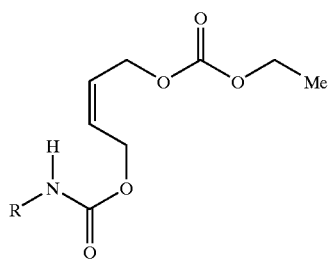

wherein R is a nitrogen protecting group, in the presence of a transition metal catalyst, the transition metal catalyst comprising a transition metal and one or more ligands, in an organic solvent layer to produce carbon dioxide, ethanol, and a product of formula

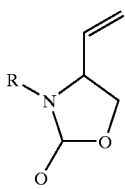

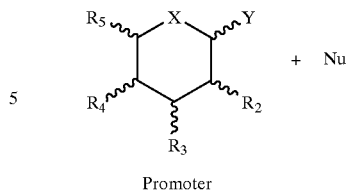

Promoter wherein R is a nitrogen protecting group.

The transition metal of the transition metal catalyst used in this allylic amination is typically Ni, Mo, Pt, Co, Ru, Rh, Ir, Mn, V, Cr, Ag, Fe, Cu or Pd. The ligands of the transition metal catalyst contain a coordinating atom, through which the ligand coordinates to the transition metal. The coordinating atom typically is N, P or As, and possibly O or C. Examples of ligands include, but are not limited to, cyclooctadiene, cycloheptatriene, CO, $C_7H_8$, $PPh_3$, and Cl. Examples of transition metal catalysts include, but are not limited to, Pd catalysts, $Ni(COD)_2$, $Mo(CO)_3(C_7H_8)$, $Pt(PPh_3)_4$, $RhCl(PPh_3)_2$, and $Co(Cl)_2$. Pd catalysts are generally preferred transition metal catalysts for use in the allylic amination reaction. Examples of suitable nitrogen protecting groups include, but are not limited to, $C_6H_2$-3,4,5-$(OMe)_3$, benzhydryl, PNP (p-nitrophenyl), Boc, and PMP (p-methoxyphenyl).

For this allylic amination reaction the preferred enzyme/coenzyme couples in the aqueous phase are ADH/NAD(P)$^+$ and AlDH/NAD(P)$^+$. Preferably, the production of NADH is monitored spectroscopically by transmitting electromagnetic radiation through the aqueous solvent layer. With this particular allylic amination reaction, it is preferred to use a buffer in the aqueous phase. Suitable buffers for use in the aqueous solvent layer include, but are not limited to, pyrophosphate, phosphate, and TRIS. A preferred buffer for use in the aqueous solvent layer for the study of this allylic amination reaction is pyrophosphate buffer.

Suitable organic solvents for use in the organic solvent layer with this particular allylic amination reaction include, but are not limited to, hexane, tetrahydrofuran, toluene, ethyl acetate, methyl t-butyl ether, diethyl ether, or mixtures thereof. Preferably, the organic solvents used in the organic solvent layer of this allylic amination reaction are a mixture of the organic solvents tetrahydrofuran, hexane, and toluene.

The organic solvent layer for this allylic amination reaction may also optionally be prepared by introduction of a base. Examples of suitable bases include, but are not limited to, LiHMDS, KHMDS, and NaHMDS.

The allylic amination reaction itself can be used to prepare β,γ-unsaturated amino acids. Specifically, the allylic amination reaction can be used to prepare vinylglycine, a known inactivator of PLP (pyridoxal phosphate)-dependent transaminases for L-aspartate, L-alanine, L-serine and D-alanine. The allylic amination reaction can also be used to prepare E-2-amino-5-phosphono-3-pentenoic acid (APPA), which has been shown to inhibit two PLP-dependent enzymes, cystathionine (-synthase (tight-binding reversible inhibitor; $K_i$=27 μM) and threonine synthase (irreversible inhibitor; $K_i$=400 μM; $k_{inact}$=0.25 min$^{-1}$).

Glycoside Activation Reaction

Another organic reaction that can be evaluated in the method of the present invention is the glycoside activation reaction wherein
X represents O, NR, or S;
Y represents OR,

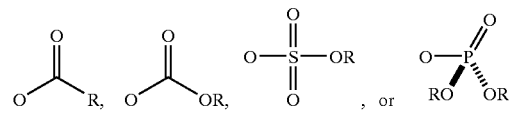

R is independently selected from the group consisting of H, alkyl, heteroalkyl, aryl, aralkyl, heteroaryl, heteroaralkyl, acyl and sulfonyl;
$R_2$, $R_3$, and $R_4$ are independently selected from the group consisting of R, —OR', —SR', —NR'$_2$, —OSO$_3$H, —OPO$_3$H$_2$;
$R_5$ is selected from the group consisting of R, —(CR$_2$)$_n$OR', —(CR$_2$)$_n$SR', and (CR$_2$)$_n$NR'$_2$; and
n is an integer selected from the range of 0 to 10,
Nu is a nucleophile selected from —HO—R, —HS—R, or

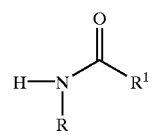

wherein R and R$^1$ are independently selected from alkyl, alkenyl, alkynyl, aryl, heteroaryl, or acyl, and the promoter is a Lewis Acid.

Alternatively, neutral carbon nucleophiles capable of reacting with anomeric-type electrophiles include, for example, allyl silanes, silyl enol ethers and silyl ketene acetyls.

Examples of suitable Lewis acids include, but are not limited to, zinc chloride, scandium triflate, boron trifluoride etherate, iron (III) chloride, titanium tetrachloride, titanium tetra(isopropoxide), lithium perchlorate, aluminum trichloride, tin tetrachloride, mercury cyanide, mercury (II) trifluoroacetate and europium chloride.

As one example, the glycosyl phosphates employed in the reaction can be synthesized from commercially available differentially protected glycal precursors in a highly efficient one-pot, two step synthesis. For example, the conversion of glycals to anomeric phosphates can be achieved by epoxidation of the double bond of glycal 4 with dimethyldioxirane (DMDO) to furnish the 1,2-anhydrosugar. Opening of the epoxide with a phosphoric acid derivative furnishes anomeric phosphates which are C-2 protected in situ. Addition of an excess of acetyl chloride, benzoyl chloride or pivaloyl chloride and DMAP followed by purification by filtration through a short pad of silica can provide the desired protected glycosyl phosphates in good yield. The formation of either α or β glycosyl phosphates can be effected through the selection of solvents employed. For example, THF can be used to form α glycosyl phosphates, toluene can be used to form β glycosyl phosphates, and dichloromethane can be used to form a mixture of α glycosyl phosphates and β glycosyl phosphates. For each class of glycosyl donor (i.e., sugar bearing a leaving group at the anomeric center), screening can be done in much the same way as described for the allylic substitution reaction. The choice of enzyme couple is dictated by the leaving group ((e.g., acetate ethyl carbonate, sulfate (ester) or phosphate (ester)) as before. Screening may be done to optimize (i) the type of promoter, (ii) the type of nucleophile, (iii) the nucleophile protecting group(s), and/or (iv) the protecting groups for the activated sugar (i.e., glycosyl donor).

Diels-Alder Reaction

Another organic reaction that can be investigated using the method of the present invention is the hetero-Diels-Alder reaction. An important variant of the Diels-Alder reaction comprises reacting an electron-rich oxygenated diene with an aldehyde, thioaldehyde or imine to produce a six-membered heterocyclic ring. One of the most common classes of diene used in this reaction features an alkoxy group [$OR_1$] at the 1-position and a silyloxy group [$OSi(R_3)_3$] at the 3-position. This is the class of Danishefsky dienes discovered by Samuel J. Danishefsky. When such dienes are used, elimination of both the silyl group and the alkoxy group, under the influence of a promoter following the initial formal [$4\pi+2\pi$] cycloaddition, leads to a dihydropyran-4-one product (or the ring nitrogen or sulfur analogues thereof). Typically, a Lewis acid, such as $BF_3$-etherate or $ZnCl_2$, (such as trifluoroacetic acid) is used to catalyze the hetero-Diels Alder step and a relatively strong Bronsted acid is used to promote the 1,4-elimination leading to dihydropyran-4-one formation. The enzyme/coenzyme coupling described herein for monitoring of alcohol (e.g., ethanol) leaving groups (i.e., byproducts) may be used to screen for either (a) catalysts that will promote both the hetero-Diels-Alder step and the subsequent elimination, or (b) promoters specific for 1,4-elimination step. It should be noted that chiral Lewis acid catalysts may also be employed, in which case both steps can lead to enantiomerically-enriched heterocyclic products.

Generally, the Diels-Alder reaction can be represented as follows:

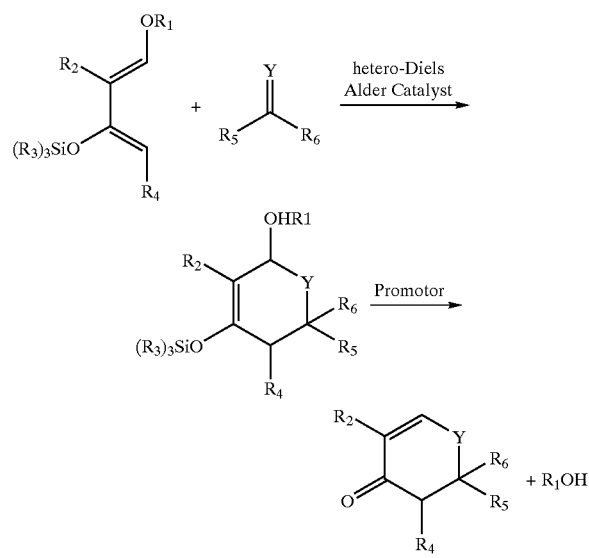

wherein
Y represents O, S, or $NR_7$;
$R_1$ is alkyl, alkenyl or alkynyl;
$R_2$, $R_3$, $R_4$, $R_5$ and $R_6$ each independently represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_8$ any two or more of the substituents $R_2$, $R_3$, $R_4$, $R_5$ and $R_6$ taken together may form a carbocylic or heterocyclic ring having from 4 to 8 atoms in the ring structure;
$R_8$ represents an aryl, a cycloalkyl, a cycloalkenyl, a heterocycle or a polycycle; and
m is zero or an integer in the range of 1 to 8. In certain embodiments $R_1$, $R_2$, $R_3$ and $R_4$ are chosen such that the substrate has a plane of symmetry.

The process of the invention may be practiced by combining said aldehyde (or thioaldehyde or imine) diene, and a catalyst as described herein, and maintaining the combination under conditions appropriate for the chiral catalyst to catalyze a cycloaddition reaction between the two substrates, followed by formal hydrolytic elimination to the dihydropyran-4-one product, whereby a molecule of alcohol and a molecule of trialkylsilanol is released. The alcohol would then diffuse into the aqueous layer where it would lead to the formation of two molecules or NAD(P)H (from 2 NAD(P)$^+$) through the sequential action of alcohol dehydrogenase and aldehyde dehydrogenase.

By monitoring a series of such hetero-Diels-Alder 1,4-elimination reactions in parallel, in this manner, one skilled in the art could use the aforementioned enzyme/coenzyme coupled screen to identify the most efficient promoters for this two-step process.

Ester Deprotection Reaction

Another general type of reaction that can be employed in the process of the present invention is an ester deprotection. One type of an ester deprotection reaction is a phosphate triester deprotection. This is important as such a step is a necessary part of the phosphotriester method for synthesizing DNA. This method was the first practical, controlled approach to the synthesis of polymeric nucleic acids and led to the Nobel prize in chemistry for Khorana. With a phosphate triester deprotection, the process of the present invention could be conducted by comparing the rates of a series of phosphate triester deprotection reactions run in parallel, the process comprising (i) introducing, in several parallel cells, a starting material of formula,

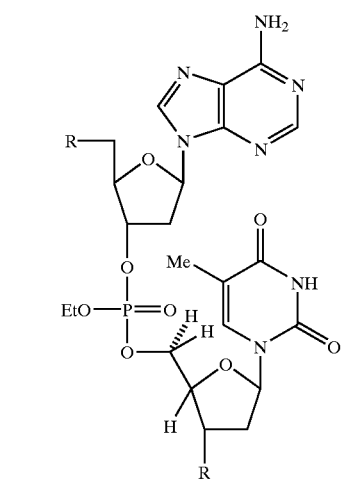

wherein R is a protecting group for a primary alcohol, into an organic solvent layer, and (ii) reacting the starting material with an ester deprotection promoter. Typical ester-cleavage promoters to be screened include nucleophiles (e.g., ⁻CN (cyanide), ⁻N₃ (azide), ⁻SR, ⁻X (halide)), substituted pyridines, imidazoles, phophines, and/or Lewis acids.

Successful cleavage of the ethyl ester of the phosphate triester functionally would lead to release of ethanol in the organic layer. Diffusion from said organic solvent layer into an adjacent aqueous solvent layer would then permit the ethanol to serve as an enzymatic substrate for an enzyme/coenzyme couple to produce a spectroscopically observable compound at a rate proportional to the rate of ester cleavage. Were such an assay to be run in parallel for a series of ester cleavage promoters, one could use the relative rates of coupled NAD(P)H formation observed to identify the most efficient of such promoters, be they Lewis acids, nucleophiles, or Lewis acid/nucleophile combinations.

Suitable solvents for the organic solvent layer include, but are not limited to hexane, benzene, cyclohexane, pentane, heptane, 1,2-dimethylmethoxyethane, dioxane, 1,2-dichloroethane, 1,2,3,4-tetrachloroethane, tetrahydrofuran, toluene, carbon tetrachloride, chloroform, ethyl acetate, methyl t-butyl ether, methylene chloride, and diethyl ether. Preferred solvents for the reaction would be determined by the type of variable being evaluated for the particular phosphate triester deprotection reaction being monitored.

The aqueous solvent layer may include a buffer. Suitable buffers include, but are not limited to, pyrophosphate, phosphate, TRIS, imidazole, MOPS, MES, acetate, borate, triethanolamine, HEPES, glycine, BICINE, and TRICENE.

Another type of ester deprotection reaction is a carboxylic acid ester deprotection. With a carboxylic acid ester deprotection the process of the present invention could be conducted by comparing the rates of a series of carboxylic acid ester deprotection reactions run in parallel, the process comprising (i) introducing, in several parallel cells, a starting material of formula,

RCOOR' wherein R is hydrocarbyl, into an organic solvent layer, and (ii) reacting the starting material with a nucleophilic ester cleavage promoter, a Lewis acid catalyst or a combination of these in a manner parallel to that described herein for phosphate triesters.

Acylation of Alcohols

Acylation of alcohols is another reaction that can be employed in the method of the present invention. The acylation of alcohols can be represented as follows

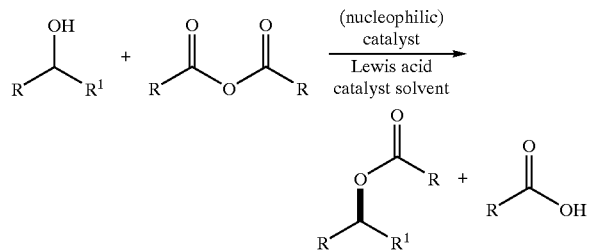

wherein R" implies a $C_1$–$C_{10}$ saturated or unsaturated alkyl group or aryl group. This method can be used to screen for acetate or butyrate, for example, using: (i) ATP-dependent Acetate Kinase couple: (a) ATP-dependent Acetate Kinase/ATP; (b) Pyruvate Kinase/PEP; or (c) lactate dehyrogenase/NAD(P)H; or, (ii) Pyrophosphate-dependent Acetate Kinase couple: (a) Pyrophosphate-dependent Acetate Kinase/pyrophosphate; (b) GAPDH/NAD(P)⁺; or, the ATP-dependent Butyrate Kinase couple directly analogous to (i) set forth above.

As with phosphate triester deprotections, one skilled in the art would choose appropriate ester cleavage promoter candidates for screening. These might include, for example, nucleophilic catalysts alone, Lewis acid catalysts alone, or a combination of both, as described for phosphate triester deprotenation.

Definitions

For convenience, before further description in the present invention, certain terms employed in the specification, examples and appended claims are collected here.

The term "nucleophile" is recognized in the art, and as used herein means a chemical moiety having a reactive pair of electrons. Examples of nucleophiles include uncharged compounds such as amines, mercaptans and alcohols, and charged moieties such as alkoxides, thiolates, carbanions, and a variety of organic and inorganic anions. Illustrative anionic nucleophiles include simple anions such as azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired. (For example, silanes may be suitable hydride donors under the biphasic reaction conditions given.)

The term "electron-withdrawing group" is recognized in the art and denotes the tendency of a substituent to attract valence electrons from neighboring atoms, that is to say that the substituent is electronegative with respect to neighboring atoms. A quantification of the level of electron withdrawing capability is given by the Hammet sigma constant. This well known constant is described in many references, for instance, J. March, Advanced Organic Chemistry, McGraw Hill Book Company, New York (1977 edition) pp. 251–259. The Hammett constant values are generally negative for electron donating groups ($\delta[P]$=–0.66 for $NH_2$) and positive for electron withdrawing groups ($\delta[P]$=0.78 for a nitro group), $\delta[P]$ indicating para substitution. Exemplary electron withdrawing groups include nitro, ketone, aldehyde, sulfonyl, trifluoromethyl, —CN, chloride, and the like. Exemplary electron-donating groups include amino, methoxy, and the like.

The term "diene" refers to a molecule containing at least one pair of conjugated π-bonds. The individual π-bonds of the diene moiety may be between any two atoms drawn from the set composed of C, N, O, S, and P. The conjugated π-bonds of the diene must be capable of adopting what is referred to as the s-cis conformation.

The term "dienophile" refers to a molecule containing at least one reactive π-bond. The individual π-bonds of the diene moiety may be between any two atoms drawn from the set composed of C, N, O, S, and P. The conjugated π-bonds of the diene must be capable of adopting what is referred to as the s-cis conformation.

The term "chiral" refers to molecules which have the property of non-superimposibility of their mirror image partner, while the term "achiral" refers to molecules which are superimposable on their mirror image partner.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers" refer to two stereoisomers that are not enantiomers.

In addition, "Ph" means phenyl; "Bz" means benzoyl; "Bn" means benzyl; "Me" means methyl; "Et" means ethyl; "iPr" means isopropyl; "tBu" and "t-Bu" means tert-butyl; "Ac" means acetyl; "TES" means triethylsilyl; "TMS" means trimethylsilyl; "protected hydroxyl" means —OP wherein P is a hydroxyl protecting group; and "hydroxyl protecting group" includes, but is not limited to, acetals having two to ten carbons, ketals having two to ten carbons, and ethers, such as methyl, t-butyl, benzyl, p-methoxybenzyl, p-nitrobenzyl, allyl, trityl, methoxymethyl, methoxyethoxymethyl, ethoxyethyl, methoxy propyl, tetrahydropyranyl, tetrahydrothiopyranyl; and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloroethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl protecting groups may be found in "Protective Groups in Organic Synthesis" by T. W. Greene, John Wiley and Sons, 1981, and Second Edition, 1991.

The "hydrocarbon" and "hydrocarbyl" moieties described herein are organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbyl groups, and include alkaryl, alkenaryl and alkynaryl. Preferably, these moieties comprise 1 to 20 carbon atoms.

The alkyl groups described herein are preferably lower alkyl containing from one to six carbon atoms in the principal chain and up to 20 carbon atoms. They may be straight, branched chain or cyclic and include methyl, ethyl, propyl, isopropyl, butyl, hexyl and the like. They may be substituted with aliphatic or cyclic hydrocarbyl radicals.

The alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like. They may be substituted with aliphatic or cyclic hydrocarbyl radicals.

The alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like. They may be substituted with aliphatic or cyclic hydrocarbyl radicals.

The aryl moieties described herein contain from 6 to 20 carbon atoms and include phenyl. They may be hydrocarbyl substituted with the various substituents defined herein. Phenyl is the more preferred aryl.

The heteroaryl moieties described are heterocyclic compounds or radicals which are analogous to aromatic compounds or radicals and which contain a total of 5 to 20 atoms, usually 5 or 6 ring atoms, and at least one atom other than carbon, such as furyl, thienyl, pyridyl and the like. The heteroaryl moieties may be substituted with hydrocarbyl, heterosubstituted hydrocarbyl or hetero-atom containing substituents with the hetero-atoms being selected from the group consisting of nitrogen, oxygen, silicon, phosphorous, boron, sulfur, and halogens. These substituents include hydroxy; lower alkoxy such as methoxy, ethoxy, butoxy; halogen such as chloro or fluoro; ethers; acetals; ketals; esters; heteroaryl such as furyl or thienyl; alkanoxy; acyl; acyloxy; nitro; amino; and amido.

The substituted hydrocarbyl moieties described herein are hydrocarbyl moieties which are substituted with at least one atom other than carbon and hydrogen, including moieties in which a carbon chain atom is substituted with a hetero atom such as nitrogen, oxygen, silicon, phosphorous, boron, sulfur, or a halogen atom. These substituents include hydroxy; lower alkoxy such as methoxy, ethoxy, butoxy; halogen such as chloro or fluoro; ethers; acetals; ketals; esters; heteroaryl such as furyl or thienyl; alkanoxy; acyl; acyloxy; nitro; amino; and amido.

The acyl moieties and the acyloxy moieties described herein contain hydrocarbyl, substituted hydrocarbyl or heteroaryl moieties. In general, they have the formulas —C(O)G and —OC(O)G, respectively, wherein G is substituted or unsubstituted hydrocarbyl, hydrocarbyloxy, hydrocarbylamino, hydrocarbylthio or heteroaryl.

EXAMPLES

General Information Regarding Organic Synthesis

All reactions were conducted under an argon atmosphere using flame-dried glassware unless otherwise noted. $Cl_2Ni(PPh_3)_2$, $Pt(PPh_3)_4$, were purchased from Strem and $Ni(COD)_2$, $Mo(CO)_3(C_7H_7)$, $ClRh(PPh_3)_3$ and $CoCl_2$-hexahydrate were from Aldrich. The latter complex was dried (100° C., overnight) on a Kugelrohr apparatus prior to use. Toluene and THF were distilled from sodium benzophenone ketyl. Acetonitrile, pyridine, methylene chloride and triethylamine were distilled from $CaH_2$. n-Butyllithium in hexanes (nominally 1.6 M) was purchased from Aldrich and titrated before use. NMR spectra were recorded on a Bruker-DRX-Avance-500 or a GE Omega-300 instrument Chemical shifts are reported relative to (i) residual $CHCl_3$ (7.25 ppm, $^1H$); (77.0 ppm, $^{13}C$) or (ii) $PPh_3$ (−5.80 ppm, internal capillary standard, 31P). For HMBC (Heteronuclear Multiple Bond Correlation) experiments, $^{13}C$ chemical shifts were determined by summing projections over the indirect ($^{13}C$) dimension of a proton detected 2-dimensional, gradient selected spectrum. Infrared spectra were obtained using an Nicolet Avatar 360 FTIR spectrometer. Mass spectra were acquired at the Nebraska Center for Mass Spectrometry (University of Nebraska).

General Information Regarding Enzyme Assays

All UV spectra were recorded on a Shimadzu UV-2101PC spectrophotometer equipped with a CPS-260 six-cell positioner with thermoelectric temperature control (set at 25° C.). Quartz cuvets were from Hellma. Pipetmen (P10, P200 and P1000) were from Rainin. (Yeast alcohol dehydrogenase (EC 1.1.1.1; lyophilized powder, nominally 280–440 U/mg solid depending upon the batch) was purchased from Sigma and yeast aldehyde dehydrogenase dehydrogenase (EC 1.2.1.5; lyophilized powder, nominally 20–54 U/mg protein, depending on lot no.) from Boehringer-Mannheim. β-NAD+ and β-NADH (disodium salt) were from Sigma.

Enzymatic Screening Procedures

Standard Assays—Solutions of both dehydrogenase enzymes were calibrated in terms of U/mL, using the standard assays delineated below. In each case, one S.I. unit is taken as the amount of enzyme catalyzing the formation of one μmol of NADH per minute. In a 1 mL final cuvet volume, this amounts to an absorbance change at 340 nm of 6.22 min$^{-1}$, or, more typically, 0.622 min$^{-1}$ per 100 mU of enzyme.

Alcohol Dehydrogenase—100 mM EtOH, 7.4 mM NAD+, 15 mM sodium pyrophosphate, pH 7.7. Typically, the stock solution of ADH was prepared by dissolving 1.5 mg solid of the commercial enzyme lyophilisate in 660 μL of 25 mM NaPO$_4$, pH 7. Addition of 0.5 μL of this solution (5 μL of a 1:10 dilution) to a 1 mL standard assay solution gives rise to an absorbance change of 0.44±0.06 min$^{-1}$ at 340 nm. This indicates the presence of 0.14 U/mL of stock solution.

Aldehyde Dehydrogenase—400 mM acetaldehyde, 7.4 mM NAD+, 15 mM sodium pyrophosphate, pH 7.7. Typically, the stock solution of AlDH was prepared by dissolving 5.2 mg solid of the commercial enzyme lyophilisate in 500 μL of 25 mM NaPO$_4$, pH 7. Addition of 10 μL of this to a 1 mL standard assay solution gives rise to an absorbance change of 0.13±0.01 min$^{-1}$ at 340 nm. This indicates the presence of 0.021 U/10 μL of stock solution.

Biphasic Screening Parameters

Optimal Interface Position—Quartz cuvets with a 1 cm light path and with a nominal one mL volume (actual filled volume=1.6 mL) were used. To establish an appropriate position for the interface, the cuvet was initially filled to a 1 mL volume with the standard aqueous assay solution (vide supra) and the Abs$_{340}$ vs. time was measured to establish a baseline value for the rate. This value was then compared to values for the same assay solution measured at cuvet volumes of 500 μL, 600 μL and 700 μL. No absorbance was seen with the 500 or the 600 μL solutions, whereas the expected baseline rate was observed for the 700 μL cuvet. We presume, therefore, that the spectrophotometer beam passes through the cuvet at approximately the 650 μL level. To insure that the organic/aqueous interface would be well-spaced from the beam, we chose to run biphasic assays with a rather "tall" 900 μL aqueous layer.

Organic Layer Composition

The organic solvent for these screens was selected to satisfy the following conditions: (1) Immiscibility in the aqueous buffer solution chosen. (2) Solubilization of all organic substrates and TM complexes chosen. (3) Promotion of the allylic displacement reaction under study (perhaps even by ligating to the metal). (4) Permitting diffusion of the ethanolic byproduct into the aqueous buffer layer. With these considerations in mind, several water-immiscible solvents were examined, initially with a focus on the latter consideration.

In model experiments, 110 micromol (6.4 microL) of EtOH (as a model for the release of EtOH from 110 micromol of ethyl carbonate substrate) was added to the organic solvent (400 microL) in a 1.5 mL microcentrifuge tube. After vortexing the mixture, it was layered above the usual aqueous layer [900 microL; containing 7.4 mM NAD+, AlDH (1.3 U) and ADH (0.12 U) in 15 mM sodium pyrophosphate, pH 7.7]. Observed rates of NADH formation were as follows:

| Solvent | ΔAbs (340 nm) {mAbs/min} |
|---|---|
| Hexane | 142 |
| THF | 47 |
| Toluene | 14 |
| THF/hexane (1:1) | 109 |
| THF/hexane/toluene (2:1:1) | 107 |

(Actual Ni-catalyzed reaction of 1a in latter solvent 58–60)

The THF/hexane/toluene solvent mixture provided a good balance between the need to promote allylic displacement and allow for significant EtOH diffusion into the aqueous layer, while also effectively solubilizing the substrate and TM complexes in the organic layer. Interestingly, the rate of EtOH oxidation observed via its indirect, Ni(0)-catalyzed release from 110 μmol of 1a in THF/hexane/toluene (2:1:1) is approximately 55% that observed for "instantaneous" release of 110 μmol of EtOH in the same solvent system.

Aqueous Layer Composition

Pyrophosphate buffer is compatible with both enzymes. A basic pH is employed to drive both oxidative equilbria more toward products. This is because three acidic protons are produced in the overall four-electron oxidation of EtOH to acetate by 2 NAD+(see Scheme 1). The 15 mM salt concentration is high enough to permit good buffering, yet low enough to allow for EtOH diffusion into the aqueous layer with a variety of organic layer compositions.

Choice of Enzyme Couple

Figure 3A:
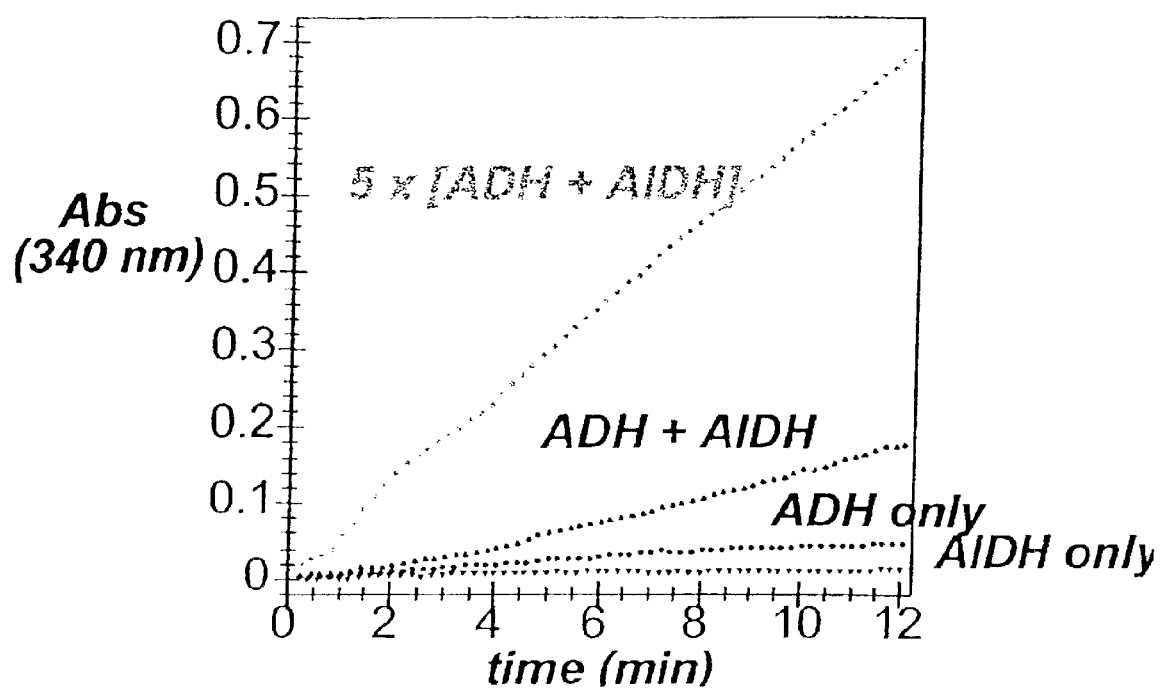
FIGS. 3A and 3B depict screening assay results and spectral authentication of NADH as the species at being observed at 340 nm.

For the screening assay results presented in FIG. 3A, 1×ADH corresponds to the addition of 1.8 microL (0.25) of the stock solution; and 5×ADH corresponds to 9 microL (1.3 U). For the second enzyme, 1×AIDH corresponds to the addition of 11 microL (0.024 U) of its stock solution; and 5×AIDH corresponds to 55 microL (0.12 U).

The AIDH enzyme alone gives no rate, as expected (no acetaldehyde present). Using both AIDH and ADH gives a significantly better observed rate than using the former enzyme alone. Increasing both enzyme concentrations by a factor of five gives a notable increase in observed rate. This effect is largely if not exclusively due to the AlDH concentration, as we have shown in separate control experiments (see below) that ADH is not rate-limiting under that standard ISES conditions reported here, whereas AlDH is partially rate-limiting.

Typical Procedure for TM-Catalyzed Intramolecular Allylic Amination of 1a/b with ISES The aqueous layers are first prepared in the 6 cuvets to be screened, as follows:

| Stock solution | Volume Pipetted | Final Aq. Cuvet Conc. |
|---|---|---|
| 37 mM, NAD+ in 25 mM NaPO$_4$, pH 7 | 180 microL | 7.4 mM |
| Yeast ADH (0.14 U/mL) in 25 mM NaPO$_4$, pH 7 | 9 microL | (1.3 U) |
| Yeast AlDH (0.021 U/10 mL) in 25 mM NaPO$_4$, pH 7 | 55 microL | (0.12 U) |
| 15 mM sodium pyrophosphate, pH 8.8 | 656 microL | Final cuvet: pH 7.7 |

Each cuvet is then sealed with a truncated septum. A seventh control cuvet (double-beam instrument) is used, as well. This cuvet contains the same aqueous layer (900 microL, as described) over which has been layered the organic solvent being used, 400 microl of THF/hexane/toluene (2:1:1) here.

The organic layers are prepared according to the following procedure. Either septum-covered vials or 1.5 mL microcentrifuge tubes may be used. If the latter are chosen, to minimize air contact with the TM complexes, the plastic top is punctured with a 20 Ga needle for each transfer, and the hole resealed each time with electrical tape.

The substrate (110 micromol, 34 mg of 1a) is dissolved in 100 microL of distilled THF in one vial. The ligand (2–4 equivalents relative to TM, depending on the screen; i.e. 12 mg of $PPh_3$ (4 eq. case)) is dissolved in 100 microL of distilled THF in a second vial. To the ligand vial is added TM complex (typically 11 micromol; i.e. 3.0 mg $Ni(COD)_2$-weighed out on an analytical balance in a glove bag) under Ar.* To the ligand/TM mixture is added toluene (100 microL) via syringe.* To the ligand/TM mixture is added LiHMDS (100 microL of a 1.0 M solution in hexane; 0.9 equiv. relative to substrate) via syringe.* The substrate solution (vial one) is now added to the ligand/TM/base solution (vial two), via syringe and then the entire contents of vial two are immediately layered onto the aqueous layer of the appropriate septum-covered quartz cuvet. The absorbance at 340 nm vs. time is recorded for six such cells in parallel, using the thermostat (set to 25° C. for all experiments), automatic, six-cell positioner. (*Indicates that the solution is mixed by vortexing the vial at this stage).

Spectral Authentication of NADH as the Species at Being Observed at 340 nm

Figure 3B:
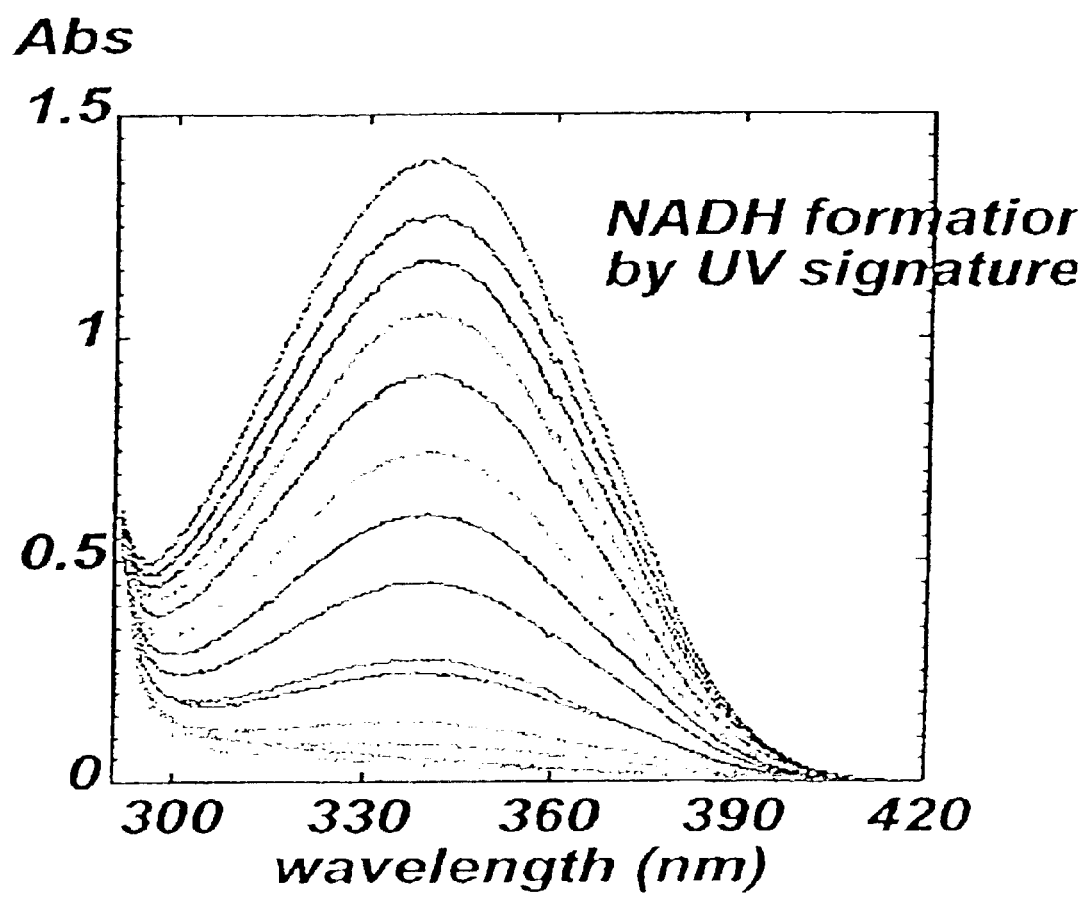

The assay with $Ni(COD)_2/PPh_3/LiHMDS$ is run against the control cuvet with the spectrophotometer in the UV spectral scanning mode. Thus a complete UV spectrum of the aqueous layer is taken every minute. The data are shown in FIG. 3B. Note that, for clarity, only every second UV spectrum is actually displayed (i.e. Spectra shown are at 2 minute intervals). One sees the appearance with time of the characteristic UV spectrum of reduced nicontinamide ($\lambda_{max}$=340 nm) as NADH is formed.

Evaluation of Screening Predictions: Model RB Flask

To assess the correlation between relative rates observed by ISES and actual isolated yields, reactions were run under standard RB flask conditions. While one would not expect a direct correlation here as overall yield and rate are not usually directly proportional, one might expect a qualitative correlation, with relatively fast reactions giving good isolated yields of actual product. Since the EtOH byproduct is what is actually observed in this ISES screen, such a control experiment establishes that the release of EtOH is associated with the desired reaction (allylic amination) as opposed to an undesired side reaction (e.g. simple carbonate ester hydrolysis). Concentrations of substrate 1a (or 1b), TM complex and ligand were as in the ISES screen. However, ca. 75% THF was employed as solvent, with the remainder being hexane from the LiHMDS solution. A full equivalent of LiHMDS was employed. A typical model reaction is outlined below.

To a 25 mL RB flask, fitted with a magnetic stir bar, under Ar, containing $PPh_3$ (25 mg, 96 $\mu$mol) and $Ni(COD)_2$ (6.6 mg, 24 $\mu$mol) in THF (320 $\mu$L) was added a solution of LiHMDS (240 $\mu$L, 1.0 M solution in hexane) dropwise, via syringe, at rt. To this was added, via cannula, a solution of 1a (75 mg, 240 micromol) in THF (320 $\mu$L). The resulting reaction mixture was allowed to stir for 60 min, whereupon the reaction was quenched by addition of $Et_2O$ (5 mL) and saturated, aqueous $NH_4Cl$ (5 mL). After partitioning, the aqueous layer was further extracted with $Et_2O$. The combined organic layers were dried ($MgSO_4$), filtered, evaporated and chromatographed (hexane/EtOAc 1:1) to provide 2a (40 mg, 70%).

Example 1

Transition Metal Catalysts for an Allylic Amination Reaction

The coupling of a synthetic transformation, in situ, to an enzymatic reaction that allows for continuous UV monitoring of the reaction progress is used to identify a hitherto unknown Ni(0)-based method for effecting a cyclization reaction, which is then applied to the synthesis of a class of amino acids that act as PLP-dependent enzyme inhibitors. The intramolecular TM-catalyzed allylic amination reaction illustrated in FIG. 2, as a potentially generalizable route to this class of compounds was investigated. Based on the previous employment of $Pd^0$ catalysts to effect the allylic amination reaction, other late transition metals that might promote such chemistry were studied.

Using a UV spectrophotometer equipped with a standard six-cell changer, six non-Pd TM catalysts were simultaneously monitored for intramolecular allylic amination with model substrates 1a/b in septum-covered quartz cuvets. The reactions were run in a biphasic fashion. The organic chemistry took place in an upper organic layer, above the spectrophotometer beam, and the linked enzymatic chemistry took place in a lower aqueous layer, squarely in the path of the light signal.

Turnover of the ethyl carbonate substrate in the organic layer led to release of ethanol, which diffused into the aqueous layer, where it underwent enzymatic oxidation with concomitant formation of NADH ($\lambda_{max}$=340 nm). A coupled alcohol dehydrogenase (ADH)/aldehyde dehydrogenase (AIDH) enzyme assay was found to be optimal for screening.

Turning to FIG. 3A, UV traces showing dependence of NADH formation rate upon enzymatic couple used was observed. In FIG. 3B, a clear spectroscopic signature indicating that NADH is the species giving rise to the 340 nm absorbance increase was observed. All traces are for the reaction depicted in FIG. 2. The spectral scans are at 2 minute intervals. The AIDH only experiment is a negative control and shows no rate, as expected.

Among a spectrum of non-Pd complexes screened, the most favorable results for the cyclization of 1a to 2a were obtained with Ni(0) catalysts. In this cyclization, a lithiated carbamate was employed as intramolecular nucleophile.

Figure 4A:
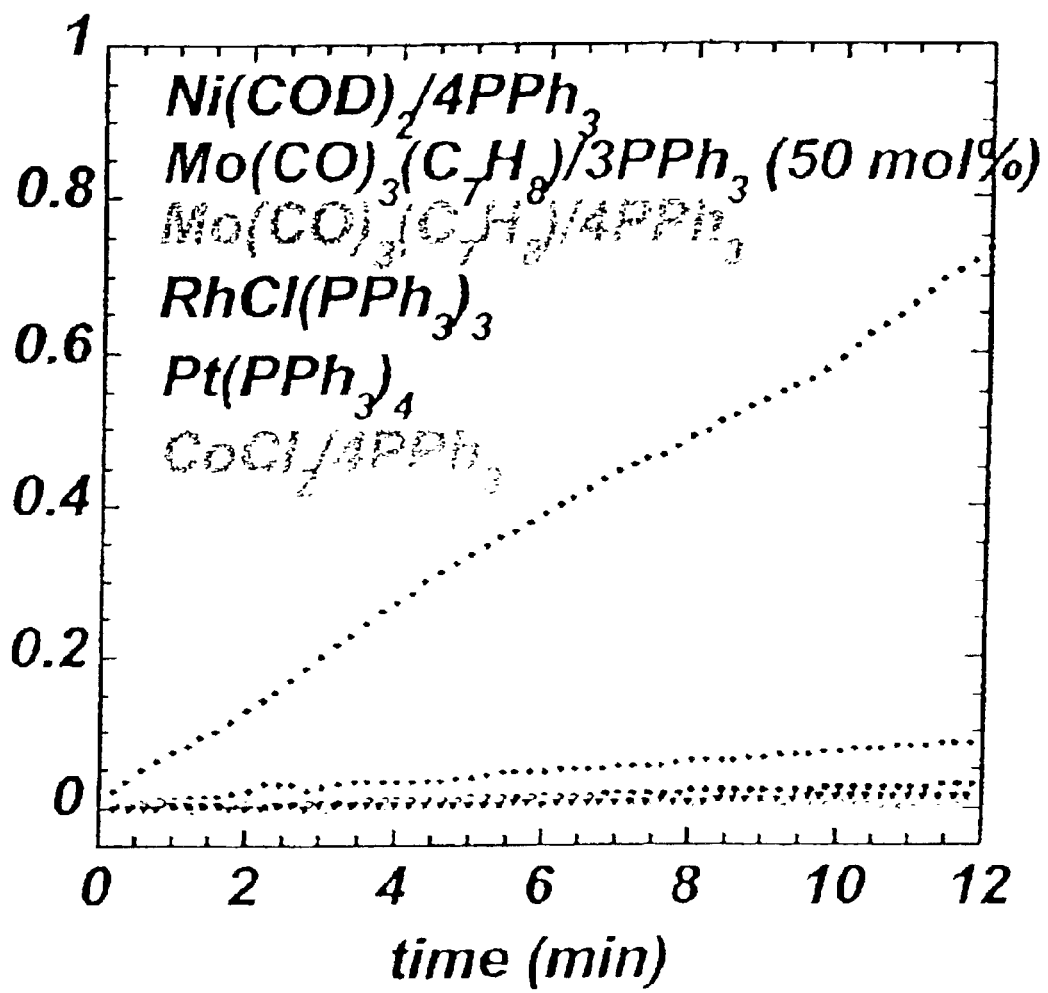
FIGS. 4A and 4B depict results for screening of six assays simultaneously.
Figure 4B:
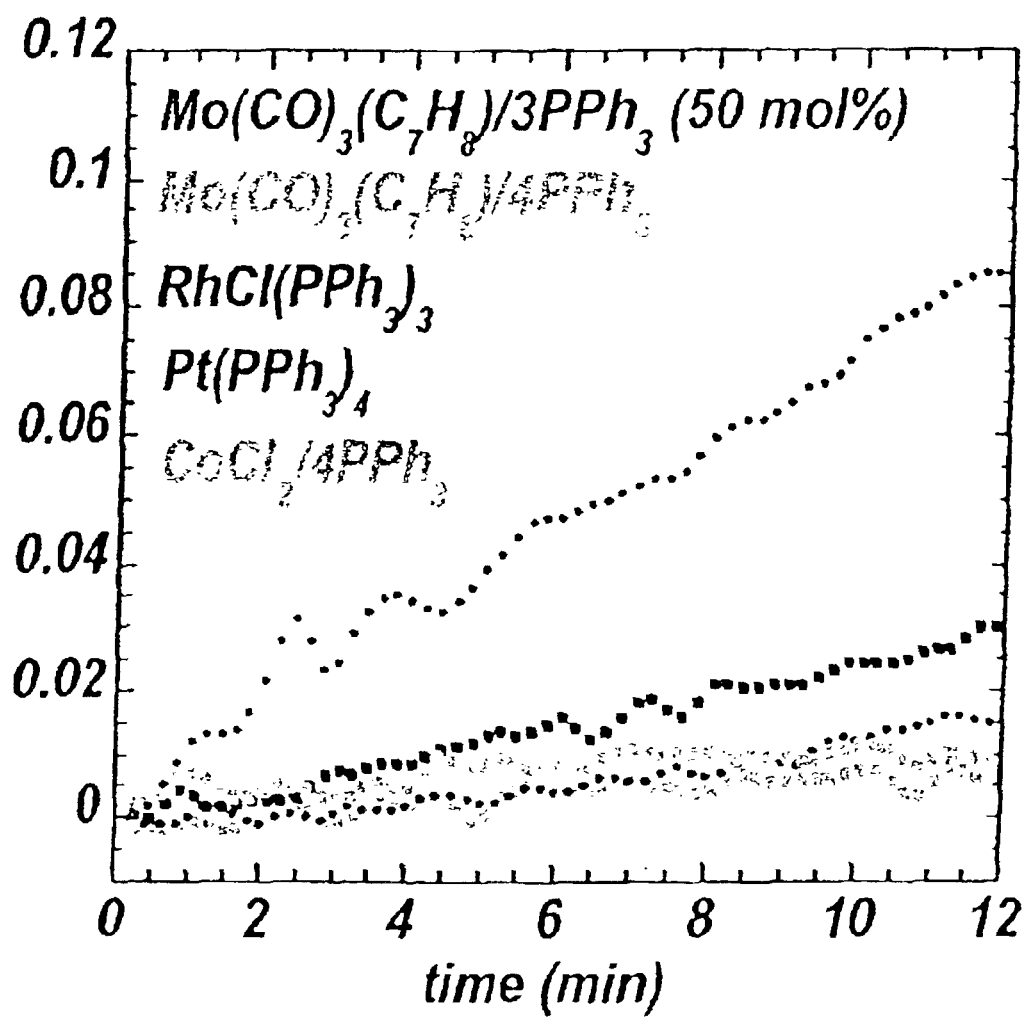

As evidenced from FIG. 4, six reactions can be screened simultaneously, and one can obtain meaningful relative kinetic data within 10 minutes. Importantly, ISES proves to be a useful predictive tool. Thus, there is a good correlation between $NAD^+$ and reduction rates observed in the biphasic cuvet assay and efficiency of the corresponding allylic amination observed in an RB flask in neat THF. The screen also uncovered the first Mo(0)-mediated allylic amination of which we are aware.

UV traces (above) showing the relative rates of turnover of substrate 1, as inferred from enzymatically coupled EtOH oxidation. For each metal, the table below provides a comparison between the NADH-formation rate observed in the cuvet screen and isolated yield of 2 for the same reaction run in an RB flask.

| Catalyst | Slope (mAbs/min)[a] | Isolated Yield |
|---|---|---|
| $Ni(COD)_2/4PPh_3$ | 58[b] | 70% |
| $Ni(COD)_2/4PPh_3$[c] |  | (89%) |
| $Mo(CO)_3(C_7H_8)/3PPh_3$[d] | 6.8 | 18% |

| Catalyst | Slope (mAbs/min)[a] | Isolated Yield |
|---|---|---|
| Mo(CO)$_3$(C$_7$H$_8$)[c] | | (35%)[f] |
| Mo(CO)$_3$(C$_7$H$_8$)/4PPh$_3$ | 0.6 | |
| P(PPh$_3$)$_4$ | 2.5 | 15%[g] |
| RhC(PPh$_3$)$_3$ | 1.5 | ~5%[e] |
| Co(Cl)$_2$4 PPh$_3$[d] | 0.7 | |

[a]Slopes of linear least squares fit lines to the UV traces shown above.
Note:
The entries in parentheses represent RB flask results only, run at higher catalyst loadings.
[b]For this entry, three runs gave values of 55, 58 and 60 mAbs/min, consistent with an experimental uncertainty in the ±5–15% for these ISES slopes.
[c]Reaction run at 20 mol % catalyst.
[d]In both the cuvet and the RB flask, this reaction was run on 1b at 138 nM substrate (half the ususal concentration) and at 50 mol % catalyst.
[e]Reaction run on 1b at 100 mol % catalyst at the ususal concentration (275 mM).
[f]These cases showed little to no product crude $^1$H NMR.
[g]For the Pt(0)-catalyed reaction, the rate observed by ISES increases somewhat beyond the inital 12 min window.

Example 2
Ligand and Nitrogen Protecting Group Dependence of TM-Catalyzed Allylic Displacements ISES was employed to probe the ligand and nitrogen protecting group (PG) dependence of this reaction. The results are shown in the table below and correspond to screening data assimilated from three sets of 6-cuvet runs (i.e. 3×10 min of UV data collection). Electron rich N-protecting groups promote the Ni(0) allylic amination, with the PMP (para-methoxyphenyl) group giving the best rates. This PG was retained for the ligand screens, which turned up three hits: dppb (1,4-bis(diphenylphosphino) butane), PPh$_3$, dppf (diphenylphosphino ferrocene).

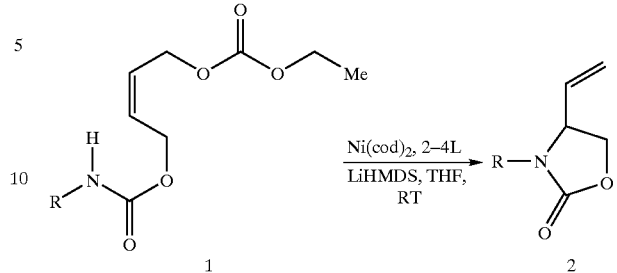

| Ligand | N-Protecting Group (R) | Slope[a] (mAbs/min) |
|---|---|---|
| PPh$_3$ | H (no protection) | 7 |
| PPh$_3$ | CHPh$_2$ (benzhydryl) | 9 |
| PPh$_3$ | C$_6$H$_2$-3,4,5-(OMe)$_3$ | 18 |
| PPh$_3$ | C$_6$H$_4$-p-NO$_2$ (PNP) | 0.2 |
| PPh$_3$ | CO$_2$t-Bu (Boc) | 1 |
| PPh$_3$ | C$_6$H$_4$-p-OMe (PMP) | 35 |
| P(OMe)$_3$ | C$_6$H$_4$-p-OMe (PMP) | 1 |
| P(2,6-di-OMe—C$_6$H$_3$)$_3$ | C$_6$H$_4$-p-OMe (PMP) | 7 |
| AsPh$_3$ | C$_6$H$_4$-p-OMe (PMP) | 0.3 |
| 2,2'-CH$_2$—(4S)—Ph-box[b] | C$_6$H$_4$-p-OMe (PMP) | 0.6 |
| dppf[c] | C$_6$H$_4$-p-OMe (PMP) | 26 |
| P(C$_6$H$_4$-p-NMe$_2$)$_3$ | C$_6$H$_4$-p-OMe (PMP) | 1 |
| P(C$_6$F$_5$)$_3$ | C$_6$H$_4$-p-OMe (PMP) | 0.3 |
| Ph$_2$P(CH$_2$)$_4$PPh$_2$ | C$_6$H$_4$-p-OMe (PMP) | 118 |
| P(2-fur)$_3$ | C$_6$H$_4$-p-OMe (PMP) | 0.4 |
| P(t-Bu)$_3$ | C$_6$H$_4$-p-OMe (PMP) | 0.4 |

[a]Slopes of least-squares fitted lines to the Abs vs. time data over ca. 10 min
[b]2,2'-methylenebis[(4S)-4-phenyl-2-oxazoline]
[c]1,1'bis(diphenylphosphino)ferrocene.

Figure 5:
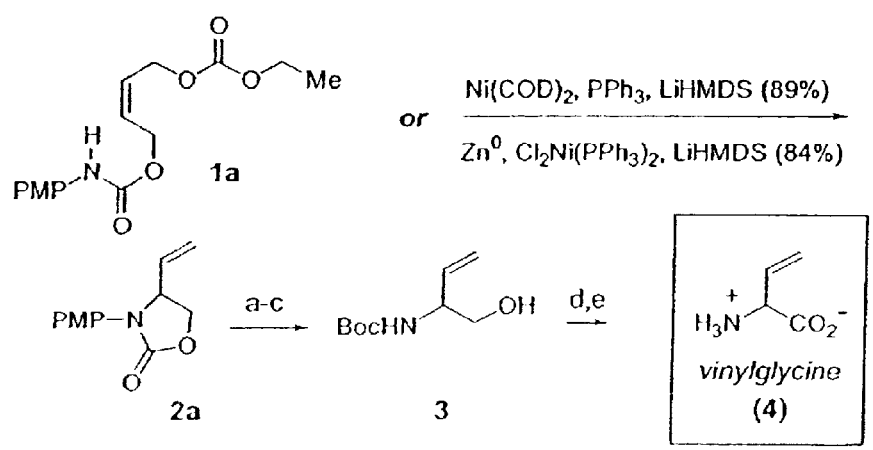
FIG. 5 depicts ISES-optimized Ni(0)-mediated allylic amination for the synthesis of vinylglycine.

The ISES-optimized Ni(0)-mediated allylic amination conditions were then applied to a synthesis of vinylglycine, a known inactivator of PLP-dependent transaminases for L-aspartate, L-alanine, L-serine and D-alanine (FIG. 5). It is both noteworthy that the key intramolecular allylic amination step proceeds in excellent yield and that the PPh3-ligated Ni(0) catalyst may be generated either via ligand exchange from Ni(COD)$_2$ or via Zn-mediated reduction of the corresponding dichloro-Ni(II) complex.

Figure 6:
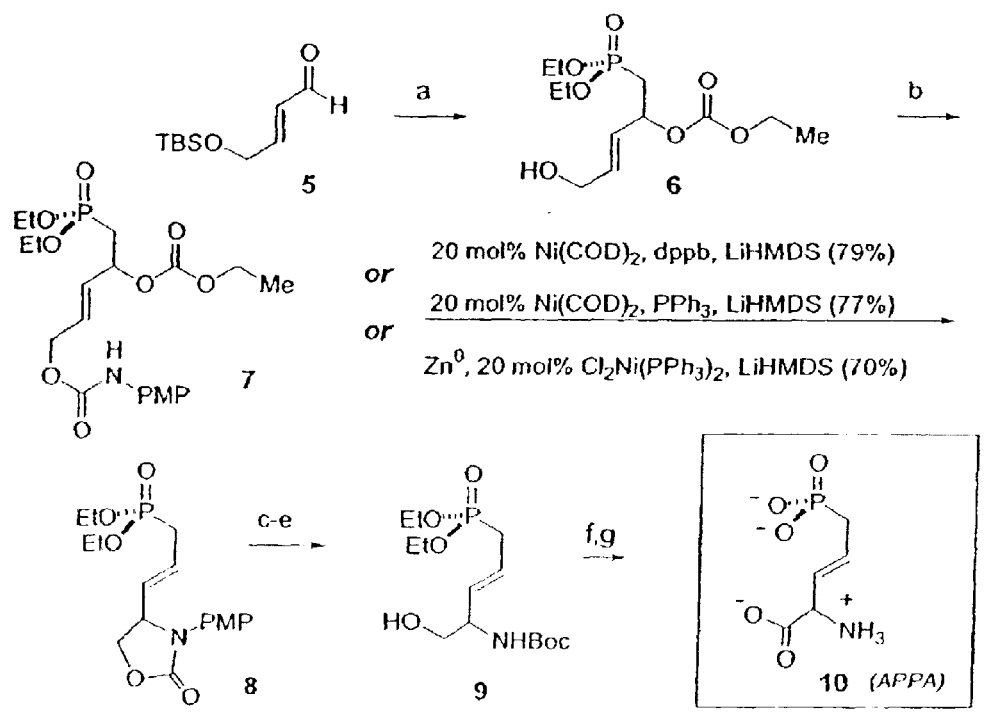
FIG. 6 depicts the synthesis of E-2-amino-5-phosphono-3-pentenoic acid

The same strategy led to an expeditious synthesis of E-2-amino-5-phosphono-3-pentenoic acid (APPA, see FIG. 6). This β,γ-unsaturated phosphonate mimic of homoserine phosphate has been shown recently to inhibit two PLP-dependent enzymes, cystathionine γ-synthase (tight-binding reversible inhibitor; $K_i$=27 μM) and threonine synthase (irreversible inhibitor; $K_i$=400 microM; $k_{inact}$=0.25 min$^{-1}$).

The requisite α-phosponomethyl allylic carbonate 7 could be assembled in short order from aldehyde 5. Three operations were carried out in one pot initially. Aldehyde 5 was condensed with diethyl lithiomethylphosphonate at low temperature, followed sequentially by alkoxide trapping with ethyl chloroformate, and in situ desilylation (addition of dilute HCl and warming to room temperature). Pleasingly, with either dppb or TPP as ligand, the key Ni(0)-mediated allylic amination proceeded both efficiently and stereoselectively, yielding solely the E geometric isomer of 8.

In this regard, it is particularly noteworthy that the reaction studied here, though presumably both water- and air-sensitive, is still amenable to screening by this biphasic version of the ISES approach.

Figure 2:
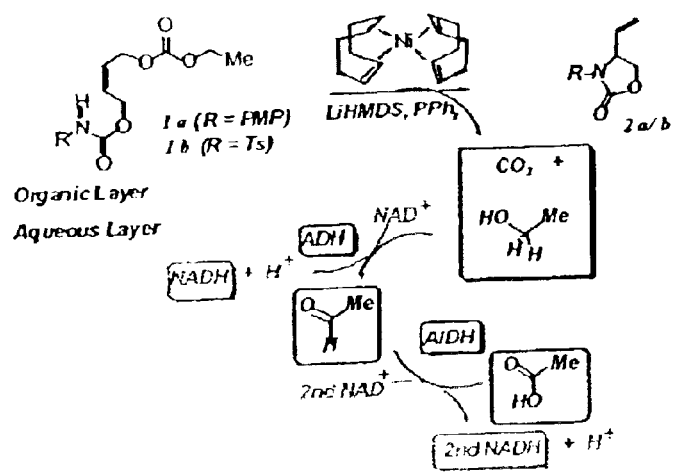
FIG. 2 depicts an intramolecular TM-catalyzed allylic amination reaction.

Example 3
Comparison of Relative Initial Rates of Reaction as Measured by a Time Point Assay (NMR Quantitation) vs. the Continuous ISES Assay A time point assay (quench/work-up/NMR analysis) was undertaken in order to compare the relative rates obtained for the Ni⁰- and Mo⁰-catalyzed allylic aminations with those obtained in the continuous ISES assay. For each reaction, two trials were carried out. As shown below, the time point assay estimates that the Ni⁰-promoted reaction proceeds at a rate 8.7–13 times faster than the Mo⁰-mediated reaction under the conditions used for the ISES screen (gives a relative rate ratio of 8.5–13; FIG. 2 from article).

A. For the Ni⁰ Catalyzed Reaction:

Trial 1: To a solution of 1a (68 mg, 220 µmol) dissolved in THF (200 µL) was added a solution of Ni(COD)₂ (6.0 mg, 22 µmol), triphenylphosphine (24 mg, 88 µmol) and LiHMDS (1 M in hexanes, 200 µL) in THF (200 µL)/toluene (200 µL). This was immediately layered over sodium pyrophosphate buffer (1.8 mL, 15 mM, pH 8.8) in a 2 mL volumetric flask (~2.8 mL total capacity), sealed with a septum and agitated using the same six-cell changer used for our ISES assays in the UV spectrophotometer.

For each time point, 100 µL of the reaction mixture was withdrawn using a microliter syringe and quenched with a mixture of saturated aqueous NH₄Cl (100 µL) and methanol (100 µL). Following extraction with EtOAc (200 µL), a 100 µL aliquot of the organic extract was withdrawn, mixed with 2'-acetonaphthone (0.45 µmol; 5 µL of a 0.09 M solution) as the internal standard for NMR.

After evaporation of the volatiles (rotary evaporator, HV pump) of CDCl₃ (500 µL) was added to each sample and a ¹H NMR spectrum acquired. The concentration of product was calculated by comparing the integrals of the NMR signals at δ 2.87 (H₃CCO— standard, 3H) and 5.4–5.5 (H₂C=CH— 2a product, 2H).

Trial 2: This experiment involves the same amounts of all reactants as in trial 1, but differs in order of addition. The organic phase was layered upon the aqueous buffer phase, and then the substrate solution was added to initiate the reaction. In the previous experiment, the substrate was added to the organic layer (containing all components) immediately before layering.

Thus, Ni (COD)₂/PPh₃ dissolved in THF:toluene (200 µL: 200 µL) and LiHMDS (200 µL, 1M in hexanes) was first layered over the buffer layer (1.8 mL) and then 1a in THF (200 µL) was added to the organic layer. For each time point, a 100 µL aliquot was withdrawn, quenched, worked up and analyzed as in Trial 1.

B. For the Mo⁰ Catalyzed Reaction:

A solution of Mo(CO)₃cycloheptatriene (15 mg, 56 µmol) in THF:toluene (200 µL: 200 µL) and LiHMDS (110 µL, IM in hexanes) was first layered over the sodium pyrophosphate buffer layer (1.8 mL, 15 mM, pH 8.8) in a 2 mL volumetric flask (~2.8 mL total capacity), sealed with a septum. Then a solution of 1b (39 mg, 110 µmol) and PPh₃ (44 mg, 168 µmol) in THF:hexanes (200 µL: 90 µL) was added to the organic layer and agitated using the same six-cell changer used for ISES assays in the UV spectrophotometer. For each time point, a 100 µL aliquot was withdrawn, quenched, worked up and analyzed as in Trial 1 of Ni⁰ catalyzed allylic amination reaction. In this case, the concentration of product was calculated by comparing the integrals of the NMR signals at δ 2.87 (H₃CCO— standard, 3H) and 5.5–5.6 (H₂C=CH— 2b product, 2H).

Example 4

Ligand Dependence of Rh'-Mediated Intermolecular Allylic Amination with a Simple Substrate The aqueous layers were first prepared in the 6 cuvets identical to the typical composition as stated in the section "Typical Procedure for TM-catalyzed Intramolecular Allyic Amination of 1a/b with ISES".

Figure 7:
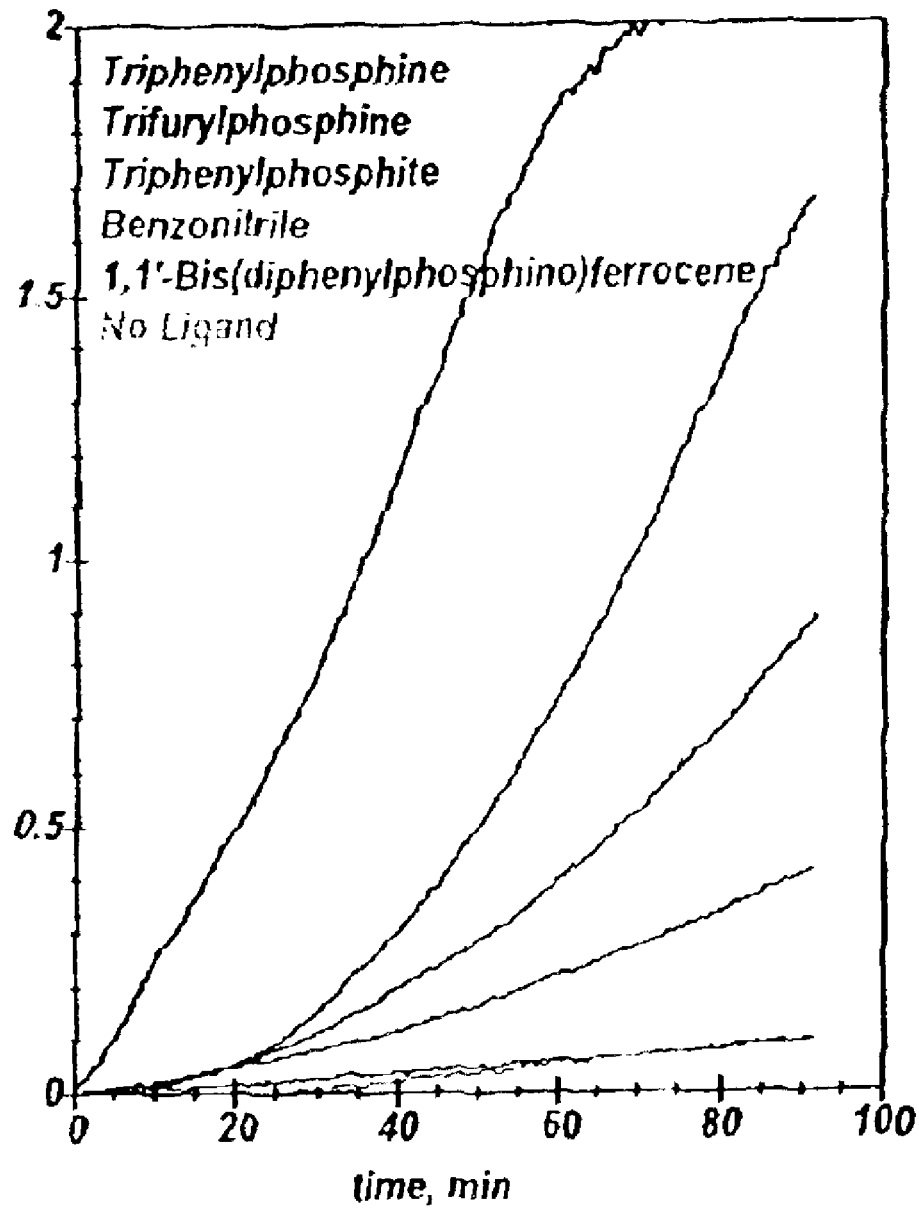
FIG. 7 depicts the absorbance at 340 nm vs time for six parallel for reactions.

The organic layer was prepared according to the following procedure: The substrate allyl ethyl carbonate (26 mg, 200 µmol) was dissolved in 100 µL of distilled THF in one vial. The ligand (2 or 4 equivalents (for bidentate or monodentate ligands respectively) relative to the TM) was dissolved in 300 µL of distilled THF in one vial. To the ligand vial was added the TM (Rh') as (Rh(COD)Cl)₂ (2 mg, 4 µmol). To the TM/ligand vial was then added the nucleophile (dibenzylamine, 59 mg, 300 µmol), and the resultant mixture vortexed. To 300 µL of the TM/ligand/nucleophilic amine mixture was then added 100 µL of the substrate solution via a syringe. Then the combined mixture was layered over the aqueous layer in the septum covered cuvette via a syringe. The absorbance at 340 nm vs time was thus recorded in parallel for six such cuvets which differ only in the type of ligand for Rh'. For the selected ligand distribution, kinetic profiles were obtained over a longer time scale as shown below (FIG. 7).

The rate profiles for Rh' catalysis of this intermolecular version of the allylic amination parallel the experimental results of P. A. Evans that identifies Rh' as a newly discovered TM catalyst for allylic amination purposes.

Example 5

Extent to which the Enzymatic Step(s) are Partially Rate-Limiting

The Ni⁰-catalyzed allylic amination of 1a.

Top Organic layer: In all experiments, the upper organic layer had the same composition as in the Typical Procedure for TM-Catalyzed Intramolecular Allylic Amination with ISES.

Figure 8:
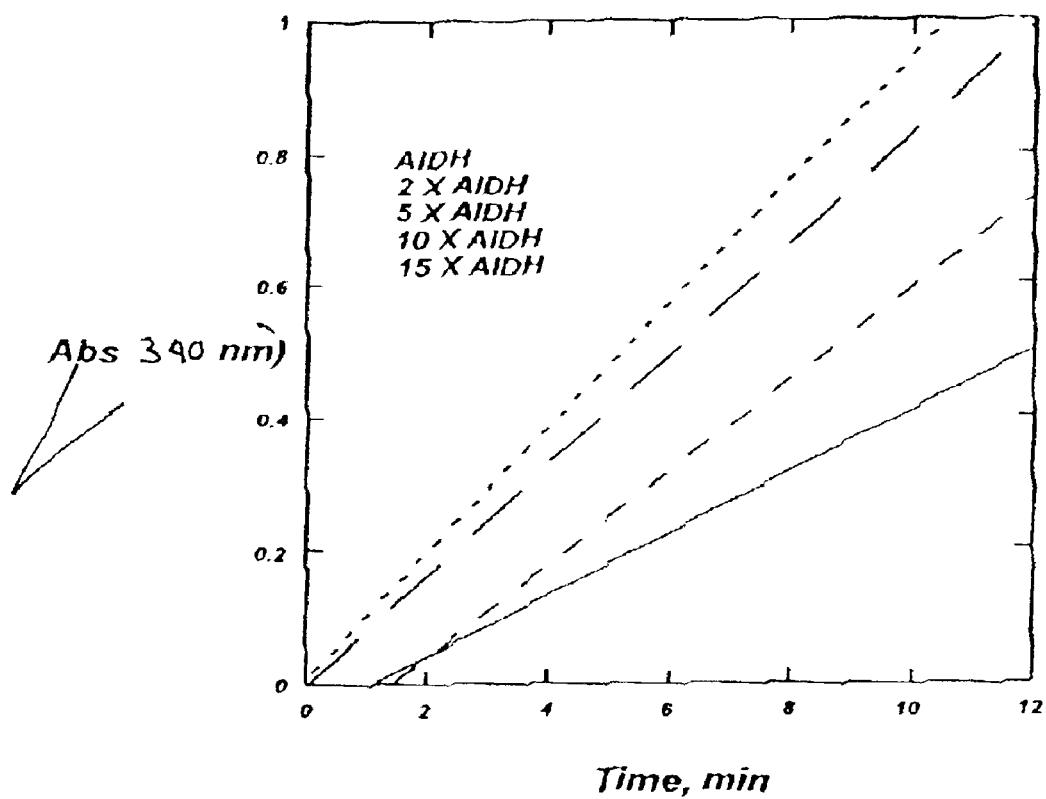
FIG. 8 depicts the absorbance at 340 nm vs time for parallel reactions.

A. Variation of AlDH:

Bottom Buffer layer (For Varying AlDH at Constant ADH): For each trial, β-NAD⁺ (180 µL of a 37 mM stock sol'n; 7.4 mM final conc. in the aqueous layer) and ADH (29 µL of a 0.045 U/µL stock sol'n; 1.3 U) concentrations were held fixed. AlDH concentration was varied by taking 4, 8, 20, 40, 60 µL (0.006 U/µL stock sol'n) in five separate runs. In all cases, the final volume of the aqueous layer was adjusted to 900 µL with buffer (sodium pyrophosphate, 15 mM, pH 8.8). The final assay pH was adjusted to 7.7, wherever necessary with a 1M NaOH solution. See FIG. 8.

| | Varying AlDH at ADH = 1.3 U | |
|---|---|---|
| | AlDH (U) | Slope (Abs min⁻¹) |
| 1 | 0.024 | 0.022 ± 0.002 |
| 2 | 0.048 | 0.052 ± 0.008 |
| 3 | 0.120 | 0.076 ± 0.014 |
| 4 | 0.240 | 0.090 ± 0.004 |
| 5 | 0.360 | 0.097 ± 0.004 |

Thus with the use of 1.3 U of ADH under the standard ISES conditions reported here, variation of AlDH level from 0.024 U to 0.360 U shows that the rate of NADH formation observed levels off at 0.24 U (showing that the AlDH-mediated step is no longer partially rate-limiting when 0.24 U or more of the enzyme is present).

4B. Variation of ADH:

Bottom Buffer layer (For Varying ADH at Constant AlDH): For each trial, β-NAD (180 µL of a 37 mM stock solution; 7.4 mM final aq. cuvet conc) and AlDH (180 µL of a 0.0033 U/µL; 60 U as aq. cuvet conc) were used as constant amounts. ADH (0.14 U/µL stock solution) of varying amounts (9 and 45 µL) was used in two separate recordings of absorbance (340 nm) vs time. In both cases, the final volume of the aqueous layer was adjusted to 900 µL with buffer (sodium pyrophosphate, 15 mM, pH 8.8). The final assay pH was 7.7.

By using 0.6 U of AlDH, we are well above the rate-limiting threshold for this second enzyme (see previous experiment). So, this experiment serves to directly measure the extent to which the first enzyme (ADH) is partially rate-limiting at its standard ISES assay concentration. Since, essentially no rate change (increases by 11%, which is within the experimental uncertainty) is observed upon increasing ADH conc. 5× beyond its normal level, the ADH-step is not at all rate limiting here.

| Varying ADH at AlDH = 0.60 U | | |
|---|---|---|
| | ADH (U) | Slope (Abs min$^{-1}$) |
| 1 | 1.30 | 0.115 ± 0.017 |
| 2 | 6.50 | 0.128 ± 0.021 |

Under the standard conditions selected for this ISES screen, the ADH-mediated step is not at all rate-limiting, but the AIDH-mediated step is partially rate-limiting. The data indicate that if care is taken to reproducibly add the same amount of AIDH to each cuvet (0.12 U was used in standard ISES assay), good relative rate data can be obtained. The control experiments performed here suggest that experimental uncertainties might be reduced even further if more AIDH is expended per assay.

Example 6
Test for Level of Water Diffusing into the Organic Layer by Karl Fischer Titration A Karl Fischer titration was performed using the coulometric method with a calibrated Metrohm 684 KF coulometer. An aliquot of the organic solvent layer in question was taken up via syringe, and the syringe capped. It was then weighed on a high precision (five places beyond the decimal) Mettler balance. Following injection of the sample into the coulometer cell, the re-capped syringe was again weighed, to calculate the total sample weight. About one minute was usually sufficient to obtain a stable coulometer reading for the weight of water present in the sample. The Karl Fischer method is based on the oxidation of $SO_2$ by iodine using the residual water in the sample. Two types of organic layer samples were subjected to such analysis.

A. Initial Organic Solvent Layer

A sample of the THF:hexanes:toluene (2:1:1) mixture used in the ISES assay, when injected to the electrolytic cell, showed a residual water content of 0.09% or 41 mM (see data below). This gives an estimate of the initial water content in the organic layer prior to the allylic amination reaction.

B. Organic Solvent Layer in the Biphasic Assay System

A portion of the THF:hexanes:toluene (2:1:1) solvent mixture (4 mL total) was agitated over a sodium pyrophosphate buffer layer (15 mM, pH 8.8; 9 mL total) for 10 min. When an aliquot of this organic solvent layer was injected into the electrolytic cell, it showed a residual water content of 1.1% or 506 mM. This gives an estimate of the final water content in the organic layer after 10 min under the usual ISES assay conditions.

To take into account experimental uncertainty in sample preparation, as well as analysis, each type of organic layer was prepared in triplicate, and each such sample assayed in duplicate. This led to 6 readings of % water for each type of organic layer.

A representative table of Karl Fischer results is presented below:

| Sample | | | Syringe wgt. before injection (mg) | Syringe wgt. after injection (mg) | Weight of sample injected (mg) | Karl Fischer Reading (μg) | Percentage residual water (wt/wt) |
|---|---|---|---|---|---|---|---|
| A. | a) | i) | 85.69 | 17.72 | 67.97 | 48.5 | 0.07 |
| | | ii) | 78.62 | 12.58 | 56.04 | 64.7 | 0.12 |
| | b) | i) | 64.22 | 21.62 | 42.60 | 50.7 | 0.12 |
| | | ii) | 123.65 | 14.92 | 108.73 | 78.3 | 0.07 |
| | c) | i) | 87.78 | 5.67 | 82.11 | 84.1 | 0.10 |
| | | ii) | 92.24 | 5.80 | 86.44 | 71.1 | 0.08 |
| B. | a) | i) | 50.64 | 4.97 | 45.67 | 463 | 1.01 |
| | | ii) | 95.62 | 5.52 | 90.12 | 886 | 0.98 |
| | b) | i) | 58.67 | 13.03 | 45.64 | 497 | 1.09 |
| | | ii) | 53.40 | 13.97 | 39.43 | 444 | 1.13 |
| | c) | i) | 72.46 | 20.58 | 51.88 | 623 | 1.20 |
| | | ii) | 34.15 | 10.33 | 23.82 | 284 | 1.19 |

Example 7
Effect of $CH_3CHO$ on the TM-Catalyzed Allylic Amination Rate

The $Ni(cod)_2/PPh_3$ catalyzed intramolecular allylic amination reaction of 1a was chosen for this study.

A. Direct Addition to Buffer Layer: $CH_3CHO$ (10 μL of a 10 mM solution in deionized water; 0.11 mM final aq cuvet conc) was added via a microliter syringe to the lower buffer layer, at 11.6 min after the start of $Ni^0$ catalyzed intramolecular allylic amination reaction of 1a in the top organic layer of the cuvet (this reaction of 1a catalyzed by $Ni(cod)_2/PPh_3$ is identical to that described in the section Typical Procedure for TM-Catalyzed Intramolecular Allylic Amination). The normal rate profile (ADH-AlDH-NAD biphasic ISES assay) for the $Ni^0$ catalyzed reaction showed a sharp rise in absorbance (resulting from rapid oxidation of the added $CH_3CHO$ to acetic acid) followed by gradual return to the rate prior to the addition.

Figure 9:
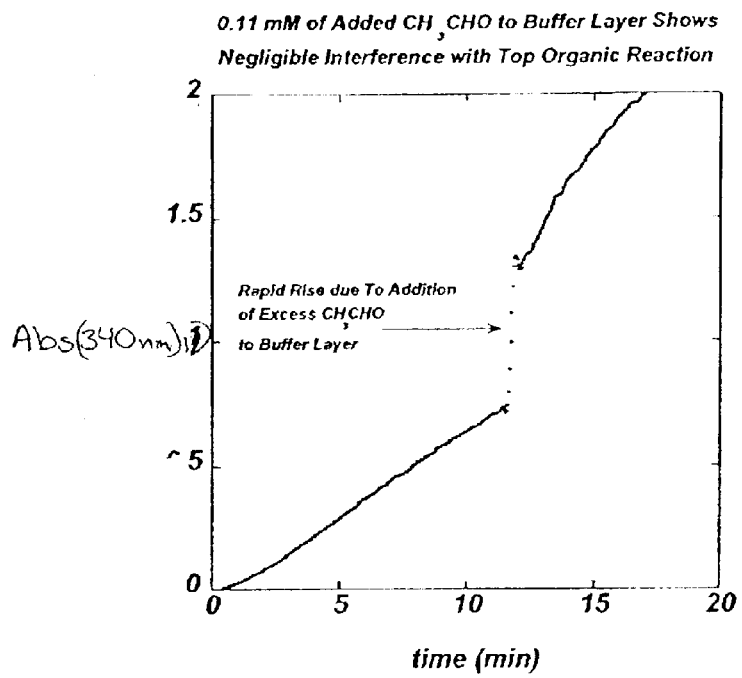
FIG. 9 depicts that addition of $CH_3CHO$ to buffer layer has negligible interference with organic reaction.

See FIG. 9.

B. Addition to Organic Layer (Use of a ADH-APAD Assay):

The buffer layer is prepared as follows:

| Stock solution | Volume Pipetted | Final Aq. Cuvet Conc |
|---|---|---|
| 37 mM, APAD in 25 mM NaPO$_4$, pH 7 | 50 μL | 2.1 mM |
| Yeast ADH (0.11 U/μL) in 25 mM NaPO$_4$, pH 7 | 12 μL | 1.3 U |
| 15 mM sodium pyrophosphate, pH 8.8 | 838 μL | |
| Final assay pH was 7.7. | | |

Figure 10:
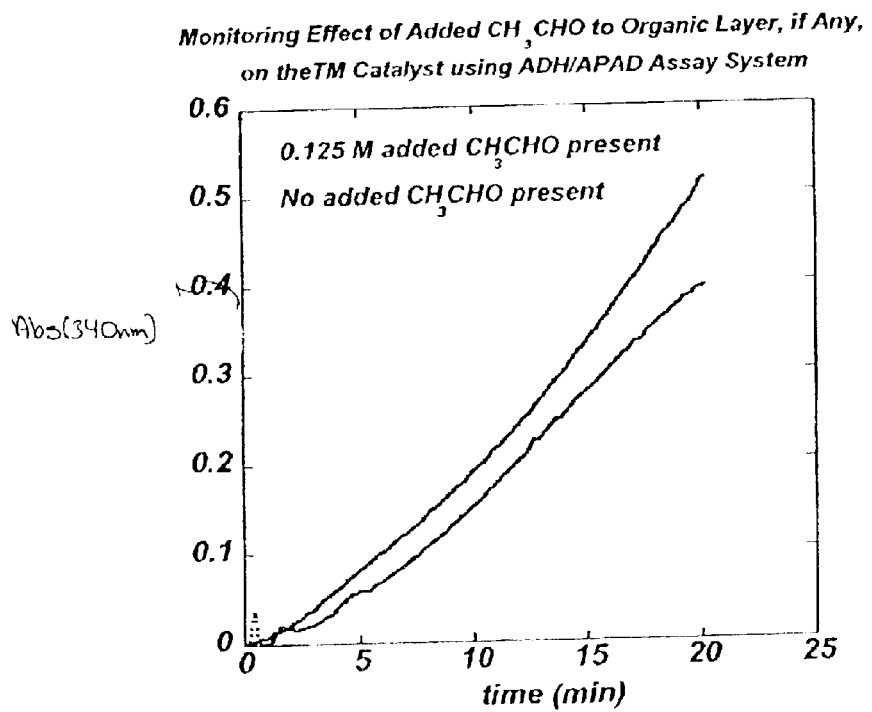
FIG. 10 depicts monitoring effect of added $CH_3CHO$ to organic layer on a TM catalyst using ADH/APAD assay system.

The organic layer is identical in scale and composition to that in the $Ni(COD)_2/PPh_3$ catalyzed intramolecular allylic amination reaction of 1a described under Typical Procedure for TM-Catalyzed Intramolecular Allylic Amination. This formed the top layer in the cuvet. Two consecutive runs were made in duplicate:

a) The absorbance at 365 nm vs time is recorded first without any added $CH_3CHO$. Slope obtained was: 0.020±0.004 Abs min$^{-1}$; b) In the second run $CH_3CHO$ (50 μL of a 1 M solution in toluene; 0.125 M final concentration in the organic layer) was added to the organic layer immediately following the addition of 1a and increase in absorbance at 365 nm vs. time was recorded. Slope obtained was: (0.020±0.005 Abs min$^{-1}$. See FIG. 10. Hence, no inhibitory effect of added $CH_3CHO$ on the rate of $Ni^0$ catalyzed intramolecular allylic amination reaction of 1a was observed.

Experiment B serves as a more stringent test of potential acetaldehyde interference with the Ni⁰-mediated allylic substitution reaction where the acetaldehyde was introduced directly into the organic layer. Since a much higher concentration of acetaldehyde was considered for this addition, the second reporting enzyme, AlDH, was removed. This would prevent the formation of a huge NADH spike from oxidation of the acetaldehyde. For this purpose, a single reporting enzyme was employed by simply substituting APAD⁺(3-Acetylpyridine Adenine Dinucleotide) in place of NAD⁺. APAD⁺(redox potential=−258 mV, $\lambda_{max}$=365 nm) is a better oxidizing agent than NAD⁺ (redox potential=−320 mV) and so, though a bit more costly, provides for a single enzyme assay of released EtOH that gives acceptable rates. Even when 50 μmol of acetaldehyde was added directly to the organic layer, no reduction in the rate of NADH oxidation (of released EtOH) was observed. This experiment indicates that even 125 mM concentrations of acetaldehyde in the organic layer apparently do not interfere with the Ni⁰-mediated allylic substitition reaction under study.

Example 8

Test for Enzyme Inhibition by TM Catalysts in the Organic Layer

Figure 11:
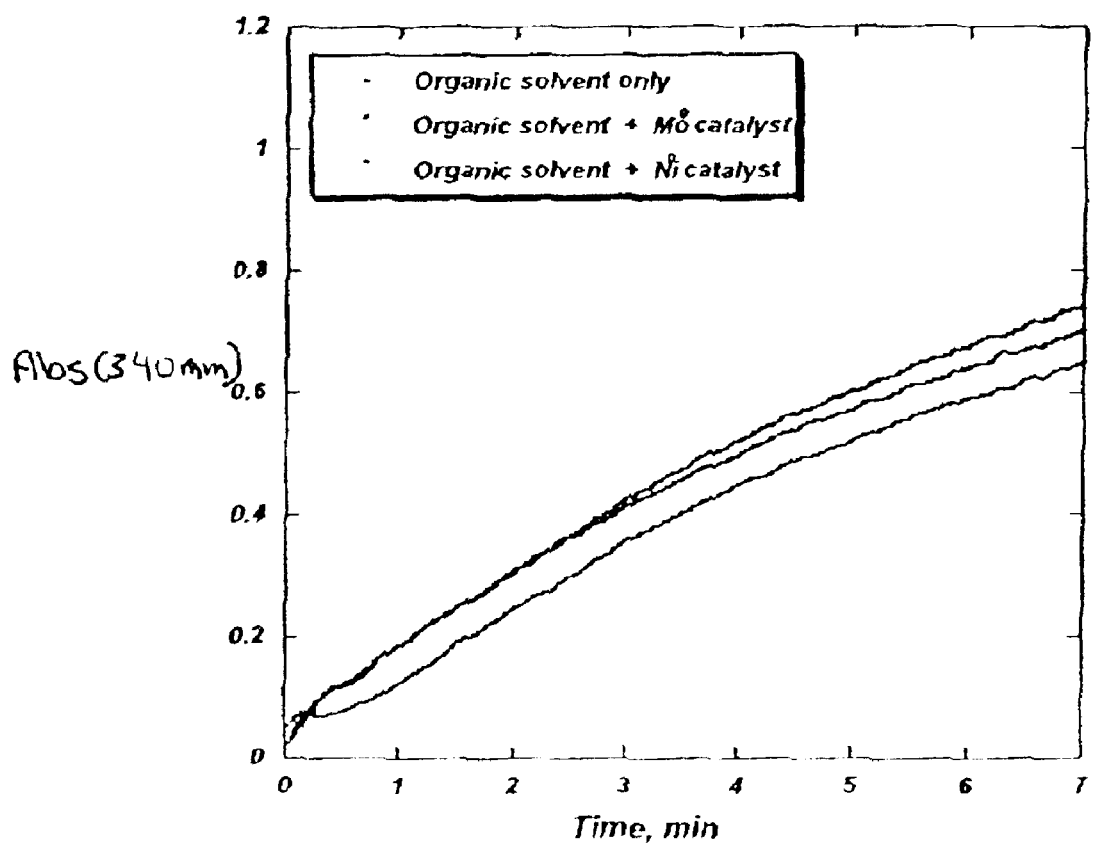
FIG. 11 depicts the effect of TM catalyst in organic layer upon enzyme activity in aqueous layer.

In order to assess the possible effect of a TM complex in organic layer upon enzyme activity in the neighboring organic layer, the following control experiment was performed. Two cuvets—one containing TM complex-ligand and the other containing only solvent in the organic layer were compared side-by-side for their relative rates of EtOH oxidation in the aqueous layer. The control cuvet contained a 400 μL organic layer composed exclusively of solvent (THF:toluene:hexane 2:1:1) and a 900 μL aqueous layer identical to that of a typical screen (vide supra). The TM-cuvets also contained either 11 μmol [Ni(cod)₂]/4 PPh₃ or 55 μMol [Mo(C₇H₈)(CO)₃ ]/3 PPh₃, but were otherwise identical to the control cuvet. Reactions were initiated by injection of 0.18 μmol (200 μM final conc in the aqueous layer) of EtOH into the buffer layer. No inhibition of the rate of formation of NADH was seen in the cuvets containing either the Ni⁰ complex or the Mo⁰ complex. See FIG. 11.

Synthetic Chemistry

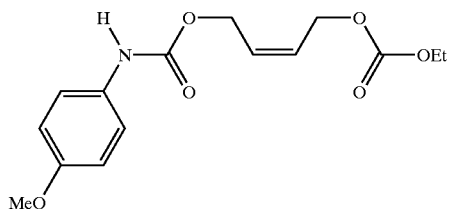

Ethyl (2Z)-4-[(p-methoxyanilino)carbonyloxyl-2-butenyl Carbonate (1a). To a solution of ethyl (2Z)-4-hydroxy-2-butenyl carbonate[1] (5.13 g, 32 mmol) in THF (40 mL) at 0° C. were added sequentially pyridine (3.89 mL, 48 mmol) and p-methoxyphenyl isocyanate (6.23 mL, 48 mmol) via syringe. The solution was allowed to warm slowly to rt over 12 h. Ethyl ether was added into the reaction mixture and the organic was washed with saturated CuSO₄ solution. After drying (MgSO₄), filtration and evaporation, the crude product was purified by SiO₂ chromatography (33→50% EtOAc-hexanes) to provide 1a (9.67 g, 98%): ¹H NMR (300 MHZ, CDCl₃) δ1.28 (t, J=7 Hz, 3H), 3.75 (s, 3H), 4.18 (q, J=7 Hz, 2H), 4.71–4.76 (m, 4H), 5.72–5.84 (m, 2H), 6.75 (br s, 1H), 6.79–6.84 (m, 2H), 7.26 (br d, J=7 Hz, 2H); ¹³C NMR (75 MHZ, CDCl₃) δ14.2, 55.5, 60.4, 63.0, 64.1, 114.1, 120.7, 127.3, 128.8, 130.7, 153.5, 154.9, 156.0; HRMS (FAB, 3-NBA) calculated for C₁₅H₁₉NO₆ [(M+H)⁺] 310.1290, observed 310.1282; [M⁺] 309.1212, observed 309.1211.

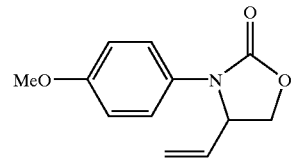

N-(p-methoxyphenyl)-4-vinyl-2-oxazolidinone (2a). Method A. To a solution of Ni(COD)₂ (13.2 mg, 48 μmol) and TPP (25 mg, 96 μmol) in THF (2 mL) was cannulated 1a (75 mg, 0.24 mmol) in THF (1 mL), and then LiHMDS (1.0M in hexane, 0.24 mL, 0.24 mmol) was added slowly via syringe. The reaction mixture was stirred for 1 h and quenched with NH₄Cl (aq.) followed by extraction with ethyl ether. The organic layer was dried (MgSO₄), filtered, concentrated and chromatographed (25→33% EtOAc-hexanes) to yield 2a (47 mg, 89%): ¹H NMR (300 MHZ, CDCl₃) δ3.77 (s, 3H), 4.08 (dd, J=7, 9 Hz, 1H), 4.56 (t, J=9 Hz, 1 H), 4.71–4.78 (m, 1H), 5.27 (dd, J=0.7, 10 Hz, 1H), 5.30 (dd, J=0.7, 17 Hz, 1H), 5.76 (ddd, J=8, 10, 17 Hz, 1H); ¹³C NMR (75 MHZ, CDCl₃) δ 55.3, 60.2, 66.9, 114.1, 120.6, 124.0, 129.6, 134.7, 156.0, 157.1; IR(ATR) 1752, 2934 cm⁻¹; HRMS (FAB, 3-NBA, NaI) calculated for C₁₂H₁₃NO₃Na (M+Na⁺) 242.0793, observed 242.0790.

Method B. A mixture of Ni(PPh₃)₂Cl₂ (423 mg, 0.65 mmol), TPP (339 mg, 1.29 mmol) and zinc dust (83 mg, 1.29 mmol) in THF (20 mL) was stirred under Ar for 0.5 h at rt to generate Ni(0), resulting in a change of color from green-blue to reddish brown. To this was added a solution of 1a (1 g, 3.23 mmol) in THF (10 mL) via cannula, followed by LiHMDS (1.0 M in hexane, 3.23 mL, 3.23 mmol), slowly via syringe. The reaction mixture was stirred for 30 min, quenched with NH₄Cl (aq.) and then extracted with ethyl ether. The organic layer was dried (MgSO₄), filtered, concentrated, and chromatographed (25→33% EtOAc-hexanes) to yield 2a (598 mg, 85%).

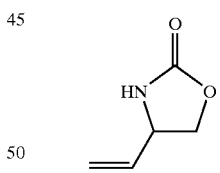

4-Vinyl-2-oxazolidinone. To a solution of 2a (1.73 g, 7.90 mmol) in CH₃CN (175 mL) was added concentrated ammonium nitrate (13.0 g, 23.7 mmol) in H₂O (87 mL) dropwise at 0° C. The reaction mixture was stirred at 0° C. for 20 min and then quenched with saturated aqueous sodium sulfite followed by extraction with ethyl acetate. After drying (MgSO₄) and evaporation, the residue was purified by silica gel column chromatography (33→50% EtOAc-hexanes) to afford the vinyl oxazolidinone (694 mg, 78%): ¹H NMR (300 MHZ, CDCl₃) δ3.97 (dd, J=6, 8 Hz, 1H), 4.28–4.36 (m, 1H), 4.45 (appt, J=8 Hz, 1H), 5.15 (dt, J=1, 10 Hz, 1H), 5.24 (dt, J=1, 17 Hz, 1H), 5.74 (ddd, J=7, 10, 17 Hz, 1H), 6.81 (br s, 1H); ¹³C NMR (75 MHZ, CDCl₃) δ 54.9, 69.8, 118.1, 135.6, 160.0; HRMS (FAB, 3-NBA) calculated for C₅H₈NO₂ [(M+H)⁺] 114.0555, observed 114.0551.

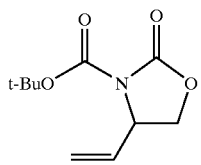

N-(tert-Butoxycarbonyl)-4-vinyl-2-oxazolidinone. To a solution of vinyl oxazolidinone (0.35 g, 3.12 mmol) in CH$_2$Cl$_2$ (30 mL) and Et$_3$N (0.65 mL, 4.68 mmol) was added a solution of Boc$_2$O (2 g, 9.37 mmol) in CH$_2$Cl$_2$ (10 mL) at rt. The reaction was stirred for 60 h. The reaction was quenched with H$_2$O and extracted with CH$_2$Cl$_2$, dried over MgSO$_4$ and concentrated in vacuo. The crude product was purified by silica gel column chromatography (20% EtOAc-hexanes) to yield the Boc-protected vinyl oxazolidinone (583 mg, 88%): $^1$H NMR (300 MHZ, CDCl$_3$) δ1.45 (s, 9H), 3.98 (dd, J=4, 9 Hz, 1H), 4.39 (appt, J=9 Hz, 1H), 4.67 (ddd, J=4, 7, 9 Hz, 1H), 5.26 (d, J=10 Hz, 1H), 5.27 (d, J=17 Hz, 1H), 5.82 (ddd, J=7, 10, 17 Hz, 1H); $^{13}$C NMR (75 MHZ, CDCl$_3$) δ 27.7, 57.1, 66.6, 83.7, 118.5, 134.4,148.9, 152.1; IR (ATR) 1724, 1811, 2981 cm$^{-1}$; HRMS (FAB, 3-NBA) calculated for C$_{10}$H$_{16}$NO$_4$ [(M+H)$^+$] 214.1079, observed 214.1073.

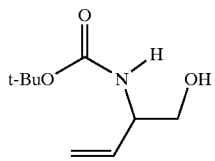

N-(tert-Butoxycarbonyl)-2-vinylglycinol (3). To a solution of Boc-protected vinyl oxazolidinone (1.13 g, 5.30 mmol) in MeOH (50 mL) was added Cs$_2$CO$_3$ (345 mg, 1.06 mmol). After the reaction mixture was stirred for 1.5 h, saturated aqueous NH$_4$Cl solution was added and MeOH was evaporated. The product was extracted with CH$_2$Cl$_2$, dried (MgSO$_4$) and concentrated. Flash chromatography (25→33% EtOAc-hexanes) gave the product 3 (872 mg, 88%): $^1$H NMR (300 MHZ, CDCl$_3$) δ1.43 (s, 9H), 2.49 (br s, 1H), 3.60 (dd, J=5, 11 Hz, 1H), 3.69 (dd, J=4, 11 Hz, 1H), 4.22 (br s, 1H), 4.94 (br s, 1H) 5.21 (d, J=10 Hz, 1H), 5.25 (d, J=16 Hz, 1H), 5.79 (ddd, J=5, 10, 16 Hz, 1H); $^{13}$C NMR (75 MHZ, CDCl$_3$) δ 28.1, 54.4, 64.4, 115.9, 135.6, 155.9; IR (ATR) 1683, 2977, 3337 cm$^{-1}$; HRMS (FAB, 3-NBA, LiI) calculated for C$_9$H$_{17}$NO$_3$Li (M+Li$^+$) 194.1368, observed 194.1359.

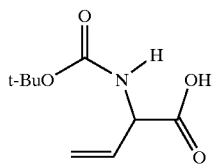

N-(tert-Butoxycarbonyl)-2-vinylglycine. To a solution of 3 (50 mg, 0.267 mmol) in acetone (5 mL) was added Jones reagent (4 M, 0.2 mL, 0.8 mmol) at 0° C. over 10 min and the reaction mixture was then stirred for 3 h at rt. Excess Jones reagent was quenched by addition of i-PrOH. The acetone and i-PrOH were removed under reduced pressure, and the residue was partitioned between water and ethyl acetate. The organic phase was separated and the product was extracted into saturated aqueous Na$_2$CO$_3$ solution. Acidification of the aqueous phase to pH 4 with acetic acid followed by extraction with ethyl acetate, drying (MgSO$_4$), filtration and evaporation gave Boc-protected vinylglycine (44 mg, 82%): $^1$H NMR (300 MHz, DMSO-d$_6$) δ1.37 (s, 9H), 4.51 (dd, J=6, 7 Hz, 1H), 5.17 (d, J=10 Hz, 1H), 5.28 (d, J=17 Hz, 1H), 5.87 (ddd, J=6, 10, 17 Hz, 1H), 7.30 (d, J=7 Hz, 1H), 12.65 (br s, 1H); $^{13}$C NMR (75 MHZ, CDCl$_3$) δ 28.2, 56.2, 78.2, 117.1, 133.1, 155.2, 172.0; HRMS (FAB, 3-NBA, NaI) calculated for C$_9$H$_{15}$NO$_4$ Na (M+Na$^+$) 224.0899, observed 224.0893.

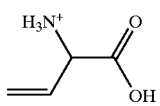

α-Vinylglycine, Trifluoroacetate Salt (4). To a solution of Boc-protected vinylglycine (82 mg, 0.41 mmol) in CH$_2$Cl$_2$ (10 mL) at 0° C. was added CF$_3$COOH (3 mL). After 3 h at room temperature, H$_2$O was added, followed by extraction with CH$_2$Cl$_2$ and Et$_2$O. Evaporation of the aqueous layer, followed by thorough drying in vacuo (Δ, P$_2$O$_5$ sidearm) provided 4$^2$ (74 mg, 84%): $^1$H NMR (300 MHz, D$_2$O) δ 4.58 (d, J=7 Hz, 1H), 5.54 (d, J=17 Hz, 1H), 5.55 (d, J=110 Hz, 1H), 5.97 (ddd, J=7, 10, 17 Hz, 1H); HRMS (FAB, 3-NBA) calculated for C$_4$H$_{18}$NO$_2$ [(M+H)$^+$] 102.0555, observed 102.0554.

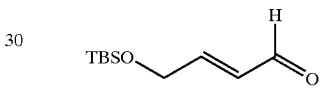

E)-4-tert-Butyldimethylsilyloxy-2-butenal (5). To a solution of oxalyl chloride (21 mL, 24.7 mmol, 2.0 M in CH$_2$Cl$_2$) in CH$_2$Cl$_2$ (30 mL) at −78° C. was added a solution of DMSO (3.3 mL, 49.4 mmol) in CH$_2$Cl$_2$ (30 mL) via cannula. After stirring for 10 min at −78° C., a solution of starting alcohol$^3$ (5.0 g, 24.7 mmol) in CH$_2$Cl$_2$ (50 mL) was added, dropwise via cannula. After an additional 30 min at −78° C., a solution of NEt$_3$ (12.05 mL, 86.48 mmol) in CH$_2$Cl$_2$ (20 mL) was added in the same manner. After 1 h at −78° C., Et$_2$O was then added at −78° C. and the reaction mixture was allowed to warm to rt. The crude reaction mixture was then poured into Et$_2$O and extracted sequentially with (H$_2$O and saturated NH$_4$Cl. After drying (MgSO$_4$), filtration and evaporation, column chromatography (10% EtOAc/hexane) provided aldehyde 5 (4.01 g, 81%): $^1$H NMR (300 MHZ, CDCl$_3$) δ0.06 (s, 6H), 0.89 (s, 9H), 4.43 (dd, J=2, 3 Hz, 2H), 6.37 (ddt, J=2, 8, 16 Hz, 1H), 6.86 (dt, J=5, 16 Hz, 1H), 9.85 (d, J=8 Hz, 1H); IR (ATR) 1690, 2955 cm$^{-1}$; $^{13}$C NMR (75 MHZ, CDCl$_3$) δ 5.5, 18.3, 25.7, 62.2, 130.5, 156.4, 193.3.

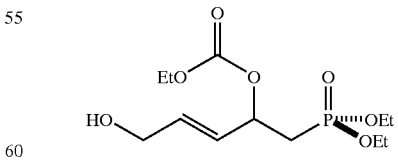

Ethyl (2E)-1-(Diethylphosphonomethyl)-4-hydroxy-2-butenyl Carbonate (6). To a solution of diethyl methylphosphonate (292 mg, 1.92 mmol) in THF (5 mL) at −78° C. was added n-BuLi (1.34 mL, 1.92 mmol, 1.43 M in hexanes) dropwise via syringe. After stirring for 30 min at −40° C., a solution of 5 (320 mg, 1.60 mmol) in THF (5 mL) was added, dropwise, via cannula. After 30 min at the same temperature, ethyl chloroformate (0.38 mL, 2.40 mmol) was added slowly, and the reaction was allowed to warm to rt. Then 0.3 M HCl solution (5 mL) was added and stirring continued overnight. The reaction mixture was extracted with CH$_2$Cl$_2$ and dried over MgSO$_4$ and concentrated in vacuo. Purification by a silica gel column chromatography (EtOAc) to yielded 6 (336 mg, 68%): $^1$H NMR (300 MHZ, CDCl$_3$) δ1.26–1.33 (m 9H), 2.07 (s, 1H), 2.13 (ddd, J=7, 15, 19 Hz, 1H), 2.30 (ddd, J=7, 15, 118 Hz, 1H), 4.04–4.21 (m, 8H), 5.35–5.45 (m, 1H), 5.78 (ddt, J=2, 7, 16 Hz, 1H), 5.98 (ddt, J=1, 5, 16 Hz, 1H); $^{13}$C NMR (75 MHZ, CDCl$_3$) δ13.8, 15.8, 15.9, 31.1 (d, J=140.8 Hz), 61.2, 61.58 (d, J=5.5 Hz), 61.65 (d, J=5.5 Hz), 63.6, 72.5, 126.27 (d, J=8.8 Hz), 134.0, 153.6; $^{31}$P NMR (121 MHZ, CDCl$_3$) δ25.17; HRMS (FAB, 3-NBA) calculated for C$_{12}$H$_{23}$O$_7$P [(M+H)$^+$] 311.1260, observed 311.1267.

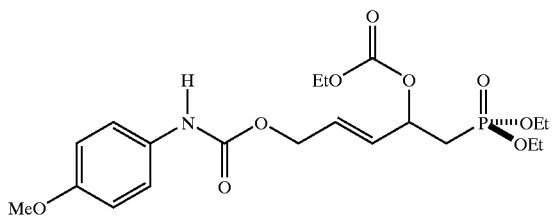

Diethyl 2-Ethoxycarbonyloxy-5-[(p-methoxyanilino] carbonyloxy]-(3E)-pentenylphosphonate (7). To a solution of 6 (1.14 g, 3.67 mmol) in THF (30 mL) at 0° C. were added sequentially pyridine (0.45 mL, 5.51 mmol) and p-methoxyphenyl isocyanate (0.57 mL, 4.41 mmol), via syringe. After allowing the reaction mixture to warm to rt and stir for 36 h, ether was added. The organic phase was washed with saturated CuSO$_4$ solution. After drying (MgSO$_4$), filtration and evaporation, the crude product was purified by SiO$_2$ chromatography (50→100% EtOAc-hexanes) to provide 7 (1.63 g, 96%): $^1$H NMR (300 MHZ, CDCl$_3$) δ1.20 (t, J=7 Hz, 3H), 1.23 (t, J=7 Hz, 6H), 2.06 (ddd, J=6, 15, 19 Hz, 1H), 2.22 (ddd, J=7, 15, 17 Hz, 1H), 3.68 (s, 3H), 4.02 (overlapping app q, J=7 Hz, 4H), 4.10 (q, J=7 Hz, 2H), 4.56 (d, J=5 Hz, 2H), 5.31–5.41 (m, 1H), 5.77 (dd, J=6, 16 Hz, 1H), 5.87 (dt, J=5, 16 Hz, 1H), 6.72–6.77 (m, 2H), 7.26 (br d, J=9 Hz, 2H), 7.52 (br s, 1H); $^{13}$C NMR (75 MHZ, CDCl$_3$) δ 14.0, 16.0, 16.1, 31.24 (d, J=140.8 Hz), 55.2, 61.74 (d, J=5.5 Hz), 63.79 (d, J=17.6 Hz), 72.2, 113.9, 120.4, 128.3, 129.94 (d, J=9.9 Hz), 131.1, 153.5, 153.7, 155.6; $^{31}$P NMR (121 MHZ, CDCl$_3$) 624.95; IR (ATR) 1250, 1730, 2981, 3250 cm$^{-1}$; HRMS (FAB, 3-NBA, LiI) calculated for C$_{20}$H$_{30}$NO$_9$PLi (M+Li$^+$) 466.1818, observed 466.1835.

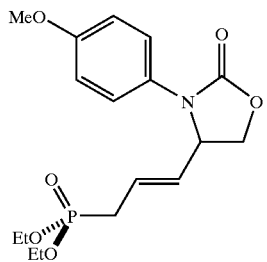

N-(p-Methoxyphenyl)-4-[(3'-diethylphosphono)-1'E-propenyl]-2-oxazolidinone (8). Method A. To a solution of Ni(COD)$_2$ (12 mg, 44 µmol) and dppb (19 mg, 44 µmol) in THF (3.5 mL), was cannulated 7 (100 mg, 0.22 mmol) and then LiHMDS (1 M in hexane, 0.22 mL, 0.22 mmol) was added slowly via syringe. The reaction mixture was stirred for 90 min and quenched with NH$_4$Cl (aq.) followed by extraction with ethyl ether. The organic layer was dried (MgSO$_4$), filtered, concentrated, and chromatographed (EtOAc) to yield 8 (64 mg, 79%): $^1$H NMR (300 MHZ, CDCl$_3$) δ 1.13 (t, J=7 Hz, 3H), 1.16 (t, J=7 Hz, 3H), 2.47 (dd, J=7, 21 Hz, 2H), 3.69 (s, 3H), 3.78–4.02 (m, 5H), 4.49 (appt, J=8 Hz, 1H), 4.67–4.75 (m, 1H), 5.50 (ddd, J=5, 8, 15 Hz, 1H), 5.60–5.72 (m, 1H); $^{13}$C NMR (75 MHZ, CDCl$_3$) δ16.1, 16.2, 29.9 (d, J=139.7 Hz), 55.2, 59.3, 61.7 (d, J=4.4 Hz), 61.8 (d, J=4.4 Hz), 66.89 (d, J=4.4 Hz), 114.0, 124.0, 126.1 (d, J=11.0 Hz), 129.4, 131.5 (d, J=14.3 Hz), 155.8, 157.0; $^{31}$P NMR (121 MHz, CDCl$_3$) δ25.30; IR (ATR) 1245, 1747, 2981 cm$^{-1}$; HRMS (FAB, 3-NBA, LiI) calculated for C$_{17}$H$_{24}$NO$_6$PLi (M+Li$^+$) 376.1501, observed 376.1513.

Method B. To a solution of Ni(COD)$_2$ (12 mg, 44 µmol) and TPP(23 mg, 88 µmol) in THF(3.5 mL) was cannulated 7 (100 mg, 0.22 mmol) and then LiHMDS (1 M in hexane, 0.22 mL, 0.22 mmol) was added slowly via syringe. The reaction mixture was stirred for 90 min and quenched with NH$_4$Cl (aq.) followed by extraction with ethyl ether. The organic layer was dried (MgSO$_4$), filtered, concentrated, and chromatographed (EtOAc) to yield 8 (63 mg, 77%).

Method C. A mixture of Ni(PPh$_3$)$_2$Cl$_2$ (142 mg, 0.22 mmol), TPP (114 mg, 0.44 mmol), zinc dust (28 mg, 0.44 mmol), in THF (8 mL) were stirred for 0.5 h at rt under Ar to generate Ni(0) (color change from green-blue to reddish brown). Then 7 (0.5 g, 1.09 mmol) in THF (8 mL) was added, via cannula, followed by LiHMDS (1 M in hexane, 1.09 mL, 1.09 mmol). The reaction mixture was stirred for 2 h. and then quenched with NH$_4$Cl (aq.) followed by extraction with ethyl ether. The organic layer was dried (MgSO$_4$), filtered, concentrated, and chromatographed (EtOAc) to yield 8 (280 mg, 70%).

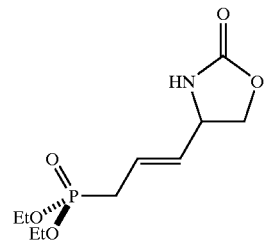

4-[(3'-Diethylphosphono)-1'E-propenyl]-2-oxazolidinone. To a solution of 8 (360 mg, 0.98 mmol) in CH$_3$CN (23 mL) was added CAN (1.60 g, 2.92 mmol) in H$_2$O (11 mL) dropwise at 0° C. The reaction mixture was stirred at 0° C. for 20 min and quenched with saturated aqueous sodium sulfite, followed by extraction with ethyl acetate. After drying (MgSO$_4$) and evaporation, the residue was purified by silica gel column chromatography (5% MeOH-EtOAc) to afford the title oxazolidinone (229 mg, 89%): $^1$H NMR (300 MHZ, CDCl$_3$) δ1.27 (t, J=7 Hz, 6H), 2.55 (dd, J=7, 22 Hz, 2H), 3.95–4.10 (m, 5H), 4.31–4.39 (m, 1H), 4.67 (appt, J=8 Hz, 1H), 5.58 (ddd, J=4, 7, 16 Hz, 1H), 5.63–5.75 (m, 2H); $^{13}$C NMR (75 MHZ, CDCl$_3$) δ16.0, 16.1, 29.55 (d, J=139.7 Hz), 54.1(d, J=2.2 Hz), 61.75 (d, J=4.4 Hz), 61.82 (d, J=4.4 Hz), 69.46 (d, J=4.4 Hz), 123.22 (d, J=11.0 Hz), 132.8 (d, J=14.3 Hz), 155.8, 157.0; $^{31}$P NMR (121 MHZ, CDCl$_3$) δ25.84; IR (ATR) 1224, 1746, 3237 cm$^{-1}$; HRMS (FAB, 3-NBA) calculated for C$_{10}$H$_{19}$NO$_5$P [(M+H)$^+$] 264.1000, observed 264.0992.

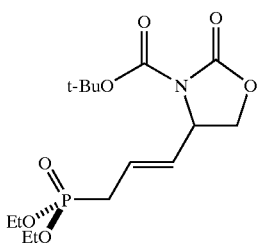

N-tert-Butoxycarbonyl-4-[(3'-diethylphosphono)-1'E-propenyl]-2-oxazolidinone. To a solution of the preceding oxazolidinone (220 mg, 0.84 mmol) in THF (15 mL) was added LiHMDS (1.0 M in THF, 1.25 mL) and then a solution of Boc$_2$O (547 mg, 2.50 mmol) in THF (3 mL) at rt. The reaction mixture was stirred for 30 min and quenched with H$_2$O. Extraction (EtOAc), drying (MgSO$_4$), concentration and chromatography (5% MeOH-EtOAc) yielded the Boc-protected oxazolidinone (258 mg, 85%): $^1$H NMR (300 MHZ, CDCl$_3$) δ1.26 (t, J=7 Hz, 6H), 1.46 (s, 9H), 2.56 (dd, J=6, 22 Hz, 2H), 3.95–4.09 (m, 4H), 3.97 (dd, J=4, 9 Hz, 1H), 4.37 (appt, J=9 Hz, 1H), 4.63–4.70 (m, 1H), 5.62 (ddd, J=4, 7, 15 Hz, 1H), 5.68–5.78 (m, 1H); $^{13}$C NMR (75 MHZ, CDCl$_3$) δ 16.05, 16.10, 27.5, 29.7 (d, J=139.7 Hz), 56.2, 61.6 (d, J=6.6 Hz), 61.7 (d, J=5.5 Hz), 66.5 (d, J=3.3 Hz), 124.3 (d, J=11.0 Hz), 131.0 (d, J=14.3 Hz); $^{31}$P NMR (121 MHZ, CDCl$_3$) δ25.58; IR (ATR) 1243, 1723, 1803, 2981 cm$^{-1}$; HRMS (FAB, 3-NBA) calculated for C$_{15}$H$_{27}$NO$_7$P [(M+H)$^+$] 364.1525, observed 364.1532.

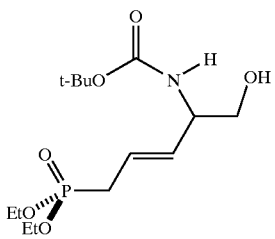

2-(tert-Butoxycarbonyl)amino-5-diethylphosphono-3E-pentenol (9) To a solution of Boc-protected oxazolidinone (250 mg, 0.69 mmol) in EtOH (20 mL) was added Cs$_2$CO$_3$ (45 mg, 0.14 mmol). After the reaction mixture was stirred for 1.5 h, saturated, aqueous NH$_4$Cl was added and the EtOH was evaporated. Following extraction CH$_2$Cl$_2$, drying (MgSO$_4$) and concentration, flash chromatography (5% MeOH-EtOAc) provided 9 (220 mg, 95%): $^1$H NMR (300 MHZ, CDCl$_3$) δ1.27 (t, J=7 Hz, 6H), 1.39 (s, 9H), 2.56 (dd, J=5, 22 Hz, 2H), 3.50 (br s, 1H), 3.56 (dd, J=5, 11 Hz, 1H), 3.61 (dd, J=4, 11 Hz, 1H), 3.99–4.12 (m, 1H), 5.28 (br s, 1H), 5.51–5.68 (m, 2H); $^{13}$C NMR (75 MHZ, CDCl$_3$) δ16.11, 16.19, 28.1, 29.7 (d, J=139.7 Hz), 53.8, 61.95 (2 C), (d, J=6.6 Hz), 64.37 (d, J=2.2 Hz), 79.0, 119.9 (d, J=9.9 Hz), 133.9 (d, J=14.3 Hz), 155.5; $^{31}$P NMR (121 MHZ, CDCl$_3$) δ27.20; IR (ATR) 1165, 1708, 2979, 3361 cm$^{-1}$; HRMS (FAB, 3-NBA) calculated for C$_{14}$H$_{29}$NO$_6$P [(M+H)$^+$] 338.1733, observed 338.1744.

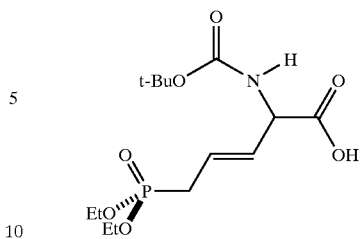

2-(tert-Butoxycarbonyl)amino-5-diethylphosphono-3E-pentenoic Acid. To a solution of 9 (100 mg, 0.30 mmol) in acetone (5 mL) was added Jones reagent (4 M, 0.22 mL, 0.89 mmol) at 0° C. over 10 min, and the reaction mixture was stirred for 3 h at rt. Excess Jones reagent was quenched with i-PrOH. The acetone and i-PrOH were removed under reduced pressure, and the residue was partitioned between water and ethyl acetate. The organic phase was separated and the product was extracted into saturated aqueous Na$_2$CO$_3$ solution. Acidification (pH 4) with acetic acid followed by extraction with EtOAc, drying (MgSO$_4$), filtration and evaporation gave the product (79 mg, 76%): $^1$H NMR (300 MHz, DMSO-d$_6$) δ 1.19 (t, J=7 Hz, 6H), 1.36 (s, 9H), 2.60 (dd, J=7, 22 Hz, 2H), 3.95 (overlapping app q, J=7 Hz, 1H), 4.30–4.39 (m, 1H), 5.43–5.55 (m, 1H), 5.62–5.74 (m, 1H), 6.80–6.89 (m, 1H); $^{13}$C NMR (75 MHz, DMSO-d$_6$) δ16.20, 16.27, 28.2, 29.0 (d, J=152.9 Hz), 56.1, 61.23 (d, J=2.2 Hz), 61.31 (d, J=3.3 Hz), 120.3 (d, J=12.1 Hz), 131.6 (br), 154.9, 171.7; $^{31}$P NMR (121 MHz, DMSO-d$_6$) δ27.23; HRMS (FAB, 3-NBA, NaI) calculated for C$_{14}$H$_{26}$NO$_7$P [(M+Na)$^+$] 374.1345, observed 374.1332.

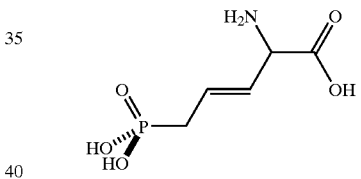

(E)-2-Amino-5-phosphono-3-pentenoic Acid (10). To a solution of acid (30 mg, 0.085 mmol) in CH$_3$CN (2 mL) at 0° C. was added TMSI (0.11 mL, 0.77 mmol). After allowing to warm to rt and stirring for 6 h, H$_2$O (. 200 μL) was added. Evaporation of the volatiles yields 10 (17 mg, ca. 70%). Further purification could be achieved via flash chromatography {CH$_3$COCH$_3$/CH$_2$Cl$_2$/MeOH(45:45:10)→i-PrOH/CH$_3$CN/50 mM NH$_4$HCO$_3$ (aq) (2:1:1)} followed by several lyophilization cycles, and then thorough drying in vacuo (P$_2$O$_5$ sidearm, 50° C.), to provide a sample of as the ammonium salt: $^1$H NMR (500 MHz, D$_2$O) δ2.53 (dd, J=8, 21 Hz, 2H), 4.29 (d, J=9 Hz, 1H), 5.67 (ddd, J=5, 9, 14 Hz, 1H), 5.99–6.07 (m, 1H); $^{13}$C NMR (125 MHz, D$_2$O; HMBC) δ33.8, 57.1; 124.3, 133.8, 173.9; $^{31}$P NMR (202 MHz, D$_2$O) δ18.44.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

We claim:

1. A biphasic process for monitoring the relative rates of two or more organic reactions, the process for each reaction comprising:

preparing a cell having an organic solvent layer and an adjacent aqueous solvent layer containing at least one enzyme, and optionally, coenzymes or co-substrates;

introducing a starting material into the organic solvent layer;

reacting the starting material to produce a product and, optionally, a byproduct; the product or the byproduct diffusing from the organic solvent layer into the adjacent aqueous solvent layer; wherein the product or the byproduct acts as a substrate for a reaction that is catalyzed by the enzyme or a sequence of more than one enzyme to produce a spectroscopically observable change; and monitoring the spectroscopic change to determine the relative rate of the product or a the byproduct formation in the organic solvent layer.

2. The biphasic process of claim 1 wherein the byproduct is produced by the reacting starting material and the byproduct diffuses from the organic solvent layer into the adjacent aqueous solvent layer.

3. The biphasic process of claim 2 wherein the byproduct is an alcohol, a carbonate mono ester, a carboxylate, an acetate, a sulfate, a phosphate, or carbon dioxide.

4. The biphasic process of claim 3 wherein the byproduct is methanol, ethanol, 2-propanol, 1-butanol, an alkyl alcohol, a methyl carbonate, an ethyl carbonate, a sulfate monoester, a sulfate diester, or a phosphate monoester, diester, or carbon dioxide.

5. The biphasic process of claim 1 wherein the product diffuses from the organic solvent layer into the adjacent aqueous solvent layer.

6. The biphasic process of claim 5 wherein the product is an alcohol, a 1,2-diol, a halohydrin, a β-azido alcohol, a β-cyanoalcohol, a β-alkoxy alcohol, a β-thioalkyl alcohol, an amine, a 1,2-diamine, or β-hydroxy amine.

7. The biphasic process of claim 1 wherein the organic solvent layer is substantially immiscible with the aqueous solvent layer.

8. The biphasic process of claim 1 wherein the organic solvent layer comprises a catalyst or promoter.

9. The biphasic process of claim 1 wherein the organic solvent layer lies above the aqueous solvent layer.

10. The biphasic process of claim 1 wherein the aqueous solvent layer lies above the organic solvent layer.

11. The biphasic process of claim 1 wherein the organic solvent layer comprises a single organic solvent.

12. The biphasic process of claim 1 wherein the organic solvent layer comprises a mixture of organic solvents.

13. The biphasic process of claim 1 wherein the organic solvent is selected from the group consisting of hexane, benzene, cyclohexane, pentane, heptane, 1,2-dimethoxyethane, dioxane, 1,2-dichloroethane, 1,2,3,4-tetrachloroethane, tetrahydrofuran, toluene, carbon tetrachloride, chloroform, ethyl acetate, methyl t-butyl ether, methylene chloride, diethyl ether, and mixtures thereof.

14. The biphasic process of claim 1 wherein the organic solvent is a fluorocarbon solvent and the starting material contains a fluorocarbon component, whereas the product or optional byproduct does not.

15. The biphasic process of claim 1 wherein the reaction involves formation or cleavage of an O—C, N—C, S—C, C—C, O—P, N—P, or X—C bond, wherein X is a halogen.

16. The biphasic process of claim 1 wherein the aqueous solvent layer contains a buffer.

17. The biphasic process of claim 13 wherein the buffer is selected from the group consisting of pyrophosphate, phosphate, tris, imidazole, MOPS, MES, acetate, borate, triethanolamine, HEPES, glycine, BICINE, and TRICINE.

18. The biphasic process of claim 1 wherein the product or byproduct is an enzymatic substrate for an enzyme/coenzyme couple.

19. The biphasic process of claim 15 wherein the enzyme/coenzyme couple is selected from the group consisting of:

alcohol dehydrogenase/NAD(P)$^+$;

alcohol dehydrogenase/NAD(P)$^+$, aldehyde dehydrogenase/NAD(P)$^+$;

ATP-dependent acetate kinase/ATP, pyruvate kinase/PEP, D- or L-lactate dehydrogenase/NAD(P)H;

pyrophosphate-dependent acetate kinase/pyrophosphate, glyceraldehyde 3-phosphate dehydrogenase/GAP/NAD(P)$^+$;

ATP-dependent butyrate kinase/ATP, pyruvate kinase/PEP, D- or L-lactate dehydrogenase/NAD(P)H;

ATP sulfurylase/ATP, pyrophosphatase, glyceraldehyde 3-phosphate dehydrogenase/GAP/NAD(P)$^+$;

sulfatase; ATP sulfurylase/ATP, pyrophosphatase, glyceraldehyde 3-phosphate dehydrogenase/GAP/NAD(P)$^+$;

ATP sulfurylase/ATP, adenylyl sulfate kinase/ATP, pyruvate kinase/PEP, D- or L-lactate dehydrogenase/NAD(P)H;

sulfatase; ATP sulfurylase/ATP, adenylyl sulfate kinase/ATP, pyruvate kinase/PEP, D- or L-lactate dehydrogenase/NAD(P)H;

a phosphohydrolase enzyme or enzymes capable of cleaving both phosphate diesters and monoesters, glyceraldehyde 3-phosphate dehydrogenase/GAP/NAD(P)$^+$;

glyceraldehyde dehydrogenase/GAP/NAD(P)$^+$;

a phosphohydrolase enzyme or enzymes capable of cleaving both phosphate diesters and monoesters, glyceraldehyde 3-phosphate dehydrogenase/GAP/NAD(P)$^+$, alcohol dehydrogenase/NAD(P)$^+$, and aldehyde dehydrogenase/NAD(P)$^+$;

alcohol oxidase/O$_2$, peroxidase/dye;

amine oxidase/O$_2$, peroxidase/dye; and carbonic anhydrase/water soluble aminomethyl anthracene derivative.

20. The biphasic process of claim 18 wherein the enzyme/coenzyme couple is selected such that the enzyme/coenzyme couple can detect a product or byproduct selected from the group consisting of alcohols, 1,2-diols, acetate, phosphate and mono- or diesters thereof, sulfate and monoesters thereof, amines, aminoalcohols and carbon dioxide.

21. The biphasic process of claim 1 wherein the spectroscopically observable change comprises the production of a spectroscopically observable compound.

22. The biphasic process of claim 1 wherein the spectroscopically observable change comprises the consumption of a spectroscopically observable compound.

23. The biphasic process of claim 1 further comprising monitoring the spectroscopically observable change by transmitting radiation through the aqueous solvent layer and monitoring absorbance.

24. The biphasic process of claim 1 further comprising monitoring the spectroscopically observable change by irradiating the aqueous layer at wavelengths permitting chromophore absorption and monitoring chromophore fluorescence.

25. The biphasic process of claim 21 wherein the spectroscopically observable compound is selected from the group consisting of coenzymes and cofactors.

26. The biphasic process of claim 25 wherein the spectroscopically observable compound is selected from the group consisting of NAD(P)H analogues and NAD(P)H.

27. The biphasic process of claim 25 wherein the spectroscopically observable compound is selected from the group consisting of the reduced forms of NAD+, NADP+, 3-acetylpyridine adenine dinucleotide, 3-formylpyridine adenine dinucleotide, and thiononicotinamide adenine dinucleotide.

28. The biphasic process of claim 21 wherein the spectroscopically observable compound is selected from the group consisting of a riboflavin cofactor and a cofactor dye.

29. The biphasic process of claim 1 wherein the spectroscopically observable change is monitored visually.

30. The biphasic process of claim 1 wherein the product or byproduct is an alcohol or amine and the enzyme is an alcohol oxidase or an amine oxidase, repsectively, which reaction produces hydrogen peroxide and the hydrogen peroxide is spectroscopically monitored in a reaction with a chemilumescent indicator.

31. A biphasic process for comparing the rates of a series of organic reactions run in parallel, the process comprising:

preparing several parallel cells having an organic solvent layer and an adjacent aqueous solvent layer containing at least one enzyme and optionally coenzymes or co-substrates;

introducing a starting material into the organic solvent layer of each cell;

reacting the starting material to produce a product and, optionally, a byproduct within each cell, the product or byproduct diffusing from the organic solvent layer into the adjacent aqueous solvent layer; wherein the product or byproduct acts as substrate for a reaction that is catalyzed by the enzyme or a sequence of more than one enzyme to produce a spectroscopic change; and monitoring the spectroscopic change to determine the relative rates of product formation in the organic layers of the parallel cells.

32. The biphasic process of claim 31 further comprising combining a starting material and a catalyst or promoter in each of the several parallel cells, wherein the catalyst or promoter of each cell may be the same or different and may be of the same concentration or different, and further comprising comparing the rates of organic reactions run in the parallel cells to evaluate the efficacy of the catalyst or promoter.

33. The biphasic process of claim 31 further comprising comparing the rates of a series of allylic substitution reactions run in parallel, the process comprising:

introducing, in the several parallel cells, an allylic substrate which includes the structural element C=C—C—X, where X is a byproduct, into the organic solvent layer and reacting the allylic substrate with Nu, where Nu is a nucleophile either within the allylic substrate or in a separate compound, in the presence of a transition metal catalyst to generate a product which includes the structural element C=C—C—Nu, the transition metal catalyst comprising a transition metal and one or more ligands, the byproduct diffusing from the organic layer into the adjacent aqueous solvent layer and serving as the substrate in the aqueous solvent layer to produce a spectroscopic change; and monitoring said spectroscopic change to determine the relative rates of product formation in the organic solvent layers of the parallel reactions.

34. The process as set forth in claim 33 wherein X is methanol, ethanol or acetate.

35. The process as set forth in claim 31 wherein the enzyme and coenzyme couple is ADH/NAD(P)$^+$ or AlDH/NAD(P)$^+$;

alcohol oxidase/$O_2$ and peroxidase/dye or chemiluminescence indicator;

acetate kinase/ATP, pyruvate kinase/PEP, D- or L-lactate dehydrogenase; or pyrophosphate-dependent acetate kinase/pyrophosphate, glyceraldehyde 3-phosphate dehydrogenase/GAP/NAD(P)$^+$.

* * * * *

UNITED STATES PATENT AND TRADEMARK OFFICE
CERTIFICATE OF CORRECTION

PATENT NO. : 6,974,665 B2  Page 1 of 1
APPLICATION NO. : 10/235950
DATED : December 13, 2005
INVENTOR(S) : David B. Berkowitz, Mohua Bose and Sungjo Choi It is certified that error appears in the above-identified patent and that said Letters Patent is hereby corrected as shown below:

Col. 1, line 3;
Add the Government Support Clause as follows:

-- This invention was made with government support under CHE0317083 awarded by the National Science Foundation. The government has certain rights in the invention. --

Signed and Sealed this

Sixth Day of May, 2008

JON W. DUDAS
*Director of the United States Patent and Trademark Office*